(12) United States Patent
Mueller et al.

(10) Patent No.: US 9,217,169 B2
(45) Date of Patent: *Dec. 22, 2015

(54) SYNTHETIC PATHWAY ENZYMES FOR THE PRODUCTION OF ARGYRINS

(71) Applicant: Helmholtz-Zentrum fuer Infektionsforschung GmbH, Braunschweig (DE)

(72) Inventors: Rolf Mueller, Blieskastel (DE); Silke Wenzel, Ahnatal (DE); Ronald Garcia, Saarbruecken (DE)

(73) Assignee: Helmholtz-Zentrum fuer Infektionsforschung GmbH, Braunschweig (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/779,212

(22) Filed: Feb. 27, 2013

(65) Prior Publication Data
US 2013/0295606 A1 Nov. 7, 2013

Related U.S. Application Data

(62) Division of application No. 12/999,872, filed as application No. PCT/EP2009/057336 on Jun. 15, 2009, now Pat. No. 8,404,462.

(30) Foreign Application Priority Data

Jul. 4, 2008 (EP) ..................................... 08159743

(51) Int. Cl.
| | |
|---|---|
| C12P 21/02 | (2006.01) |
| C07K 7/56 | (2006.01) |
| C12N 15/52 | (2006.01) |
| C12P 17/16 | (2006.01) |
| C12N 9/02 | (2006.01) |
| C12N 9/10 | (2006.01) |
| C12N 9/22 | (2006.01) |
| C12N 9/88 | (2006.01) |
| C12N 15/74 | (2006.01) |

(52) U.S. Cl.
CPC . *C12P 21/02* (2013.01); *C07K 7/56* (2013.01); *C12N 9/0069* (2013.01); *C12N 9/1007* (2013.01); *C12N 9/22* (2013.01); *C12N 9/88* (2013.01); *C12N 15/52* (2013.01); *C12N 15/74* (2013.01); *C12P 17/167* (2013.01)

(58) Field of Classification Search
None
See application file for complete search history.

(56) References Cited

U.S. PATENT DOCUMENTS

| 6,833,447 B1 | 12/2004 | Goldman et al. |
| 7,524,814 B2 | 4/2009 | Engelmayer et al. |
| 7,863,020 B2 | 1/2011 | Hamilton |
| 8,030,272 B2 | 10/2011 | Engelmayer et al. |

FOREIGN PATENT DOCUMENTS

WO      WO 01/83800       11/2001

OTHER PUBLICATIONS

Vollbrecht et al. (J. Antibiot (Tokyo), Aug. 2002, vol. 55, No. 8, pp. 715-721).*
Florenz, Sasse et. al., "Argyins, Immunosuppresive Cyclic Peptides from Myxobacteria", *The Journal of Antibiotics*, vol. 55, No. 6, Jun. 2002.
Rachid, Shwan et. al., "Identification of StiR, the first regulator of secondary metabolite formation in the myxobacterium *Cystobacter focus* Cb f17.1", *Journal of Biotechnology*, 121(2006) 429 441.
Rectenwald, Jürgen et. al., "Nonribosomal biosynthesis of vancomycin-type antibiotics: a heptapeptide backbone and eight peptide synthetase modules", *Database Medline (online) US National Library of Medicine*, Apr. 2002.

* cited by examiner

*Primary Examiner* — Hope Robinson
(74) *Attorney, Agent, or Firm* — Greer, Burns & Crain, Ltd.

(57) ABSTRACT

The invention provides the amino acid sequences comprised in or constituting the synthetic pathway enzymes participating in the production of Argyrins, as well as the nucleic acid sequences encoding the synthetic pathway enzymes participating in the production of Argyrins, as well as genetically manipulated microorganisms containing nucleic acid sequences encoding the synthetic pathway enzymes for the production of Argyrins, e.g. for inserting one or more of these coding sequences, mutating in a targeted manner one or more of these nucleic acid sequences, in a wild type producer micro-organism or in a heterologous micro-organism, for the production of Argyrins.

4 Claims, 3 Drawing Sheets

SEQUENCE LISTING

```
<160> NUMBER OF SEQ ID NOS: 13

<210> SEQ ID NO 1
<211> LENGTH: 55848
<212> TYPE: DNA
<213> ORGANISM: Artificial
<220> FEATURE:
<223> OTHER INFORMATION: Seq.-ID No. 1: DNA sequence comprising coding
      sequences for biosynthetic genes of Argyrins
<220> FEATURE:
<221> NAME/KEY: misc_feature
<222> LOCATION: (4)..(1608)
<223> OTHER INFORMATION: orf1: coding sequence from 1608 to 4
<220> FEATURE:
<221> NAME/KEY: misc_feature
<222> LOCATION: (3615)..(1687)
<223> OTHER INFORMATION: orf2: coding sequence from 3615 to 1687
<220> FEATURE:
<221> NAME/KEY: misc_feature
<222> LOCATION: (3661)..(5139)
<223> OTHER INFORMATION: orf3: coding sequence from 5139 to 3661
<220> FEATURE:
<221> NAME/KEY: misc_feature
<222> LOCATION: (5274)..(7388)
<223> OTHER INFORMATION: orf4: coding sequence from 7388 to 5274
<220> FEATURE:
<221> NAME/KEY: misc_feature
<222> LOCATION: (8043)..(8870)
<223> OTHER INFORMATION: orf6: coding sequence from 8870 to 8043
<220> FEATURE:
<221> NAME/KEY: misc_feature
<222> LOCATION: (8048)..(7710)
<223> OTHER INFORMATION: orf5: coding sequence from 7710 to 8048
<220> FEATURE:
<221> NAME/KEY: misc_feature
<222> LOCATION: (10282)..(9293)
<223> OTHER INFORMATION: orf7: coding sequence from 9293 to 10282
<220> FEATURE:
<221> NAME/KEY: misc_feature
<222> LOCATION: (10320)..(11057)
<223> OTHER INFORMATION: orf5: coding sequence from 11057 to 10320
```

```
<220> FEATURE:
<221> NAME/KEY: misc_feature
<222> LOCATION: (11545)..(13593)
<223> OTHER INFORMATION: arg1: coding sequence from 11545 to 13593
<220> FEATURE:
<221> NAME/KEY: misc_feature
<222> LOCATION: (13706)..(24322)
<223> OTHER INFORMATION: arg2: coding sequence from 13706 to 24322
<220> FEATURE:
<221> NAME/KEY: misc_feature
<222> LOCATION: (24361)..(42201)
<223> OTHER INFORMATION: arg3: coding sequence from 24361 to 42201
<220> FEATURE:
<221> NAME/KEY: misc_feature
<222> LOCATION: (42239)..(43249)
<223> OTHER INFORMATION: arg4: coding sequence from 42239 to 43249
<220> FEATURE:
<221> NAME/KEY: misc_feature
<222> LOCATION: (43309)..(44460)
<223> OTHER INFORMATION: arg5: coding sequence from 43309 to 44460
<220> FEATURE:
<221> NAME/KEY: misc_feature
<222> LOCATION: (45617)..(46507)
<223> OTHER INFORMATION: orf10: coding sequence from 46507 to 45617
<220> FEATURE:
<221> NAME/KEY: misc_feature
<222> LOCATION: (45620)..(44706)
<223> OTHER INFORMATION: orf9: coding sequence from 45620 to 44706
<220> FEATURE:
<221> NAME/KEY: misc_feature
<222> LOCATION: (46504)..(47244)
<223> OTHER INFORMATION: orf11: coding sequence from 47244 to 46504
<220> FEATURE:
<221> NAME/KEY: misc_feature
<222> LOCATION: (47547)..(47975)
<223> OTHER INFORMATION: orf12: coding sequence from 47547 to 47975
<220> FEATURE:
<221> NAME/KEY: misc_feature
<222> LOCATION: (48288)..(49268)
<223> OTHER INFORMATION: orf13: coding sequence from 48288 to 49268
<220> FEATURE:
<221> NAME/KEY: misc_feature
<222> LOCATION: (49483)..(55209)
<223> OTHER INFORMATION: orf14: coding sequence from 49483 to 55209
<220> FEATURE:
<221> NAME/KEY: misc_feature
<222> LOCATION: (55212)..(55565)
<223> OTHER INFORMATION: orf15: coding sequence from 55212 to 55565

<400> SEQUENCE: 1
gggggcctcg tggcccgtgc gtgccacgta ctccgtgtag ccaccgccgt actggtggat      60
gccctccggc gtcagctcca gcacccggtt ggacagcgcc gccaggaagt gccggtcgtg     120
gctcacgaag agcatcgtgc cctcgtagtt ggccagcgcc gtgatgagca tctgcttcgt     180
cgtcatgtcc aggtggttgg tgggctcgtc cagcaccagg aagttgggcg gatcgtagag     240
catctgcgcc agcaccaacc gcgccttctc tcctccggag agcaccttgc acttcttctc     300
gatctcatcg cccgagaagc cgaagcaccc cgccagcgct cgcagcgagc cctgcgaggc     360
cctcgggaac ttgtccacca gcgagtcgta gaccgtctgc tccggcttca gcagctccat     420
ggcgtgctgc gcgaagtagc ccatcttcac gctgccgccg agcgacaccg cgccatcgtc     480
cggccgcgac tcgcccgcga tcagcttgag cagcgtggac ttgcccgctc cgttcacgcc     540
catcacgcac cagcgctcgc ctcgccgcac caggaagtcc aggccgttgt agatgcggcg     600
cttgccgtag cccttcacca cccgctccag cttcgccacg tcgtcgcccg agcgtggcgc     660
ttgctcgaac tcgaacacca gcgtctgccg gcgcttcggc ggctccacct tctcgatctt     720
ctccagcttc ttcacccggc tctgcacctg ggccgcgtgc gaggcgcgcg ccttgaagcg     780
ctcgatgaac ttcagctcct tggcgagcat cgcctgctgg cgctcgtact gcgcctgctg     840
```

-continued

```
gtgcttgtcg ttcagcgccc gctgctgctc gtagaagttg tagtcgcccg agtacgtcgt      900
cagctcgccg ccgtcgatct cgatgatctt cgtcacgatg cggttcatga actcgcgatc      960
gtggctcgtc atcagcagcg cgccctcgaa gcccttgagg aacgtctcca gccagatgag     1020
cgactcgagg tccaggtggt tgctgggctc gtccagcagc atcacgtccg gacgcatcag     1080
caggatgcgc gcgagcgcca cccgcatctt ccacccgccc gacagcgccc ccacgtcccc     1140
gtccatcatc tcctcggtga acccgaggcc cgccaggatc tccctcgccc gtccctccag     1200
cgcgtacccg cccagctcct cgtagcgccc ctgcaccacg ccgaagcgct ccacgagctt     1260
ctccatctcg tccatgcgct ctggatccgc catggccgcc tcaagctgct tcagctccgc     1320
cgccacctcg dacaccggcc ccgcaccgtc catcgcctcc gccaccgccg tcttgcccgc     1380
catctcgccc acgtcctggt cgaaatagcc gatcgtcacg ccgcgatcga tggacacctg     1440
gccctcgtcc gggtgctccc gctggacgat catcttgaag agggtggact tgcccgctcc     1500
gttcggaccg accaggccta ccttctctcc cttgttgagc tgcgcagacg cctccacgaa     1560
gaggatctgc tgcccgtgct gcttgctgat gttgtcgaga cgaatcatgg gacctcagat     1620
ggggggcggga taccctcacc ccgtccctct cccaggggga gagggatgt tttcacagtg     1680
ggggagtcag gctgctccgg cggccaggtt ctgcagctcc tgccaacgcg cgtagaggcg     1740
atccacctcc gccgccgccg cgtccagatc cttctgcacc tcggccgcct tcgttccgtt     1800
ggagtagacg ctcgggtcca cgagctgcgc ttccagctcc gccttgcgcg tctccgcggc     1860
ctcgattgcc gcctccatcc cgtccagctc gcgctgatcc ttgtacgaga gtttccccgg     1920
cttgcgcgcc tgcttcggct cggccacggg cgccggctcg gccttcttcg tcgtgggcgc     1980
gggagccgcc gcggcgcgtg cctcggcctg ctccttcagc cgccggtaca tcgcgaagtt     2040
gccttcgtac cgcgtgacct tcccgtcgcc ctcgaaggcc aggatggacg tggccacctt     2100
gtccaggaag taccggtcgt gcgtcaccag cagcacgctg ccggtgaagt tcagcagcag     2160
cccctcgagg atgttcagcg tgacgatgtc cagatcgttc gtcggttcgt ccagcacgag     2220
gacgttggcg ccctccagga agagccgcgc gagcagcagt cggttgcgct cgccacccga     2280
cagcgccttc accttcatcc gctgcatggg cacggggaag agcaggtcgt ccaggtagtc     2340
gcgcagcgcc acccgttgat ctcccagctc cacccagtca tccccgcgcg gcgaggccgc     2400
ctcgtacacc gtctgctccg ggtccagcga ggcgcgcgtc tggtcgtagt acgccacctt     2460
cgtgttcttc ccgatgacca ccttgccgga gtccggcggc agctccccga gcagcacacg     2520
caggaaggtc gtcttcccca cgccgttggg tcccaccagg cccacgcgct cgccgcgctg     2580
gagcagcagg ttcacgccct tcagcacgtt ccgctcgccg taggacttgt ggacgccctc     2640
ggcctcgatg acggtgtggc ccagccgggg cgcctgcatc acctgcagtc ccgccacctt     2700
cggccgctgg aagcccttct cctccatcag cttgcgcgcc cgctcgatgc gcgccttgct     2760
cttggtgcgc cgcgcctccg ggcccttgcg cagccacgcc acttcctggg caatccagcg     2820
ctcgcgcttg tgctgggcga gggacgcgtt ctcctgggca accagcttct gctccacgta     2880
cgcctcgtag ttaccggggt acgagatgac gcctccgcca ggctggatct cgacgatgcg     2940
gtccaccagc ccgtccagga agtagcggtc gtgcgtcacc agcagcaggg agccgggcag     3000
cttgtccagc tcctcctcga gccagtccac cgtgtccgcg tccaggtggt tggtgggctc     3060
gtccagcatc agcatgtccg gccgcgtcag cagcgcgcgg gcgatggcca cccgcttgcg     3120
cagaccgccg gagagctccg ccaccggccg gtcccactcc ttcacgccca gccggtccaa     3180
cagcgtcttc gcgtggtgct ccgtgtccca gccgccgagc tgctcgatgc ggtcggacag     3240
```

-continued

```
cgccgcgagc tgctccatca gcttttcctg gccctgggcg gacgtggact ccatgcgccg   3300
ggtgagctcg gcctgcgcgg ccagcgcttc cctcagtggc ccctgagcca cgctcaactc   3360
cgaggccacc gtggcacctg gagcgaactc gggctcctgg ggcaggtagg tgacgcgtgc   3420
cccccggcgg agctgcagct cccccgcgtc cgcgcgcgcc accccgcca atatcttcat    3480 cagcgaggac ttgccggagc cgttcactcc cacgaggccc acgcgctcac cctcttcaat   3540
ggtgagcgtc aggccctgga agacggtacg gctgccgaag gagagttgga cgtcggcggc   3600
gcggagcagg gtcacggttg cctcgaatgc ggtacggagg tgctcgtcac ggctgcttct   3660
ttacagccac ttgggggcgc gaggcctctg ggaaacggcg ggcggtgccg ccggggcgga   3720
cgtagcggga cgggccgcct gggaagccgg ggcctgctgg ctggcgggac ggtcgctccg   3780
aggcggccga ccgactcct ggcctctgga gcctccggag ttgccaccgc ggccgttgcc    3840
accgcgccca ccccgccac gccgacggcg tcctccgaag ccctcgcggc gctcgccccg    3900
ggcctgctgt ccctgctgcc cttgtggcgc acggggctc tgctggggcc gggccgccgg    3960
agcgggctcg agcgctccag ccacgggagc cggctggttg gagcggtgcg gatgggcctc   4020
caccaccggc acgcgccggc ggatggtgcg ctcgatgtcc ttcaggtacg cgcgctcctc   4080
ggtgtcgcag aaggagaggg cgattcccgc ggcgcccgcc cggcccgtgc ggccgatgcg   4140
gtgcacgtac gtctcgggca cgttgggcag atcgaagttg atgacgtggg tgatgccgtc   4200
gatgtcgatg ccgcgcgccg cgatgtccgt ggccaccagc accggcagg cgccggactt    4260 gaagtccgcc agcgccgct cgcgcgcgtt ctggctcttg ttgccgtgga tgggggccgc    4320
gccgatgccc gccgtctcca gctgcttcgc cacgcggttc gcgccgtgct ggtgcgcgt    4380 gaagacgagc acccgctcga tggccttgtc cgtctgcagc aggtggacga ggaggccgcg   4440
cttctgctcc ttctccacga agtacagccg ctgatcgatg gtctccgccg tggtggccac   4500
cggagccacc tcgacccgca ccgggttctt caggatgctg ttggccaggc cctggatctc   4560
cggcggcatg gtggccgaga gaacagtgt ctgccgctgc gtgggcagct cgcgatgac    4620 gcgcttcacg tcatggatga agcccatgtc cagcatccgg tccgcctcgt cgaggacgaa   4680
tacctcgagc gccttgtagg acacgaagcc ctggtccatc agatccaaca ggcggcccgg   4740
agtggccacg aggatgtcca cgccctgctt gagggcctgc tcctgagcgt tctggcccac   4800
gccgccgaag atgacggcgc tggtgaggcc ggtgaagcgc ccgtaggcgc ggatgctgtc   4860
gccgatctgg gcagccagct cacgcgtggg gctgaggatg agcgagcgga tggggcgccc   4920
acgagcgggc ggcgtcgggc ggcccacgga gagccgctgg aggatgggca gcgtgaacgc   4980
cgccgtcttg ccggtacccg tctgagcgca gccgagcacg tccttgcccg cgagtacgtg   5040
cgggatggcc tgggcctgga tgggcgtggg ggaggtgtag ccctcggcct tcacggcgcg   5100
cagcagggac tcggcaagct tcaggtcttc aaaagtcatg gattctcgtt gtgggggtag   5160
tccccggagg gccgcgcgg gaatgagccg ccgggcccga aaaagcgaa ggcgcccccg    5220 ggggaggcgc cttccttcaa cagcctggaa ctgtcaggcc gtgcagcgcg gcattactta   5280
cgcgcggcct gctcggcggc cagcttctcc ttgtactgcg ccatcagggc ctcggcctcg   5340
ttgcgcggca ccgcgagta cttggcgaac tccatcgtga actcgccctt gcctgggtg    5400 gccgagcgga ggtccgtgga gtagccgaac atggtgttca gcggcacctc ggccaccacc   5460
gtcacgtaac cctcggccgt gctggactcg aggatggtgc cacggcgctg ttgatctga   5520 cccaccaccg agccctggaa gtcctcggga gcctggacct ccaccttcat catcggctcg   5580
```

```
aggatgatcg gcttggcggc cgcgtagccc tcgcggaagc ccatgatggc ggcggtcttg    5640
aacgcctgct cggacgagtc aaccgcgtgg aacgcgccgt cgttgatgac cacgcgcaca    5700
cccaccacgg ggaagccgat gagcgagccc ttcttgatgg cctcctggaa gcccttgtcg    5760
cacgcgggga tgaactcgcg ggggatggag ccgcccacga tgtcgtccac gaactcgtac    5820
tgctgcacgg cgtcggacgg caggggctcg acgtagccgc acacgcgcgc gaactgaccg    5880
gaaccaccgg tctgcttctt gtgcgtgtag gcgaactcgc ccttctggga gatggtctcg    5940
cggtaggcca cctgcggctt accggccacc acctcgcagt tgtactcgcg cttcatgcgc    6000
tcgatgtaga tctccaggtg cagctcaccc atgcccttga tgatcgtctg gccggactcc    6060
tcgtcacggt tcacgcggaa ggtcggatcc tccttggtga agcggttgag ggccttggag    6120
aagttggcct gggcgtcgcg gttcttcggc gccacggcga gcgagatcac cgcgtccggc    6180
acgaacatgg acgtcatcgt gtactgcacg gtgccgtcgg tgaacgtgtc gccggaggcg    6240
cactcgacgc cgaacagggc gacgatgtca ccggcacgcg cctcgttgat gtcgttcatc    6300
tcgttcgagt gcatgcgaac gagacgcggg accttgacct tcttctggtt ggcctggttg    6360
acgatgaagt caccttgct caccttgccc tggtagatgc gcatgtaggt gagctgaccg    6420
tagcggccgt cctccagctt gaacgccagg cccacgaagg gcttgtccgg gttggactcg    6480
aggatgacct tcgcctcggc gttcttctgg tccagcgcct cgttggtgat ctccgccggg    6540
ttggggaggt aggcgcagat ggcgttgagc agcagctgca cgcccttgtt cttgtaggcg    6600
gagccgcaca tgacgggcgt catcttcagc ccgatcgtgg cgcggcggat ggcgccaatg    6660
atctgctcgt tggtgatggc ggcgtcagcc aggaacagct cgcccagctc gtcgtccacc    6720
tcggcgatct tctcgatcat ctcctggcgg tcggccttgg ccttctcgac caggtcggcg    6780
gggatggcct cctcgcggat gttctcgccg ctctcaccgt cgaagtagaa ggccttcatc    6840
tggatgaggt cgaccagacc ctggaagcgg tcctcggcgc cgatcggaac ctggaggcgc    6900
acggggtggt ggctcagctt ctccttgagc tgggcggcca cgcgctcgta gttggcgccc    6960
gcgcggtcca tcttgttgac gaacgcgatg cggggaacct tgtagcgctt catctgccgg    7020
tccaccgtga tggactggga ctgaacgccg gacacggagc agaggacgag gatggcgccg    7080
tcgagcacgc gcagggagcg ctccacctcg atggtgaagt caacgtgtcc cggggtatcg    7140
atcaggttga tgttgtactc gccccacatc gcgtacgtgg cggcagactg gatcgtgatg    7200
cccttctcac gctccaggtc catcgagtcc atcttcgcgc ccacgccatc cttgccacgc    7260
acctcgtgga tctcgtggat gcggcccgta tagaagagga tgcgctcgga gagcgtcgtc    7320
ttgcccgagt cgatatgggc ggagataccg atgttacgaa ccttttcgat gggaacttgg    7380
gtggccacga gagtcggtcc ttctgctgat tgaagtcctg cgagaacagg gcaggggcg    7440 cccttacttc ccgccgcttg aagtttccag ccaaatcggc atggagccgg ggagccgtct    7500
actccctctt agccccgagg ggaagccccc ctggctgctg ggctgctgga ggtgccctgc    7560
ctacactcgc cgttcataac catgaaagtc cccgaatact tctgtcgctc cagggaatta    7620
cggaggtaga ggaaggggca tcgcccggac ggccgtccgg caggctcaag gggtggaggg    7680
gcccgctccc cctcccgagg aggatgcaca tggcgaagcc cgctggtttc gacagggaca    7740
tcggctactt gaagcccttc ctggatcggg tcgccgccgc ggccggagag ctgacggatg    7800
ccagtgcccg agaggagctg acgcgcctca tggccgagga gaaggtgcgc tgggatcgca    7860
tccagcagct gctcgagggg gccccgggac ggagcacggc gggtgggggtt tcgcccccca    7920 cgacgagtgt gggcccgcgc cccccgccc gggcgcagga gctggcccgc gcccgcgcgg    7980
```

```
atggaatcaa ccgggtggcg ccgcgcgcgg cggggctcac cgtgggcagc ttgaagcgga   8040
agtcatgaag tcgtgacacg cgcgggggc agtgcgaaac gcagccctc ggagatttcg    8100
gtgtcggtga ggagccggaa ggtgccctcg ggcacgtcca gctccacccc acccaccgcc  8160
tcgcggtgca gggcgcgcac cggcaaccc accgccccca gcatccgctt cacctggtgg   8220
ttgcggccct cggtgacggt cacctccacg gtgtgcgcat cacgcagccg gaccttcgcg  8280
ggccgggccg ggccgtcctc caattgcacg ccgtggcgca acggctccac cttcgcttcg  8340
tccgcctcgc tgaacaccgt ggccacgtag cgcttggtga ggtgcgtctc gggcgacgtc  8400
acgtgcgtga cgagcttgtc atcattggtg aagaggagca gcccggtggt gccccggtcc  8460
agccggccca ccgcgtgcca ggtgaagccg gccagctccg gcggcagctg gggcaggagc  8520
acctcgtaga cggtgcccac cccgtgctgg cccaccgtgg aggtgagcag ctccgccggc  8580
ttgtggaagg ccagcacccg tgtgggcgcc tcgagcgaga cgggcactcc gtccaggcgc  8640
aggctggctt ccggggcac cggggcgagg gggtgcttca ccaccttgcc gttcaccgtg   8700
acacggccgg cctggatggc gtcctccgcc tcttcctgcg gcagcacccc ggcccgcgcg  8760
agcgcgcgta atagccaatc cggtttggcc ttgccctccc atcgcccggg gtgggcgtgc  8820
ttggaagggg agggcgaggg ccggcgggga ggaggtggct tgcggggcat gctccgagcc  8880
actgtaacgg ccacgagtca gtgccgcgag ggttcgtcga acgcaccacc ctcggccgag  8940
ccgggcgtcg ggccgggctc accctggggc atccgccgct cctcacgctc ggtgccctcg  9000
gcggcgttgg gcgtgcgctt gggaccgttc tccttctccg cgggagcctc tcgatggggg  9060
cgcttctccg gggtgtcttc cgccgcgtcg ctgacgtca tccgctcgta gggcatgtgc   9120
cacatggttt cgctccttcc agtgtggaaa cttcaaagaa ggtagggacc tggagcgcac  9180
atcactcgga acgcttccag gtcgcccgct ggatggccgg ggggaggaga gcgcttgcgg  9240
ctgaatgctc gctcgcccag gctccccggc cccttcctg gaggaccca tggtgcgttc    9300
catcctgttg cttacccttc tcgccctgcc ggcgctcgcc gccgaaccgg ttcccgctcc  9360
ggcgccgcct cccaagcggc ccgtccacac ctattccatc gtcgcgagag atcccgagac  9420
gggtgagctg ggcgtggcgg tgcagtcgca ctggttctcg gtggggggcga cggtgccctg  9480
ggcggaggcg ggcgtgggcg cggtggccac ccagtccttc gtggatccgt cctacgggaa  9540
gctcggtctg gagttgatga gggtgggccg cggcgccccc gaggcactcg ccgggttgct  9600
ggccgcggac tccgcgagcc aggtgcggca ggtggcgatg atcgacgcga agggccgggt  9660
ggcggcgcac acgggagaca agtgcgtcgc ggccgcgggc acatcgtgg gcgagaactt   9720
ctcggtacag gccaacatga tggagaagga caccgtgtgg ccggcgatgg ccaaggcctt  9780
ccgggagacg aagggcgacc tggccgagcg gatgctggcg gcgctcgagg cggcggaggc  9840
gcagggcgga gacatccggg gcaagcagtc ggcgggggctc atcgtggtgt cgggcaaggc  9900
ctcgggacgt ccctggatgg accgcaagtt cgacctgcga gtggatgacc accccgtgcc  9960
gctgaaggag ctgcgccggc tggtgacgct gcagcgtgcc tacaatctaa tgaacgaggg  10020
agacctggcc atcgagcgca acgacacgga ggggcgctg aaggcctact cggcggcgga   10080
ggcgctggtg ccggggaacg cggagatggt gttctggcac gcgtgtcgc tcgtcaacgt   10140
ggggaaggtg gacgaggcgc tgccactcct ccagaagacg tacaaggtgg acgcacgctg  10200
gaaggaactg ctcaagaggc tgccgaagtc ggggttgctg ccggaggatc cgaagctgat  10260
gaaccggctg ttggggcgct gagccacccct ctccctctgg gagagggccg gggtgagggt  10320
```

```
catccccccc tgttccccga gcgcagccgc ttggccaacg tgtgcagggc ggcgagccac    10380
agcttcgcct ccttgcgagt gagccgggag cggcgcagcg gagcgaacaa gtcccggagc    10440
ccggtgcgcc cgcgggagtc ctcatccacg aggaaaccac cggccacgag cgcgtcctcc    10500
agagcggact ccacgagggt cagctcggtg tcggtggcgg ccacggggag cggagcggcc    10560
ggaggaggcg aggcggccag ggtggccatg cggatttcgt aggcgtacag cagcacggcc    10620
tgggcgaggt tgatggaggg ctgctcgggc gcggtgggca cggcggacag gtcgtgacag    10680
cgctcgacct cggcgttggt gagcccgctg cgctcgtcgc cgaagacgag ggccacgggc    10740
ccctgggtgg cgcgctgcac catctcctcc gccacggccc ggggagacag ccgccgtttg    10800
ccctccacct tgcgtgagct ggtgcccacc acccacacac agtccgccac ggcggcatcg    10860
agcgagtccg cgcggcccga ggcctccagc acatcctcgg cgtggacggc gagtcggcgc    10920
gcgggagcga ggtcctcggc ctcggggtgg acccaggtcc actcagacaa cccgcagttc    10980
ttcatggccc gggcggcggc acccaggttc tccgcgttac gcggacgtag caacaccagc    11040
cggatgggca gaggcatcac accgaatcct ttcagctctc accctcgaa ctcagggac    11100
attcacagat gcactcgcgt caaatgtctc tcttttgag aatatcgtac tttctggatc    11160
gcgatgtgtg gggcggcgct gtgatgtcta ccgtccggta ggtagctttg cctccggtgt    11220
gctgtcgcca gtgattccat tgaggatgtg tatcgatgat gttgccgttc aagaacggta    11280
catccatccg agaagattcc ctcttcgaat ctagtcgtgc tgtcttttt tgcgattgtc    11340
tcttgcccta ctgctctgtc tggtctaagt gagggtacct atggggcacc cctcctgtca    11400
gggctcaagc gcgagcctgc aagtgggtgc cttacgtgcg gcaaatggg ggggacttcg    11460
gatgaaggtt gtcgcactgc cccataagtc ccactccagt agctacgaag tcgcagtgcg    11520
cggaatccag ggatctctca ccggatttgt tgctcacgat acgcgtcccg ggcttttctg    11580
atgggccaga ccgacctact cctgctgaac gcatccaatc ttccgcagct cccgatctat    11640
ccgtatgcct tcgtgcaggt tagcgcgatc gctcgtcggt ttggcctttc tgtgcggagg    11700
ctcgatctat tgcaggtgcg ccgcgagttc tggaggccca tgctgcggga gctcatccaa    11760
cggcatcggc cccggatggt gggtatccat ctgcgccagc aggatacggt gcttcatttc    11820
gactatcaca acccacagat ggggtgatg gcggggcgct atttcccggt gcaggacacg    11880
cgggcactga ttgaggtgct tcgtgaggtg gcgacatgc ccatcaccat gggaggattc    11940
gggttcacgt cccatgccca tctcctgctc gattatctcg gggctgactt cggggtgcag    12000
ggagatccgg atggattctt cgcccgcttc gaggacgtcg tcgcgagacg cgatctggaa    12060
tcggttccag ggctggccta tcgccgcgat ggcacctatc agttcaatcc gcgagggttc    12120
tatcctccgg cggcggagcg cgagtatacg gacgagatcg tcgatgagct gatctccttc    12180
tatggacatg ctcagctcta cggttccaac ccgccaacgg tggccgtgga ggccatgcgc    12240
ggctgcccgt tcagttgcgg tttctgtctg gagcccacg tcaagggacg ccgcatcgcg    12300
taccgcgaca tcgaaaccat cgtgagcgag ctggagttcc ttctcagccg caacctgcgc    12360
cggttctggt tcgttgcctc cgagctcaac atccaggggt cggaattcat cttgaagctc    12420
gccgagcgcg tcatccggct caacgagacc catcccggca gccgatcga atggtccggt    12480
ttcaccctgc cacgattcaa cgagtcggat ctccggctcc tgcagcgcgc gggctacgcg    12540
ggtgctctca atgacatcct ctcgctcgat gacgaaaacc tgcaccggat gcgggttccc    12600
taccgctcgg gtcaggccat cacctatctg aaggccatgg ccaagatggc cgaggaggag    12660
agccaggcac aggccacgag tccccacggg gtggaggggc tgcgccagcg gctggcgggc    12720
```

```
tatttcaccc tgttcctggg caactcccac gccgacgagc ggaccatccg ccgctcgctc   12780
cagcaggtcg acgagcacgg cctacgcgag aagtaccgcg gggcgttcgt gatggccgcg   12840
actcgggtct acgacatcga gggcaagtac atctgcgcca cgagcgagga agaggcgaag   12900
agcatcatct cgtacgacga gcgtggtgag cgcccgttca acctgctgtg gccgtccttc   12960
tactaccctc ggttcctgat gcagcggctc ggctccacgg cggagatcct caagttcttc   13020
tcgttcgttg gagacacctt cctgtcgctc gctcatcgca tgcgcaagga ttggaactgg   13080
ttcttgtcgc ggaacacgag cgtggaacaa cttcgcgagt ggctcgccgg agcctcctcg   13140
gtgcccctcg gagcccacga ggcgccgccg catgtcctcg agaaggcggc gcacgtcctc   13200
ggagagcccc ggacgcccgc gctcgtgtcg atgatggccc cggaacccga gcagaagccc   13260
ctctggaacg aggtcgccag ggttctgctc gagcacctct tccgggtgca cggcaagtca   13320
gtggcggcgg tgaccacgca tctggggatt caggcggatg agcgtggaat tccgcgattg   13380 tcggaataccc ggctcatgga gcggctgtac caacgctacg attcagtgga gcaactcatc   13440
gaggaggcag gatcttgcct cgatgtgaca ggcgattcgc tggcgatgct ctatctgcaa   13500
tggctgctct atgccaacaa cgtcacgatt cgtcccgaat accgcgaatt gctcttcgag   13560
ccgccggtcg agcctgcttc agcggttggc tagggcatag gcagtcgtac gtctgatgag   13620 agggccaca cggatggctt ctccgtgatt ttttcatcct cgagttccga cggtggccgt   13680
atggccgcgg agcttcgaga aagaatgag ccgttgcgaa cagcggcttc gagatagaac   13740
gaaaatggat acgcgcaagc aggcctctgg cgaggtgtgt ttcctcgacc tctttctgcg   13800
tcaagcggag cttcatccgt cgaagtccgc ggtcgaatgc ggctcggccc ggctcaccta   13860
tcaggcgctt gtcgccagga gtgaacggct cgcatccgcg ctgggggcga gcggcgttca   13920 tccagggat cgcgttgccg tcgtcctgca tcggggactc gacaccgtgg tcgcgatggt   13980
cgccgtgctt cggaccggtg ccgtctatgt gccgattgac gtcacctggc ccgacaaccg   14040
tatccgttac atcctcgatg acctgcagcc gggcgcgatc ctgtgtgacg aggagaactc   14100
gcggcgcgct tgcttcacga gtgatgaccg gctccttctg gcctcctccg aggggacagg   14160
gggctcggat ttcaggcctg gcccgatggc gcccgcctac ttcatgtaca cctcgggctc   14220
aacggggcga cccaagggcg tggtgctcgc tcatggcggt ctggcgagcc ggctgcatgc   14280
gttctctcgc gcatatgaga tccaacccga ggaccgcttt tcgcccctga gctcggtctc   14340
cttcgacgtg tcggtcctcg acctgatgct tcccctcgtc aatggatgct gcaccttcat   14400
tgcgtcggat gagcagcggc gcgatccgga tgcgctgcgg aacctgttcg aggagcgggc   14460
gctgaatgtc gctttcgcca cgcccaccac gatgcgcgcc ctcgtctccg tgggatggaa   14520
ggggagtccc cgcaccaaga tcctctgcgg tggtgaggcg ataccccagt cgctgatgaa   14580
cgaactcgtc gcccgggggc ggttgttcaa cgtctatgga ccgacggaag ccaccgtcgc   14640
ggtcacttcg ccagagctct tcgcgggtga cagtgtgcac ctgggccgcg cgcttccggg   14700
ggtggagttg ctcgtcctgg acgaggccgg agcgatctgt ggaccccggc agccaggaga   14760
gctcgtcatc ggcgggatcg gtgtggcgct ggggtattgg aagaatgacg agctcacccg   14820
gaagaagttc gtcgacggga agtaccggac gggcgatctc gtgagctggg gagaggacgg   14880
caatctctac taccacggtc gcatggatga gcaggtcaag ctccacggtc accgcatcga   14940
gttgctggag atcgaggaga tggcccgctc gttggggctc gtccgtgaca tcaaggtcct   15000
gattcaggag aacgcggcat cccctcggct cgtggccttc ttcatcggtg acgaggcagc   15060
```

```
cgcacaatcg ctgcggagga ggctggccag cgagcttcct gcctacatgg tgccgtcggt    15120
gtgggtcggg gtcgagggct ttccccagac gtcgaccggc aagctcgacc ggaaggcgct    15180
cctggcgaag gtcgacgagc gcgccgaggg gctcgacagt cctccggaag cggctccgtc    15240
cggcggtcgc gaggcgactc tgcttggtat ctggcgggag gtattgcagc ggccggatct    15300
gtccccggac gatgatttct tcgcgagtgg tggggattcg attctggcga tgcgcaccct    15360
gagccgggca cgcgaagcgg gaatcaacta ccgggcggtt catatcttcc agcacccgac    15420
ggtgcggagt ctgctggaga ccgtcgttca ggcgcacgaa gggcccaggc ccgaactgcc    15480
cgagttgacc acctcgggtc tgacgcccgt ccagagatgg ttcttcgagc agccgctggt    15540
caaccggggg ttctggaatc agagcattct gctccggctg acgcgcccga tggagctgcg    15600
agagctccgg gagatcgcgg actgcttgac ccggacgcat cagatcctgg cttgcgagat    15660
cgatgaaaag ggaatgcgac tgggctccag ggacgccgac gcatgctgcg cccaggtgtc    15720
cctgaccacg ggaagcggga cgtcatcccc agaatttgcc cggatcatcg acgatgcgca    15780
ccggagcctg cgccctgagg agggaaggct gcatcgcctg gtcctgatcg aatccagggg    15840
ttctggcgag tggtacctgt tctggacgat tcaccacctg gtcatcgacg gtgtgtcgtg    15900
gcggatcctc ttgagtgacc tggggaccct tctccagcag aaggccagcg agacgcgct    15960 ccatctggag aaggcccccg tgagcttcct gcattgcagt gagcgtatgc gggcgctcca    16020
cgggaaggtg cgggaggcag agctttcgta ctggaggaag ctccccgagg cgccgttgcc    16080
ctggagctcc gaagtgcggc aggaggtgcc cgaagcggcg cggaccgagc tcgtgctctc    16140
gctctcacag gaggcgacac gcggcctgct ccaggatgtg ctggccggta cggggaaggg    16200
catcaacgat gtcctgctct ccgcgctgct ccaggccgtg tatgacgtgt ctggagagag    16260
acgcctgtca ctgtggctcg aggggcacgg gcgcgaagaa ggtctgctcg aattggatac    16320
gtccaggacg gtgggctggt tcacgtccat gttccctgtc tacctggaga gcccctcgcc    16380
ggaggacttc cagtccacgc tcgaggcgac acgcgcgtcc ctcggcgcga tgccgaaccg    16440
tggcgttggc tacggcatcg tgcgctacct gggagaggat gcgcgcggag aaggccttcg    16500
taccggcaat gagccgcgca tcagcttcaa ctatctgggc caatgggacg acgtcgccag    16560
cgaccatttc tcggtcgtga gcgaacccgg cctcgatgac atcgcgcccg agaacaagtg    16620
gcatcgagag gtggacatca actgcctcgt cgcccagggg atatttaagg tccacctgac    16680
attcgtgcgg cggctccagg acaaggagaa gctcgagagt ctgctgcgtc gcttcatcgc    16740
gcgcctggaa agcgccatcg acgcctacaa gggcgccggc gagttccggc ggaagttccc    16800
cctcctgtcg attcctcccg aggccttcgc ccgcaacggc atcgatctcc aatccgtgca    16860
agatgcctac ccgctgacgc ccatgcagga aggcatgctg ctgcgtgccc tgacggtgcc    16920
ggagagcggc aactatatcg ttcgtacctt cttcgaccte acgggagagc tccatcccga    16980
cgcctggcgg gaggcgtggc gacgggagtt ggccgagcag gaactgctgc gctccgcgtt    17040
cttctgggag cattcaccga ccccttcca ggtcgtcttc tctcacgtcg acctcgattg    17100
gcggacgcac gactggggcc acctcggccc ggaggagcag cagcaggcgt tctcgaagct    17160
ggagaaggct cgtcatgccg agggattctc cctgagcaag gcgcctctgc ttcggatcga    17220
tttcatcgcc aggggcggca gtgattacag gctcctcctg agcttccacc atttgattct    17280
cgatggctgg agtctccagg tcctcctgga gcgggtgctg aagcggtatg gcaggcgcg    17340 aggtggcggg gaagaacggc tgactccagc atttcgtttc cgcgattacg tcgcctggaa    17400
ccgcaaccac gagtcttctg atgccctgcg gttctggcgc gagcatctcg aggggtcga    17460
```

```
ggagccgacc ctgctgggtg acgagcaggg cacccggcac gagtacgcgg aaacggtact    17520
acgtctggaa gaggcccggt ggtctgggct cggtgcccgg tgccggcggc aggggatgac    17580
caagagcagc ctgattcagg ctgtgtggtg ctgggtggcg aagtcctacg ggcggaagag    17640
ccatgtggtc tatggcttga ctcaagcagg ccgggccgcg gccatcggcg atatcgaaaa    17700
cggcgtgggc ctgttcatca ccacgagccc ggtcgcggtg gacctggaca agcattccaa    17760
gctgtccacg gtgggaagat tcatccagca ggtcaacgcc caggccctac accatgaccg    17820
gctccccctg agtgagatcc agcgcatctc ggggcgcgag atcggacaac cgctattcga    17880
ttgcctgttg gtattcgagc aggagccgat ccccgaactc gcgggaggcg tgagcggcgg    17940
cctgtcggtg gccggtactc ggacgtatga gtcaacggag taccctctga ccctgagcat    18000
cctggagaag agggatggga gctgcgatct ccgcttctat ttcaacaaga gaacttcag    18060 tgagttcagg gtagaaggac tccggcttct gttcgaggaa atccttgccg cgtgggaaag    18120
agagcaggaa ctcgagctct cttccctgcc tgccttcccg agccgggatg gcgcgcttct    18180
ctcgcggtgg aacgcgaccg ggtcggacta cccggcccaa tccctgacgg agctcttcct    18240
gcagcaggcc cggcgtaccc ccaaccaccg tgccgtgcga tacggcgagc gcgagctatc    18300
gtacgcggaa ttggccgagc ggacggggac cctggcccgg cgcctggagg cgctcggagt    18360
ccgcccggga accccgtggc ggtgcacat gcatcgcagc ctcgagatgg tcatcgcgct    18420
acacgcgatt gttcgagcgg gtggcgccta tgtgccgatc gatccggagt atccggcggc    18480 gcggtgcgg acgatcctgg aggatgtggc ggcacccgtc gtcatcttcc acgacgcggc    18540
tcccttgaag tgccaggtgg gtggcaccgt tttggatgtc acccgattg tcgaggaggg    18600 tcatggcggg gcggaccacc gcgccgcgga gtatgacccc gagcggttga tgtacatcat    18660
ctacacctcg ggctccacgg gacggcccaa gggcgtcaag tgtagacacg aggggccgt    18720 caaccggatc tgctggatgc agcgaagcta cccgttgtca tccgacgacg tggtcctgca    18780 gaagacccg tacacgttcg acgtttctgt ctgggaattc ttctggcctc tggcggtggg    18840
cgccagcctc gtggtcgcgg caccgggcgt gcaccaggac gcgagcgccc tggctgctct    18900
gatcgagcgc gaaggtgtca cacacctgca cttcgtgccc tccatgctgg atgtgttcct    18960
cgcgagcaag gggggcgctc gctgtgcctc cttgcgccgt gtcttctgca gcggagaggc    19020
attgccctcg ccggtggtca aggagttctt ccgctccgtg ccacatgcgg agctgcacaa    19080
tctctatggg ccgaccgagg cctccatcga cgtgacggcg tgggactgtc ggtccgacag    19140
tccggtggcc tcgattccca tcggctacgc gatccagaac gtgcggctcc atgtgttgga    19200
tgagaagcag gctcccgtgc cccacggtgt tccgggcgag ctctgcatcg cgggaatcgc    19260
cctggccgaa ggctatgtga accggccgga ggagacggca agcgcttcg tccagtcctc    19320 gtgggatgcg cgggagcgcc tctatcgcac gggcgatctg gcccgttacc tccccaatgg    19380
agccatcgaa tacctggggc gactggatca gcaggtcaag ctgcgagggt gcggatcga    19440 gctcgatgag gtctcgagcg tgctcttgcg cgatgcccgg gtgcggcagg ccgtggtccg    19500
cgtcgtcgcg gtcccgcgg ggcaacccgt gctggccgcc tacgtcgttg ctcacgaagg    19560
ctcggccgga acgttggagg aggcactgaa ggcgagctc gagcgctccc tgccgaggta    19620
catggtgccg gagttcttct tcttcctgga ggcgctcccg gtcaatcgca atggcaagct    19680
ggatgccgat gctctgccca ggcccggggc ctcttcctct cgggagtggg agccgcccca    19740
gaccgaggtc gagaaggatc tcgccgcgat ctggcagcgg gtgctgggtg tcgagagggt    19800
```

-continued

```
agggaggaac gacagcttct tcgccctggg gggcgattcg atcctgagca tccggatcct    19860
ggcgctcgcg aaggagcgcg gatgggacgt gagcctcggg gagttgttcc ggtctccgcg    19920
gttgagcgac ttcgccagga ccgcgaaggc ggcggcgcac acgcccgtgc tcgcgcgctc    19980
cgccttcagt ctgatcagcg ctcgtgaccg ggccgcgatg ccggcaagcg tggtggatgc    20040
cctccccatc gcggccctgc aagcgggaat gctcttccac acgaagctcg cggaggaagg    20100
tgtcatgtac cgcgacagct tcctctacgt cattggtggg gagttcaacg agcaggcgtt    20160
ccggcaggcg ttgaaggagt tggtgcatcg ccacccgatg ctccgcacca gtttcgagct    20220
cggtgcatac tccgagcccc tgcaacgggt ggagcgggaa gtggagttgc cgctgcggct    20280
cgaggactgg cgtgacagcc aggatcagga gcagcgtctg tcggcgtggc atgagagcta    20340
ccgcccgacg ttcgacatca ctcgagcgcc gctgttcaag atggaggtca agctcctgag    20400
cggtgccagg ttcgccctgg gtctctgctt ccaccatgca atcctggatg ggtggagcat    20460
cgcgtcgatg atgacggagc tgctcctgga ctaccagcgc ctgctgacgg gtcgtgggcg    20520
ggcgatcgag ccgctggggt ctggatacgc tgactatctg gagctggaga agcgtgtcgt    20580
cgaggatccc cagcagaagg ccttctggtc cacgtacctg aatgacgccc agtcgttgag    20640
gttgcccgtc aagcaggagg tggagcatcg gaatcggcgt ggaacgagtg tccacggccg    20700
gttcgacatt cccgaggagc tcgtcgggca gctggagcgg atcgccaggt ccctggagat    20760
caccaagagg catctgttcc tcgcggccca tttccgcgtc ctcgcgatga tctgcgggca    20820
taaggacatc gtctccgggg tcgttacgaa cggaagacca gagacggtgg acgctgaacg    20880
gatcgtcggg ttgttcctca atgcgccccc gatgcgcttg acgctcgggg gtggaagctg    20940
gcgccagctg atccaggcca tcgtcgagga ggagcggaac atccttcccc acagaaggta    21000
tccggtctcc gagatgaaac ggcattgtgt ccaggccgac ctcttcgacg tggcgttcaa    21060
ctatgtggac ttccacgtct attcgcgggc gggcgagctg gcgtcggtgg catccagac    21120 gctcaaggcg aaggaggtga cgaacttcgg gctgtacgtc accttctacc agggctggcc    21180
gtacagcaat cagttcacgc tggcgtatga tccggatctc ttcgaccggg agcaggtcga    21240
tcaattcgcc cggtattatc tggcggcgct gcgtgcgatg gcgcagtcgc tcagggcag    21300 gtatgagctg tcattgctca cgcccgagga gcggtccgcg ctcctgatct ccggtgagcc    21360
acctgcctcc aagccggccc tggtggagaa gatctggagc aatgcccgtg ctcatccgga    21420
gcggcaggca ctcacggatg ggtcgcggtc cctcagctac cgggaactcg cgtcactcag    21480
cgactcgttg gctcgtgcgc tccatcaggc ggaggtgaaa cccggcgata tcgtcgcggt    21540
gaacctccgc agggacgtcc atctgccggt cgcgctcctg ggcgtgatgc gcgcgggggc    21600
cacctacctg ccgctcgaca atcgcttccc gctcgaacgg caggcgttca tgttgcagga    21660
cagcggcgcg aagctggtgc tctgtgacaa tgagacgcgc cccgcctcgg gcggaacggc    21720
ccggctcttc aatctggacg aggagaagtg gcaggaccac ggcggcgagc ggccgcttcc    21780
agagctccac gcggagtcga tcgcgtacct gatctataca tctggctcca cgggcaagcc    21840
caagggcgtg ctcatccgcc accggaatct cgacaacttc atcgcgagca tggagaggtc    21900
tcccggtttc tccagggcg accggctgct cgcggtcacg acggtggcgt tcgacatcgc    21960
ggcgctcgag ctgttcctgc cactctcttg tggcggtcag gtcgttctcg cgccagagca    22020
ggtcggcaag gatgccacgc tgttgatgga gtggttgaag cggcacgaca tcacggtcat    22080
gcaggccact ccagccacgt ggcagcagtt cgtcgacctg gatggcgggg caaaccaga    22140 cctgaagatc ctcgttggtg gtgaggctct gccccggca ctcgcccgtg ggctcttgac    22200
```

```
ccgctgccgt gagctgtgga acatgtatgg gcccaccgag accacggtgt ggtccagctg   22260
catgcggatc gcggacagca cccgtatccg gatcggccag ccgatcgcgg acacccggct   22320
ctatgtcctg gatgcctatg gaaacccggc tccccggcag accgtgggcg agctgtacat   22380
cgcgggcgga ggtgttgccg cgggctactg gcggcggccg gatctgaccc gtgagcgctt   22440
ccaggatgac cccttcttcg ggggtccgat gtatcggacc ggcgatctgg cgaggatcga   22500
ttcgcgcaac gaagtcgagt gcctggggcg tacggaccac caggtgaagc tgcgggtta   22560 tcgcatcgag ctcggcgaga tcgatgcggc catccaggag cacccggacg tcagtcagtc   22620
cgccgtgatt ctccggaggc actcggaacg tggtgatgag ctggccggct actacaccct   22680
gcacgatgaa gcgctctcca ggcgggcgaa tgagctctat ggagagcagg tcgtccgctg   22740
ggaggccgtc tggtcggaga cctatggccg gtcgaaggag aaccggggcg cgttgaatct   22800
ggcgggttgg aacagcagct acacgggtca acccatgccc gaagcggaga tgcgggagtg   22860
gattgacgag acggtcgcac ggattcgctc actcggcgcg aagcggatac tcgagattgg   22920
ttgcggtacg ggtctcctgc tggcccgtct ggcccccat tgcgagcggt acaccgccac   22980
cgacttctct ccggccgcgc tggagtatgt ccagagcgcc atcgtccctc agctctctca   23040
cctggactgt gaggtgcaac tggtccgcgc cacggccgac aggttggagg gggtggagga   23100
tgggcagttc gatctggtca tcctgaactc ggtggttcag tacttcccga ccgggagta   23160 cctcgacaag gtgctcgcgg cggcgatccg gaagacccgg cagccgggta ggatcttcgt   23220
gggtgatgtc aggcatttcg gcctggggcg cgcgttccat gcctccatcg ccgactacca   23280
gtccaaggga gcactggctc cggcggccct ggaggagaag gtcgcgcagg gcctgcggaa   23340
ggagacggag ctcctgttgt cgccgcgcta cttcctctcc ctgtcctctc tgggcgtcgc   23400
ccatgcggag atcgagctca gcgggggac gcaccacaat gagttgaccc ggttccgcta   23460
tgacgcggtg ctgtccattg gccagcgtcc ggagcagctc gagacccgct ggtacgagtg   23520
ggaaacccat cctctttccg gggatgagct ctcgacgaag ttgaagcagg cgggtgagtg   23580 cttttggactc cgagccgtcg gcaacgcgcg gctggcgaga gagcgtgagc tgctggggc   23640 tcggagtgac gagacccagg gctcagcggg agctggcgcg ggactcgatc cggagcagct   23700
ctaccggctg gcggaggctc atgggtacag ggccaagacg agctgggcct cggagcacgc   23760
ctatggcgcg ttcgatgtgg ccttcatccc ggccggaaag aacgccacgc ccctgttcga   23820
gctggcgcaa ggctcggcac gtttgagcaa tgcccccttg ctctcacaga ttgatgtccg   23880
ggtgggcgcg gagatccggc gggccctcca gaagaacctc ccggagtaca tggtccccgc   23940
gcggctcgtt ctcctggatt cgatgccgca cacgcccaat ggcaaggtgg accggagcag   24000
gttgccggat gtgggcgca acgccgtctc ctccgagttc gtcgagcctc ggaacgagaa   24060
cgagcgcaag ctctgccaga tgtggcagga gttgctgggc ctggagcgcg tgggcgtgag   24120
ggacgacttc ttcgccctgg gcggccactc gctgctcgcc acacagctga tcacacgtat   24180
caacaaacag ttcgagtgca atctcagcct gcgggccctc ttcgatttcc cgacgatcga   24240
gcagctcgtc cggagagatt gagcggagcg gacgctccag ggcccgcca tgccgaagat   24300 tcagcgccgc aagaagaatt agagaatccg ccaacaccgg aacagttgag agatcgagcc   24360
atgcatctcc ccgagcttct tccttttgtcg tttgctcaga cccggttgtg gttcctcgag   24420
cagttgttcc ctgccgggc cacgtaccac atccccagt tctggcgtct gcggggggg   24480 gtgaacgtga gtgccctggt gaaggccttg aagaacacgg cggcgcgtca cgagtccctc   24540
```

```
cggaccacgt tcgtcaccga gaacggtgag ccgaggcagg ccatccacga ggacatggcg   24600
ctggacttcg agtgtgagac gctgatgag cgagggggag agacgctcga ctcctatctc   24660
tcggcgttga cggcgcggac attcagcgtc tccgaggggc cgctatggcg tgtgcggctg   24720
gtgcggacga cgcgctcgtga acaggtgttg gccgtcgtct tccaccacat catctgcgat   24780
gggtggtcga tggggatctt cagccgggag gtcagccatc attacaacca ggccatcggc   24840
gaaagcttgg gtgagctgag tgagcctccc attcaattcg gagacttcgc ccagtggcag   24900
cgggagtggt tgcagggcga gcgtctggag cttcagctgt cgtactgggc ggagaaattg   24960
aagggtgccc ctgacctgct cgcgttgcca acggacttct cgcggcctcc agcggcgagc   25020
aacaagggca agctctacgg gacattcgtt ccccccagagg tcgtgcagcg cctgaaggac   25080
ctggcccggc aggagaaggc caccctgttc atggtgctca tggctgcctt caaggtgctt   25140
ctccgccggt attcgggctc ggatgacatc gtcgtgggaa cgccgattgc caaccggcat   25200
tatcccgatg tcgaggaggt gttcgggtac ttcgcgaaca ccctggccct tcgcaccccg   25260
ctggagggca gcgcgagctt caggcaggtg ctgcagcggg tgaagcactc gacgctcgag   25320
gcgtatgagc atcaggacct tccccctcgag ctcgtcgtcg acaagctggg cgtggagcgg   25380
gacctgagca ggcatcccgt gttccaggtg atgttcgctc tcctgaccga aggccgctcg   25440
accctgggtg ttggcaagac ggagcttcgc ctcgaaggac tggaggtgga gagcctgcgg   25500
ggcgtcggtg attgtgccaa gttcgacctg gcgctgctcg ccgaggagac agagcagggt   25560
ctgttcctcg agttcgagta ttcgaccgac ctcttcgaac aggcgaccat cgagcgggtt   25620
gcccgccact tccagaacct cctcgtggag gtggtcgccg ggccgggatc gtcgatcgat   25680
gactacttcg tcctgagtga tgcggaaatc gccgagcgga tcgcctgtct ggatggatat   25740
ggactccccc acgacaccga gatctgtctg catcagtggg tggagcgctt cgcggcacga   25800
acgcctcagg cgatcgccct ccgggatcag acggggtcga tgacctaccg ggagttgaac   25860
gaggaggcga accggctggc gcgctgtctg ctcgagcgtg gtctgggcca tggacagatt   25920
gtcgggctcg ccctccctcg gacgagggag ctcatcgtcg cgatggtcgc ggccttgaag   25980
gcacgagcgg cctatcttcc gctggacctc ggctatccga gccagcgtct gcgcttcatc   26040
ctggaggacg cggagaccgc cgcggtcctc accacccggg cgcatgtcga gtccctgcgg   26100
gggcactgca agcacatcat cgccctggag gatgtggcgg cggaggtcgc tggccagtcc   26160
gcggggaacc tggacctgga ttacgcgtcc ggggatctgg cgtacctgat ctacacctcg   26220
ggctccacgg gcaagcccaa gggcgccacg atctgccacc gcaatgtgac gcggctcttt   26280
cccgatccgg aacctctcta ccggttccgc ccggatgatt gctggacgtt cttccactcg   26340
tgcgcgttcg atctctctgt ctgggagatc tggggcgcgt tgagccacgg ctccacgctc   26400
tccgtggtgc cagccgaggt ggctcgatcg accgacgagt tccgcgagtg gctggtcgcg   26460 catcggggtta cggtcctcaa ccagacgccc tctgcctacg agcagcttct ctcgtatatc   26520
agcagggagg gcgggagcga cgggctgcgg ctgcacaccg tgatgcttgg cggcgagggg   26580
tggggagagg ccttggcgga gcgccatcgc cagctcctac cgcatgtctc cctttacaac   26640
gagtacggtc cggcggagtg cgccgtctgg acgacacacg gctgcgtcta tgatgcgag   26700 acggtgcagt cgtatccgct ggatctgggg atcgcgcaca gccagagtct ggccctcatc   26760
ctgaacgatg tcatcgtgt taccccgacg ggcgtcgtgg gcgagctcta cctcggcggt   26820
gagggtgtca cccaggggta ttggaagcgg ccagagctga acaaggagaa gttcgtccac   26880
gtctcccttc ccggaaaggg caacgtccgc ctctacaaga cgggcgatct cggaaggtac   26940
```

```
aagagcaacg gacgtatcga attcatcggc cggcgcgatc accaggtgaa ggtgagaggc   27000
taccggatcg agctgggtga gattgagagc atcctccgga gccttccggg tgtccgggat   27060
gcgctcgtca tgttgagcga gagcggccgt cagctcgtgg cctacgtcgt ggtgggtgag   27120
ggcgggacgc tcacgcagga gacgatcgcg taccagctca aggatgcgct gccagcctac   27180
atggtgcctt ccttcttcgt gctcctggag cgcttcccga tgacgaataa cgggaaggtg   27240
gatcgggccg ccctccccaa gccccacgcg acgacaggtc agtcggttgg ggctcaggcc   27300
ttcgtcgcac ccagcgggcc actcgaggaa ggtatcgcca gtgtgttctc cgagctgctg   27360
gcgatcaccc ccttctccgc ggagggcaat ttcttctcgt tgggtgggca ctcgctgctc   27420
gccacacagg cggcggcgaa gatccatcag cgtctgggca tcgcgtgccc ggtgcgtacc   27480
ttgttcgaga gcagcacccc gagggcgttg gcctggaagt tgggacagga gggcacgaag   27540
caggccgtgg ctggagccgc gctgcccgtg ctccagccga atgagcagga ccgtcaccag   27600
cccttcccgc tgacggacat ccaggaggcc tactggattg gccgcaaggg ggcactgacg   27660
ctcggggaag tctcggtcca ttgctacatc gagtacgaca tggacgagct ggacgtgggt   27720
cggctggagc gggcgctcaa ccgcctcgtt cagcgccacg aggccatgcg tctggtggtg   27780
gaggagagcg gacagcagcg ggtgctggaa agcgtcccct tctacaagat cgaggtgacg   27840
gagctgtccc gggggtcgcg agaggaggag gcacgtgctc tcgccagcgt gcgtgagcgc   27900
atggctcacc aggtgctccc cgcggatcgt tggccgctgt tcgagatcag ggcgagcagg   27960
gctcatggct tctggcgtct gcacgtgagc ctggatgcgc tcgtgctgga tgcctggagc   28020
ctgaatctga tcttcaatga gtgggcccgg ctctaccgcg atgaggagac ccggctcgag   28080
cccctgaacg tcagcttccg ggactacgtc atcgccgaga aggcgttcaa gagcacgcag   28140
acgtggcaga aggcgaagga ctactggctc gcacgagtcg ccacgttgcc ggatgcgccg   28200
cagttgccgc tggcgcagag ccagacacgg ctcgacgcgc agcacttcaa tcgcgagcag   28260
aagcgcctga ctcccgaggc cctgcggtca ctgcggaagc tcgcggacaa gcacaaggtg   28320
tccctgtcca gcgtcctggg gcgcggtctt gccgacgtcc tgtcactgtg gagcagcaag   28380
ccgcacttca ccctgaacat gacgctcttc aaccggctgc cggttcatga gcagatcaac   28440
gacatcgccg gtgatttcac gtcactcaat ctgctcgagg tcgactggcg cggaagtgac   28500
gtgccgttca tcgagcgcgt ccgcaaggtg caggagcaac tctggagcga cctggatcac   28560
cggttcttca gcggcgtgca ggtgctgcgt gagctggccc gggctcgcaa caacccggca   28620
gtggccatgc cagtggtgtt cacgtgcctg ctgggatcga ccgaagggga gggacaggct   28680
cacgagtggg agcgtctgtt cccgaacgag gtcttcaaca tcacccagac tcctcaggtg   28740
tggctcgact accaggtcta cgagtcccag ggcgagctgg tggtctgctg ggattatgtc   28800
gagggtctct tccccgaggg actggtgggg gccatgcacg aggcctacat caccagcctc   28860
gagaggctcc tgcgcgagga gagcgcctgg aatgagacgc gcctgacgaa tctccccgag   28920
tcccagcgaa tccggcgtga ggaggcgaac gcgacggcct ggcgtgagcc ggaactgctc   28980
atgcatcagt tgttcgagcg ccaggtcggc gtggctcccg atgcgaccgc ggtcatcgac   29040
agcgagggaa gttacaccta ccgccagttg aatgtggccg cgaaccggat cgcacgaagg   29100
ctcgcgtccc tgggtctgga gccgaacgag cgcgtcgccg tgctggcgcc gaaggggtgg   29160
cggcaggtcg tggcctgtct gggtatccag aaggctggcg ccgcgtacct gcccgtggat   29220
gggagtgcac ccgccgagcg gatcaacaag gtcctggagc ttggacgggt gagggccgct   29280
```

```
gtcgtcgcgt ctctcgagta cggcggggcg ttcggaagca atgccctcat cgtcctcgat    29340
gacgggctgc tggcgcccgc ttccggaacg gaggatgtga gcaatccggc gccgaagcag    29400
accttggcgg acctcgcgta tgtgatcttc acctccggtt cgacgggaac acccaagggc    29460
gtgatgatcg atcaccgggg ggcggtgaac accctcctgg acatcaacga gagattcggc    29520
gtgcgccagg atgacagggt gctcgcgctc tcgagcctga ctttcgacct gagcgtctac    29580
gacatcttcg ggttgctggc cgctggtgga gcggtcgtca ttcctcccga ggcccatgtc    29640
aaggagccgg cggagtggtg tcactggctc gtccagcacc aggtgaccgt gtggaacacg    29700
gtcccgatgt tcatgcagat gctcatgagt tcgtgggcg cactgccagt ggccgaacgg    29760
gaggcgctct cgcggacgct ccggctggtc atgatgagtg gcgactggat tcccgtcgag    29820
ctgccgaaca cgatcaagcg ggtcttccaa cgcgaggacc tgcgggtgat gagcctcggt    29880
ggcgccacgg aggcgtcgat ctggtcgatc gcctacgaga tcaaggacgt cgcgaaggac    29940
tggacgagca tcccgtacgg gaagccgctg cggaatcaga ccttccatgt cctggacgaa    30000
gggatgcgtc ctcgtccgga cttcgtgcca ggccagctct acatcggcgg catgggcgtc    30060
gccctcgggt acttcggaga cgaggcgaag acagccgcga gcttcctccg ccatccccac    30120
accggagaac ggctctatcg gaccggagac ctcgggcgct acctggccga cgggaacatc    30180
gagttcctcg gcagagagga tctgcaggtc aaggtgggtg ccaccggat cgagctcggt    30240 gagatcgacc accatctgca caagtgcgga tggatccgtc aggggttgac gcacgtcttc    30300
aagcccgatg gcaggaaccc gcagctcgtc gcctacctgg ttcccgaggg agtgacaggc    30360
aagagcgagc aggagcgtgc ggaagagctc tcgttcaagc tggccgggca caacctcagg    30420
aagacggggg gcgcgggcca tcggctcgtg acggagctcg aacccaaggt ctacttccag    30480
cgcaagagct atcgcgtgtt cgccggagag gagtcccggt tgagccagct ggaggcgtgg    30540
ctgcggagcg cgctgctccc gggcaagcct ctcgcgacgg agcggcggga atggacggtg    30600
gcggagatgc tcgcgccgct gctggctctt cgtgaggacg gcctgctgct gccgaaatac    30660
cgctacggtt ccgcgggctc gctctacccg gttcagacct acctcgtcat gggagagggg    30720
cggaaggagc tcgcccccgg cgtctattac ctcgaccccg tgaagcacga gctggtgcgt    30780
ctcgcggacg gcgcgctggc ctgctcctgg ttgagccggc gaggtgttcc cctggcgctg    30840
tgcttcgtcg agaagcgctc ggcgatcgaa cccctctatg gcacgcgcag tgacctctac    30900
agcgccatcg aggccgggag catggcggcg ctcgtcgcct cctcgaccgc cgcggccggc    30960
atttcgtggc ggaccggtc cgcaccagac ctggaggaac tggcgcccgt cgtcctggag    31020
tccgctgact gctccgcgat cgcggtcctc gagcccgcg agctccaggc cctcgacgag    31080
cgcggcaagg actccgatgt ctccgtcctg atgtacgtga tgcgagggtc ggagcatggc    31140
ccacggacgg gttggtaccg ctggtccggg gaccacttcg aggccttcag tgctccggcg    31200
ctcagcatgt tgccgtcgaa ccccgcgaac tggtccatct gccagaatgc gtccttcgcg    31260
ctcttcgtga tggagggaaa ggcacagccg cggacctcct cggcgctctt cacggggcgt    31320
ctgatccagt ccttgatgga gaaaggcgtg gggctgggcc tgggtggctg ctcgatcgga    31380
gaaatggacc ccgagggcgg gcggctcctg agagaagtgc atgacggtga gttcgttcat    31440
gccttcttcg gtggaccggt ggattccgcc cagatctccg cggtgggcac ttccgaggcg    31500
gagccgttcg agcaactcgt gaagcggaag acgcgctcgg tcctcgaggg ctcgcttccc    31560
gggtacatgg ttcccgacca ctacgtcctg ctcgacagct ccccctgtc gagcaatggc    31620 aaggtcgatc gttcccggct cgccgccccg gagttggaga gaccccagaa gcaagacgcc    31680
```

```
ctggtgcggc cctggaacag caccgaggcg gtcatcgcga gcatctgggc gcagttgttg   31740
ggcgtggagc cggacgcggc cgacaacttc ttcgcgctgg gcggccattc gctgaccgcc   31800
acgcagctct gtacgcgtct gcgagaggcg tttggcgtag aggttcctct gcgcgaggtc   31860
tttggtaggg cggatgtgcg gtcccaggcc agcatggtcg agggcctgct gaaacagcac   31920
gtcggtcgtg gggcttcgat tccccgcaga gccgggacgg gccggtccgt ggcgtcgtat   31980
gcgcagaagc ggctctggtt cgtcgagcaa ctggcggaga acggttcggt ctacggaatg   32040
ccggtcgcgg tcgcgctcca gggccccatg gactgggatg ccttcaagaa ggcgctcgcg   32100
ggggtcgtgg cgcggcatga aatccttcgt acgaccttcc acatggagca gggggagttg   32160
tggcaggtga tccacgagga gatcaccgcc cccttcgaga cggagcagtg ccccgagggc   32220
tccgtgatgg agaagcgcgc gtatgtgcgg aagcggatgc gcgagctggc gcgggtgccg   32280
ttcgacttga gcaccggtcc gctgctccgg ttccatgcgt tcgcgctgtc cagggagcag   32340
cacatcctgt tcggcgcgat gcaccacatc atctccgatg gctggtccgt ggatgtcttc   32400
cagtcggagt tgagcgctct ctacaacgcg gcgctgagcg ggagcacgcc ccagttccag   32460
gagctctcca tccagtacgc ggatttcgcg gcctggcagc gggattggct ccgtgggccg   32520
cgctccgaga agcagctcca gttctggaag gactccctcg cgggtgctcc ggagctcctc   32580
caactcccca ccgatctccc caggcccgaa cgtcagagct tccgcggtgg cgtggttcgc   32640
aggacgctcg atgcgcagtt gaccgcggag atcgactcgc gctgccgtga gtggggcgtc   32700
acccccttca tgttctatct cgcggcctac aaggtgcttc tgtccaagct gagtggacag   32760
gcggacattc tcgtgggcac cccggccgcg aaccggcact actcccaggt cgaacgcctg   32820
attggttact tcgcgaacac gctggccatc cggagccgcg tcgaggggca gcggagcttc   32880
gccgagtatg tccaggcggt tcgtgaagga gtgctggcgg cgaacgagaa ccaggacgtt   32940
cccttcgagc aggtcgtcga gagcctccag cttcgtcgca gtctggcgta ccagcctgtc   33000
ttccaggtca tgttcgtgtt cgagaacgag gggcgctcca gcctttcgtt gaacggcgtg   33060
agcgtgcagc cggtatccct ggacgcgcag gtcgcgcgct tcgatctgac gctgctcatc   33120
cgcaacgcgg gagacgcacg ggagatctcc ttcgagtatt cggaggacct gttcaagcgc   33180
gaaacggccg ctgaatggct cgatggagtc atcagcctgg tggaagccgc gacgcgggac   33240
agcagccagc ccctggccgc gctgcccctcg atgtccgagg ccacgctgga aaggtcctc   33300 ggccagttca gccggggaga gcgcacggcg agcccaagc tgtgtctgca tgagcagttc   33360
gagcgtgtgg tggcccggca gggagagctc tgcgccattc aaacgcctcg cagtgagatc   33420
acgtacgagc agctcaacga cagggcgaac cgcgtggcgc gtctgttgtc ctcgcatggg   33480
atccgcaagg gggacgtggt cgcgctctgt ctgaagcgct cgccggatct gttcgcctgt   33540
tacctggcgg tgctcaagct gggtgcggtg tatgtggcca tcgatgggga gtacccggaa   33600
cgccggatcc agcacatgct gaccgacgcg ggcgcgaagc tcgtcgtggc ctcccccgtc   33660
tatgcggaca agctgggaac ggccccggtc ctcgtgacgc tggaggagtg tgaggaccgg   33720
ctggagtcga tggcgggctc caacctctcc gtcaaggtct ccccggagga tgtggcgtac   33780
atcatctaca cctcgggaac gaccggtctg cccaaggggcg cgcgggtcaa gcatcgcggt   33840
gtctccaacc tcgtgctcgc gcagcaggag tacttcgtgg cggggcccgg aaagcggctc   33900
ctgcaattcg cctcgtgcag cttcgacggg gccatctggg agtggacgac cgcgttgctc   33960
aacggcgcga ccctctgcct cgtcgcggag agcagcgccg aggtcgtcag ccgcctcacc   34020
```

```
cgccgcgacg agcagccgcg gatcgacatc gccgccctgc ctccgtccgt ggtcgccagc    34080
cttccggacg attgcctgcc agggctcgag gtgctgctgg tcgcagggga gagctgcccg    34140
cggggtgtgg tggaccgctg gtctcggcgt acgcggatgt tcaacgccta tggcccgtgt    34200
gaagccagtg tgacgtcgac gatgttcgag ttcgatggca ctcgcggtgc gtcgaccatc    34260
gggcgtcctc tgcgcaactg cgatgtctac atcctggatg agcggatgct ccctgtccct    34320
ccaggagtgg ccggagagct ctgcatcgcg ggactgggac tcgcggaggg gtaccacaac    34380
cgggcggagg agacggagcg gcggttcgtc gaggcgagca tcggctcgga gaccgtgcgg    34440
atgtaccgca cgggtgatcg tgggcgttgg gcgagcgacg ggaacatcga gttcctgggc    34500
cgcctcgaca atcagatcaa gatccgcggg attcgcgtgg aaccggatga ggtccgcacg    34560
cagctcctcc aggtgcccgg tgtggcccag gcggctgtcg tcgtcgatcg ggaggggcag    34620
gagacgcggt tgctcgcata cgtcgtggcc tcgccggagg tcccgctcga cctggagcac    34680
gtgcgcaaac ggctacgggc cgcgctgccc gaggccctgg ttccctcgtg gttctgcccg    34740
gttgctacgc ttccgatgac gctcaatggg aagctcgatg tggaggccct tcccaggcca    34800
ggcgaggagc ggaccgaagc gcggttcgaa gagggtgcca cggaggtgga gcggaagctc    34860
caggccctca tcgcgggcgt gctggagggc aggcggctcg gccggcacga cgacttcttc    34920
cgaaacggag gtcattcgct caaggcgatc catctcgtcg cggagatccg gaaggaactc    34980
ggtgccgagt tggcggtgaa gaccatcttc gacgctccga cagtggccga gctggcccgg    35040
gtgatcgaat ccgaaagaag acaggaaggt ccgaccgcct cgcgtccccg cctggagggc    35100
tcccggttca cgctgtccgc cctgcagcgg cagatgtggc tggccgagaa ggtgttgcag    35160
cggagcggcg cctacaacat gccgctctgc ctggagcttc gtggcgcgcc ggatgcttcc    35220
gccctgcaga acgccgtcga catgctcctg cagcggcatg gtgtcttgcg gtggcagttc    35280
aaggaggagt cgggcgagcc ctatgcggag gattgtggcg tcgacacggt gacgctcgcc    35340
acgctcgact ggagggagct ggggcagcag gagaaggaca ccgcactcgc cgggctcatc    35400
gcgacgccgt tcaacctgtc tcaggggcct ttgtggcggg gcgcgctcat ccgaatcgga    35460
gaggagcgct tctggctcct gctctgcgcc catcacctgc tggcggatgg atggtcgctg    35520
ggactccttc tcggagagct ggccgagctc tacaacgcgc gagtaggtca tggcacggcc    35580
cggttgccgg cgcctggcac cgagtactcc cgctatgtcg agcagagtgt cggggatgag    35640
cgggagctcg agcgtcaact cgagttctgg cgtcatcagc tcgagggtgc tccgcagcgg    35700
ctggcgttgc ccatggagtt gaagcggtcc ctgtcacccg gaaaggccgg tgccgtcgac    35760
ttcgaggtgg gtccggagct gaccgctcgt ctccgtgagc tggcggaaca gcggggcagc    35820
agcctcgtca tggtgctcat gagcacgtat caggccgtgc tcgcccggtt cgcgggcgcc    35880
gatgacgtgc tcatcggaac gcctgtcgcg tgccggcaca agccggagct gttgaacacg    35940
atcgggctcc tggtgaatac cctccccatc cgtttgagcc tcaccccgcg tacgacattc    36000
gccgaggcgc tcgcgcaggt ccggcagcgg ttgctcgagg ggatggctca catgacgtt    36060 cccttcgagc gcatcgtctc cgcggtcgca caggagcgcg agcccggtgt cccgcgctc    36120 tgtcaggcga tgttcgtctg ggaggagggc gctcgtggtg acctgaagct cgggtctc    36180 gacgtctcac tgaaggcgac cccggtcacc tccgcgaaat acgacctcgc cctcttggcg    36240
agcgaacagg acggccgtgt cacggggcgg ctcgagtatc ccgaggggct ctatgaccgg    36300
gcatccgtgg agcagctcgc cctcagctac gtgaagctgc tctccgagat ggcgaaggat    36360
ctggagggga tcgtcgcgca ggccgagctg atgtcccagg agcagcggcg gcaattggag    36420
```

```
gcgtggttcg agtaccggcc ggagttcctc gaggctccca acctccacac gctgatcgag    36480
cgtcaggcgg ccaccgcgcc cgcgtcgtca gcgctgcgct acaagggtga gagctacagc    36540
tacgagtggt tgaataccca ggccaataga ctggcgcgct acctcggggc tcggggcatc    36600
gggcgcggca gcgtcgtcgc gctgtgcctc gcgcgctcgc cggagctcgt ggtcgcgtgg    36660
gtggccgtgc tcaagtccgg ggcggcgttc gtctcgctcg atccccatat gcctcaggcc    36720
aggaggcggt tcatcctgga tgacagcagg accgcgctcg tgctgtcgca cgccgccttc    36780
gcggaggagc tcgggaccgg tacggacatc gccgtctggg aagaggtggc gaagcagctg    36840
accgggctcc cggcggagaa cctggagctg gaggtccgtc aggaggagct ggcgtacctc    36900
atctacacct cggggaccac gggcaatccc aaggggacca tgctggcgca ccgggggatg    36960
atcaacctgg cggtcagcga gaagcagcgc agcggaatgg gtcctcagag caaggtcctc    37020
cagttcacca ccgccacctg tgacggttcg atctgggagt ggacctcggc cctggtgaat    37080
ggcgccgagc tctggctgtt ggatgcgagc aatccgcagg agcaggtggc tcaggccatg    37140
caactcctgt cggagcctgg gattaccacc gtcgcgctga cgccgagtgt ggtggagctc    37200
ctccccccgg aagcgatgcc cacggtgcaa tcactcaccc tggcgggtga ggcttgcccg    37260
ttggcgctgc tggagaagtg gtccgcgagg atccccggag tcgccaacgt ctatggtccg    37320
accgaagcaa cggtgaccac ggccacattc cccttccggc ccggctatcc cgcgaacacc    37380
atcggcaagc cgctggcgaa cgtgcaggtc tacatcctgg atgagcacgg caagctgctc    37440
cctccaggcg tcatcggcga gctctgcatc gcgggtgtgg gtctggctct gggctatctg    37500
gatcgcgacg agctgacaca acggaagttc gtcacccatc cgattggacc tcgaggcgag    37560
cccgttcgcg tctaccgctc gggtgacctg gcccgctatc tgccgatgg ccatatcgtg    37620
ttcgagggcc gcagggacaa tcaggtcaag gtgcgaggct atcgcgtcga gctggatgag    37680
gtggcctggg tcctcaagca gcacccgcag gttcagcagg cctcggtgat cgtctcgcag    37740
gccgggaagc ggtatccgta tctcgttgcc tacgtcgtgc cgcgcacccc gccgtcttct    37800
ccggccagcc tgcgggcgga gctgcgtgcg tacatggccg agcggttgag ccactacatg    37860
gttccggagg cctacgtctt catcgagtcg ctgccgctca atcgctccag catgaaggtg    37920
gaggtctcgc tgctgcctcc tcccgagggg gactccttcg ttcgtgacac gctggtgccg    37980
ccagagacgg ccgtggagaa ggagctggcc accctgtgga tggagctcct cggtgtgggg    38040
agcaccggcc gtcatgacag cttcttccgg ctcggcggca actccctgct cgccgtcaag    38100
ctgggtcacg ccatcggcga gcggtggggt tgtgacatct ccctcccacg tatcttcgag    38160
aacgacacgt tggcggcgct cgcgcggtgc atcgaggccg acgagagaag gagccatgac    38220
ctccagctcg ccagggccag tgagcgcgag agctggcccc tctcttttgc tcagggacgg    38280
atgtggttcc tcgagcatct gacccagggg agctccgcct accacgtgcc actcgtcctc    38340
cggctcatcg gcaaggtctc gttcgagcgg ctcgcccagg ccttgagcgc gttggtggtt    38400
cgccatgagg tcctgcgcac cgcctatgtc gaagacggga acacgctgag ccagaagatc    38460
ctcgacgccg ttgccgtcga gatggcgagc agcgacctga gcccgatcgc tcccagtgaa    38520
cggcaggcgg ccgtggatcg tctcctcggt gcggatctcg cgcggccgtt cgcactggcc    38580
gcgggcgaga acgtgagggc acggctcgtg cgcttctcgg aggacgagca cctgctctgc    38640
ctctgcctgc accacatcgc gttggatggt tggtcgatca gcgttcttct gcgggagctg    38700
ggttcgctgt accgggggca gccactccaa cccctgccgc tgcggtacgt ggacttcgcc    38760
```

```
tgctggcagc gcgacgtcct cgagaagcgc ttcgcggagc agctggacta ctggaaggcc  38820
gagctgcggg agctcccgcg gcagctcgag ctgccatggg atcatccccg tccgcccagg  38880
caggactacc gtggtgcttc cgcgcgtcgc ccactgtccg gggaactacg agccgcgttg  38940
aagcaggtgg ccgagcgcta cgatgtgacc gacttcatgc tctacctgac gtcgttccag  39000
ctctggctcg gacggctcag caacagctgc gatgtggtgg tcggcacacc ggtagccaat  39060
cgccactaca acgcgtcga gtccatcgtc ggcctgttcg tcaacacgct gccgctccgc  39120
cttcggtatg acggctccga gacgttcggc ggcgtcgttc gcaggatgaa gtcgaaggtg  39180
ctggaggcgt acagccacca ggatgtgccc ttcgagtacc tcgtggacca tctgaagtg  39240
cccagggagc tgagccacgc ccccatcttc caggcgatgt tcctgctgca ggacgagtcg  39300
gggcgcgaga tcgacctggg tgacgtccag gggcggatcg ctcccgtggc tggcacggtc  39360
gccagattcg atgtgtcgct cctggttgag ttcgatgagg aaggcgcgga gctgaatctc  39420
gagtacgcga gcgctctctt caggcccgag accatcgacg agtggttgga gagcttcgag  39480
ctgttcttgc gcgcgatcgc ggcggacgcg gaggctccgg ttcggcggtt cgagctgttg  39540
ccgccgcgga tgcggtcctt cctgtccgag gtgggcaccg accccggcg agagtatggg  39600
agccttcctc tgcccgagct cgtagcggag caggcgaagc atggcggaca gcggatcgcg  39660
gtcgagggtg tccgggaatc gtggacctat ggtgagctcc tcgccgccgc ggagcgtgtc  39720
gcggccggcc tgcagcgccg cggggttcgt cctggcgacg gggtggcgat cgcgctgcct  39780
cgcgaccatc ggttgccctc cgccatgctg ggcgtcctga aggcaggtgc cttctacgtt  39840
cccctggatc tcacgcatcc ggagcgcagg ctccagtaca tcgcggggga tgcgaaggcc  39900
cggttcgtca tcacgggagg cgagacccgg ttcggattcg acatccctcg tgtgaacctg  39960
gacgagctgt tggaggagac ctcggaagcg cggccggtgc ccatcgcacc gtcgagctg  40020
gcgtacgtca tctacacctc gggctccacc ggtgaaccca agggcgtcat ggtgagccac  40080
gccagcctct cgaacttcct gcacgcgatg gtggaggagc tcggcttcgg gccggatgag  40140
cgtctgctgg ccatcacgac gatcgcgttc gacatctcgg gcctggagct gttcctgccg  40200
ctcatccgcg gggctcgcgt cgtgatcgcg gacgaggact ccacgaggga tccgcggctc  40260
ctgtccaggt ggatcgacga gcgacggatc tccgtcatgc aggccactcc ggcgacctgg  40320
cggatgctca tggatgcctc ctgggtggca cctggatcct tcaaggcgct ggtcggcgga  40380
gaggcgttgc cgcggaacct ggcggacttc atgacgagcc gggtgagcca ggtctggaat  40440
gtgtacggtc ccaccgaggc gacgatctgg agcacgatcg cgcggctgaa gtcgggtgag  40500
cgggtccaca tcgggcggcc cctggcgaac accgaggcct tcgtgctcga tgatgggttg  40560
cgagccgtgc ctcgcggaac cctggccgag ctccatctcg gtggttccgg tctggccacg  40620
gggtacctgg gtagggagga gctcacccgg cagaagttcg tgcatcaccc ggagctcggc  40680
cggcggctct acaagaccgg agacctcgcc cgggtcttgc cctccggcga catcgagttc  40740
gtcgcccggc gggatgcgca gctgaagatc cgtggcttcc ggatcgagcc gggagaggtc  40800
gaggccgtcc tgagcagggt ccccggggtg gcgcgagtca cagtcctgcc cgtggggag  40860
ggggagggca cccagctcgc cgcgttccta ttgacggggg atgagcggct ccaggcccag  40920
gcgagagcac tcgcggagca gcaactgccc gaatacatgc ggcctgcccg gtacgtggtc  40980
gtgcccgagt tccgctgac gcccaacggc aaggtggata cgaaggcgct gcgggcgctg  41040
gtctcggagc aggtggaaga ggcggcgggt tccgcgccga aaaacccgat cgagttcagg  41100
atctcccggt tgtggtcggc gctcctgggc gtccgccatc cgggcacgcg ggacaacttc  41160
```

```
ttcgcgctcg ggggcacgtc actggccgcg gtccggctcg ctcgcgagct ggagagcgaa   41220
ttcggtatcg aggtgcgggt cggtgacatc ttccggaagc ccacgatcgc ggagctcgcg   41280
ggtctggtgg agacgcaagg ctcggagcgg gtcctcgagc ccctcgtcct cttgagccgg   41340
gagcagcaga agccgcccct cttcgtgatc caccccgcgg gtgggatggc gtactgctac   41400
gccgggctcg cacaggaact ctccggattc acggtccacg gcctgaatca accgcactac   41460
tacgagctgg agcaccgctt cgagacgttg gcggagatgg cggcggatta cgtcgccaga   41520
atcaagcggc tccagccgac cggaccctac cgtctcctgg gctggtcgtt tggtgggacc   41580
ctggcctatg agatggcgag gcagttggag caggcgggag aggccatctc cggcgtggtg   41640
atgctggacg cgcatcacgt ctcgccgctg ggcgcgaacc tgccaacggt cgatgtctcg   41700
gcgatgctgg ccaacctggg tctgggcggc gagatggccg acccctacct ggagaaggac   41760
atccgcgaga gcgagcggct ctcccgggac tacaaggcct cgcccgtgcg cttccccgtg   41820
ctcctgttca agcccaccga gcggaatggg ttcgaggaga ggctttacgc ggacctctac   41880
aacggttgga gggagtgcgc ggagaactcc gtggtgcgca gtgtcaccgg cgatcatggt   41940
ggagtcctgg accggcgcaa cgtcagcgag ctggccaggg tcgtcgaggc cttcctgtca   42000
ggaggttacg gagtgctcct gcgtgaagcg gttcagcccg ccctcgcgtt cgcgctcgcg   42060
gagcgtgacc gtttcgtcgc caggcggctg gtggagcaac tgccgcggga tctggtggag   42120
cgctggctga agtcggcgat cgactgtctg ccggagtcag tccggccaga ggggtcgttc   42180
gttcaggcgc tgctcgaata ggtgatgtga agacatacat ggatatggag agtgagcgat   42240
gattcccagc agcctcgaaa aggccatcta cggtgtgtat gcaacgcatg ccctgcacct   42300
ggcggacaag cacaacgtct tcgcgtatct ggcggagaag ggcgccgcgg cgcctggaga   42360
gatcgcgaag gcggtggcgg tcgatgggga gaccctcgag aggttgatgc tcgtcctggg   42420
tgccttggag ctcgtccagg ccgggtccga cgggaagtac cggttgcgtg aggggatggg   42480
gccctatctg gacaagaagg atccccgcta cgtgggtggt ttcgtcacgc atctcatcaa   42540
cagcacgtct ggccggatgg gacacctgga tgcatacctg tccaaaggca aggcggtggt   42600
ggacgcggct ctgccttcgc cgttcgacgt catctacaag gacgaggcgt cgacgaagga   42660
gttcatggac gccatgtggc agttgagctt cgacgtctca cgggagctcg tgaagctggc   42720
gggtctggat tcctgccggc agctcgtgga tgtgggcggc gcgagtgggc ctttctcggt   42780
cgccgcgctg cagcactcca gggagttgcg gtccaccctg ttcgatctgc ccaaggtcgg   42840
gcgctacgtc gatgagaccc gccggaccta cgggctcgag gagcggctgc gtttcgtccc   42900
gggcgacttc ttccgggagg agctcccgga ggggactgt ttcgccttcg ggtacatcct   42960
ctcggattgg gacgatgcga catgtctcga gctgcttcga aaagcccatc gagcgtgtag   43020
ggcgggcggg cgcgtgctcg tgatggagcg gctgttcgat gaagacaagc gagggccttt   43080
cgcgaccgtt ttcatgaacc tctcgatgca tgtcgagacc cagggcaggc acaggaccgc   43140
ccgggaatac gtgggcctgt tggaggccgc gggtttccgt gggtgcgagg tgcggcgctc   43200
ctcgcgcgac aagcatctgg tcatcggttt gaaacacgtc accacctgac cacggctggc   43260
aggggaacca gccacgagct ggtcgccagc caagagagag attcgatgat gcgggttcac   43320
ctgccaggcg agtgcgaaga cattgtccgg ctgcaaaaga gagcgggccg tgctgccctg   43380
ctggagtccg agtgcgaggc gctgtcgctg ctgtatgacc gggtctcggt ggagggcccc   43440
tccgaggagg aggagatcct ggccctgctg acgaggccct tcagccggcg tctggccatc   43500
```

```
ccggagtact accagtacac cagcctgcac gtgtacggct ggttcctgtc ccactaccgg   43560
agggatccgc tccgcgggtc cctcgtcgca ctgcacacga ccctggtcga tctgctgtcg   43620
gtggaggagc agggagcccg gctcggcgag gccacgccgg cctatattca tgagcggatt   43680
cgcgggttgc gaggtctgct cgggcagctc gatgagatcc ccgtggatcg gaacgggccc   43740
ctgttcgtcg cggacgtgct caagggcagc aagaaggatg ctcaggagca gtggcgcgcc   43800
ttcgtcctgg cgcgttgtac gggattcccg aagtcgcaag tacacgatga gtacatcttc   43860
ctccggtcgg tccacgcctg tgagatcgtc ttcttccagg tgcggtggtt ggccctgcgc   43920
atctcggaga tgatcgccgt ggaccggaag gaagccgtct tcctcctggg gcagttgacg   43980
agcttcgcag agctcctgaa caagatcttc gacgtgctga agaccatgtc gcccgagcgt   44040
ttcatgagct ttcgagcaca aacgggaaac gccagcgcag ttcagtccct gaatcatcac   44100
gcgatggaga tcgccgtctt tggcttcgac cccgggcggg cgagcgtgtt cgatggcttc   44160
gagcatctga agcggttgaa cgagccgctg tttcgggagc acgcgtcgtt gcggagtgtc   44220
gtcgaagcca cggcggacgg ggcgctggcg gaaggattcg cgaaactcga taggtgtctc   44280
ctccgctggc ggggagggca ctatgggttc gcccggaagt acctgccggt tgacatcaag   44340
ggctctggag gaacgagggg ggctccgtat ctcaagaggt tcatcaagaa ggacgactgt   44400
cagtcaggcg ggcagcggcc gggtaccgac agcgagctgg cgcggttctt cttctgctga   44460
gcgcgggtga tcggattcct ggacgttgac ccgtgaccgt gagccgccct ggcgtcccgg   44520
gtcgacttcc aaggtcccac ccgggccgga gacaggctgc ggctcgaggc tgcgatgacg   44580
acgagcaact ccgggggaaa cgggcgaagc ccgcgatggc gagggtcatg ggtggtaggg   44640
cgctccggac ccggatactc ttcctcgtgg gacaggccgg cggggtgacc ttcgaggtgg   44700
tgcggtcagt cgaggaagcg cgcgctgcca ctgccgcatg cgcgtcggat tgagtgagcg   44760
cagcggagtt tctcctcgta caaatatggc tccagtacgc gggccagctc ccggtagggc   44820
cgcagcgctt ccgattgcgc ctcatggccc atggcgggcc attctcccag cgccaccatg   44880
accttgtcct gttccaattc ctggatgtct attcctgggc gatgtagctg ctccaggagc   44940
cccctggctc ccccgagttg tcccagcagg ggttgtccga agaaattcag ccaataggct   45000
cctcttacac cggcaccaat ggcctgggtg gtggcgctca gggcgtgcac atccaatccc   45060
gggtattgga cgcaaagctc tcggatgatt cgatcggccc cgagcacttg catcgagttg   45120
aaggcgaggc tggcatatcc ggaggtgagc ggcagaacgc gcgccagcgc cacggccagt   45180
tctctcaccc gtcctggtcc ccgctcctcc aggtactccg ttggcagcca gcaagaaacc   45240
ccgctcacca tgccagaccg ctgggccgcg gtgggtgtct cgagcttgtt cccattgtac   45300
tcgaagcgat acccggccac ctgatgagcg tgctccagca actcgagaga gcatgcctcg   45360
gcatgagtcg tgtccaggag ccgggagcgg atgtatttcc aacccgtgtc atccaatggc   45420
cggaactccc catctggagc ggcgtaccag ccaagcgtgt cgcgtcccac ggtgtcgaga   45480
tagacatcca gcgcgcgagc cacgaggggg gacacgtccg cgtgcgagcg ttgcatgaag   45540
aagcacagat gaagcccctc acgcagggcc aacaacccat ctttggagta cctcctcact   45600
cgcgggtacc gctcgctcat cgcttgattc cttttcttgg gatgacgagg ctgggtcgca   45660
cgccgaatgc gttccagtag accagttcct gggtgctgcc tgcgtagggt ccccgcaggt   45720
aggtcgtcca tgtcgtggag gagccttgga cgcaggggaa tttgaattcg tagacgaaac   45780
gtgcctgtgt gggttctcca gagtggacga ccacatcggg ctccacggtt cccttgagtt   45840
cttttttccg gcccgcccgc acgagtcgat cgacttcctc cttgctcagg ggcttgatcc   45900
```

```
gccacctttt cttgtcgacg cgatagcgtt gctcgatgag gaggtgcccc gggatgagtc   45960
cccccagtgc ctcctcgatg cacttgaatg cttccttgtg cttctccttg cccagctcca   46020
tggctcgcgt gacgggcttg ccgttcttat ccctgcctac cacctcattg cactctgcgg   46080
aggagaggat tctttccatc aactgccgcc ggttgaccgt ctgctccgcg cgctcggcgc   46140
actcctgcat gaactcgtcc agttcgtcct ggaggtcatc gaggtcatca tcatcgccat   46200
ggagcagcac tccaatggcc cagcctgctg caaatccggc tgttgccgcc acggccgttt   46260
gactgacgga tgcgccctgg ctcgtgggag aggtgagtcg gaaggttgcg acttctgctc   46320
cttcgagccc attacagaca tgggtctcat aaggatgcct ttccaaacag caggtgtagg   46380
tggtggtgca tgctttcggt gtatcgagta gacaaccacc ggtgccgacg ctggcgagta   46440
gcaggacgag cataggagat agcgcccaca gcctgggcct ttcggtggtg cgggcgtgcc   46500
gagtcacagg gcggccccgg cctgtgtctc ggcgtctttg atacgaattt cgccggagag   46560
gagcttgggg aggagagtgt cacggagttg cgcaagtgca tggttttgct gctcgttccg   46620
taccttgtcg aggtcaggcc gtgcgtggtc cttgggcagc acgcccttga ggctcgggta   46680
gtctcgctcg atggcgacca tcgcgtcatc cacgagcttg ccgatgacgg gctgcttggt   46740
gttggccttc agcttcgccc agcgcgcctc cttcggcacc cagaacacgt tgtgagcccg   46800
gtactcgtct ggatcctccg gatcggcgcc cttggccacc tctgcgacca gttgggtgtg   46860
ccgctcctcg aaggcgtcgc tgacgtactt gaggaagatg agtccgagga ccacgtgctt   46920
gtactcggcc gcgtccatgt tgccgcgcag gggctcggga tggccgagga tgcgctggac   46980
gagcacttcc ttctcgcgtc caccccggtc caggcccagg gcgtcgcaga tggcctggag   47040
ctcctcgcgc ttgagctggc ccaggagccc ggcgaagtcc accgagcggg agcggacgag   47100
ggcgttgatg tggttctcgg tgacacggcg gtcctcgacc tcgaggccga gctgctccgt   47160
gagctgcgag agccggttcc ggtctagtac caggagcgcg gcccggtgct gctgggcga   47220 gagacgaatc tcctgtgatg gcatgggcgc aggttaccgc atggccccc ccggcgttgg   47280 cgggtgaaat cgtgcttacg gagttcacag cgcgggtagc atggctcgca tgctgcgttg   47340
ggctgggcga gagaagggc gggccgtgct ggtgttcgcc gccgtgtcgc tgctggtcct   47400
cccgctggtg ggactcgtca tcctgtggag ccgggcgccc gaggagcggg tggtcgatgg   47460
gtggcgcttc gtccctgct tgacggccgc ggaactccgc gcgaggccca ccctccgtca   47520
gccgtgccag ggagacgcgc agtgtgatgc tccgctggtc tgtgcctacg acccatacga   47580
gcagcaacgg ctgtgcacgg ccagtagctg tgactcggat tcgtggtgcg cgccgtatgg   47640
ggtctgtcgc tccctcccca ttcgaagtgg gcaacgggtg gccagtcgcg tctgtgttct   47700 cgagggacc cgtgaggagg gagagccgtg tctccgttcc ccgaggccga accagaggga   47760 atgggctgt ggtcagggc tcgtctgcgc gggtgctggc tggtgcggcc ggcggtgtgt   47820
gcccggacag gaggggtcgt gtccggaggg cttcttctgt gctcgcggtg accccgatgg   47880
acccgtatgc cagcccacgt gcgagggccg cgcgtgtccc gagggccagc agtgcatcca   47940
gtgcgagggg ggtgtgtcgg tatgtgcgag ggtgaaagga cgcgcatgcc ctggcgagcc   48000
ctgtaccggg aaccgggtgt gtgtgacgga gatgtccgtc cacgccgtgg gggaggcgcg   48060
gaggcggtgc gtgcagccct gtggtcaggg cgggcccggc gaatgtgagg agaggtttcg   48120
ctgccaccag gggcaatgcc gccggcattg tctcgtgggg cagcccgaag tgtgcggccc   48180
gttccggttc tgcgtacgca ccgatgaggc gggtaacggc gtgtgcctgt catcgctgga   48240
```

-continued

```
gcaatgggac atgaacgccg agccggcccg ggagggcgag tggaatcgtg cgccgggccc   48300
actgcgcagg tagcatggcg cgcatgatgc gaagggttgg gcgggagaag gggcgggccg   48360
tgctggtgtt cgccgccgtg gtgctgctgg tcctcccact ggtgggactc gtcatcctgt   48420
ggagccgggc gccccggag cgggtggtcg atgggtggcg cttcgttcca tgggtgtctc   48480
ccggggaggc ccgcgaacgg cccacccctcc ttcaaccctg cctgggtgac gagcagtgtg   48540
acgccccgtt cgtgtgtttc catgaccccgc gctatcagca acggtggtgt acggccagtg   48600
attgcgagtc ggactcctgg tgccccaccc agacggcctg ccggtccatt cccatgcggg   48660
gacggcagaa gatggctctc cgcgcatgtg ccctcgaggg cacgcgaaag gagggggagc   48720
ggtgcctccg gtttcctcag gcggtcctgc gggagtgggc ctgcggggag ggactcgttt   48780
gcgccggttc cggctggtgc ggccgacgat gtgttcccgg gcaggagggg acatgcccgg   48840
agggcttctt ctgtgccccc ggcgacccccg atgggcccgt gtgccagccc acgtgcgagg   48900
gccgcgcgtg ccccgagggc caggagtgcc tccaactgga gggcggcgcg tcggtgtgcc   48960
tgaaggtgca gggacgctca tgtcaggacg atgaaccctg ctccgatgga gaggtgtgtg   49020
tgacggagcc gttcctttcc ttgaaggggc aggcctggag gtcgtgcgtc cagacctgtg   49080
gacacgaagg tgccgcgagc tgtccagagg actccgtctg cttccacggc cgctgccgcc   49140
tgcgctgctc gttgctgcgt ccctacccgt gttggacccg gttctgcgtg agcaccgacg   49200
acgcgggcaa cggcgtgtgc ctgtcctcgc cggagcaatg ggacatggtg gacgccgagc   49260
atcgttgacc cgcgaccacg agccgcccta gcgttcgagg ccgattccaa ggtcccaccc   49320
gggccggaga cgggctgcgg ctcgctggcc accgtgtggg cgcccgaccg cgtgggggga   49380
cgcgagcggg ccgtgtgctt ccaaccacac ctcccctcca gaacggcgtc cggcaccccg   49440
gcacgccgcg tgaacaaccc gagccattc ctcggaggaa ccatgggtcc gcagtccgtt   49500
tcaatgccga agccgttccg cacggccagg gcgcgctggt tgctggcggc gctgctggtg   49560
ggcgcgatcg ccggctgcaa caaggacgaa tccacgagca ccccggcacc gtccggtccg   49620
gcccccacct cgggggcccc ggccagcggc agcggtccat ccggaacgag cactccgagt   49680
gccccgccct cggcggactc cctcgcccccc gtcatccacg agatcggccc cgagggcatg   49740
gtgccgcgcg aggtggtgct ggagttcccc cgctcggtgg cgcccgagaa ccaggaggtg   49800
aagaagggca ccgtcttcac ggtgtctccg aacgtgccgg gctcgctgag cttccgcggc   49860
ggctccacgc tcgtcttcac cccgcgcgag agcttcgcct tcaagaccga gtacactgtc   49920
tcgctcgatg cgctcgagct ggccgacggc accgtggtga gccccaggt cgcgggggg   49980 tggagccgca ccttcaccac gcctgccttc gccttcctgc gcctgtcgcc ccggcagatg   50040
gacgtacgca agggcaaggt ggaagcggac ctggtcttct ccggcccggt ggacgtggcc   50100
aacgtgcgcc gcttcgcttc cttctccgtg gacggcaagg cgctgtccga cgtgaagctg   50160
cgctcccacc cctcggaccg tcacatcgtc accgcggccc tggggggcgc gagccttcgt   50220
cccggcgcgg aggtgaagtt caccctcaag cagggcctgg cctcggctgg ccgcaatggg   50280
ggcaccgcgg cggcggggga gggctccttc gcgctgcacg tgggcaagcg cctcgacatc   50340
accaacgcct acgcgcagga gggcgcctcc ggtcattaca tcgaggtccg ctgccgcgag   50400
gtggagggtg acgcggcgcc cagccacccg gagggtgagg aggattacga ctattactat   50460
ggagaaggtg gcgagcgctg cagcctcgac gaggactccg ccgcggacac catccacttc   50520
aacccgccgg tgaagctctc cgtgtcgccc tcgcgctggg gcttccgcgt cttcggtgac   50580
ttcaagcgtg gctcctattc catgcgcatc gacgcgggcg ccacctcgtc caagggcggc   50640
```

```
acgctgctgt ccacctacga gaagtccttc tccatctccg cgcgcagccc gcagatcagc   50700
ttcggctcca ccggccgcta cctgccgcgc agcgcctggc gcaacctgcc cctcaaccac   50760
ctcaacctgg actcggtgga gctcgtggtg cggcacgtgc cccaggagaa cctcctcttc   50820
tggatgagca atgacggtca ggaggccgcc gacgagcgca cctccaacgt gctgctgcgc   50880
aagacgctgg ccctgaaggg cgcgcaggac acgctggcca ccacctggct ggacgtgggc   50940
agcctcgtgc ccgcgagcac ccggggcctc gtggagatca ccgcctcggg cagctacaag   51000
tcgtccgcct cgcgcatcct cctcacggac ctgagcctgg tggccaagcg cggcctggcg   51060
ccccggggct cggaggcgaa ggaggaggtg ttcgtgtggg cgctcggcat ggagagcacc   51120
gagccgctgt ccggcgtcga ggtctccctg gtgaagaaga gcggccaggt ggtggcccgc   51180
tgcaccaccg gggcgccga cggtgcaag ctgacggtcc ccgcgccggg ggtggatacg   51240
gccgagccct cgccctgct cgcgcgcaag ggagatgagt tcacctacct caagtacaac   51300
gagctgaaga cggagatcgc caactcggac gtgcagggcg agccgtaccg ctcggacaag   51360
ccctaccgtg cctccgtcta ctcggaccgg ggcgtgtacc gcccgggtga caccgcgcac   51420
gtggtggcgt gttgcgcgg ccaggacgac gtggcgccgc cggtgggcat gccagtggag   51480
ctgaaggtgg tggacccgcg cgagcgcgac ctgaagaagg tgacgctgaa gacgaacgag   51540
gcgggcctgg tgtcgctgga cgtgcccttc gaggcctacc aggacacggg cgcctaccac   51600
gtggtgctga gcgtggccgg caagcaggtg acctcgtacg gcctcaacgt ggaggagttc   51660
gtccccgagc gcatgaaggt gacgcccag gcggagaagt ccggctacgt gcagggcgag   51720
gaggtgccgc tgacggtgga ggccgcgtac ctcttcggtg gctcggcgga aacagcccg   51780
gtggaggtga cgtgccggct ggagccgtcc gtcttccgcc cgaaggacaa cgcgcagtac   51840
gcctacgggg tatggcgtcc ggagggctcg gacgcgaagg ccaccgtgtt ggggcaggtg   51900
aaggccgagc tggacgcgaa gggccgcacg ttggtgcgct gcccggcgca gcaggacgcg   51960
ggcggcttca agggccccggc gaagctggtg gcgcaggcca gcgtcttcga ggccggcagt   52020
ggccgctcca cgctgggcga ggccaccgtg ccggtacacc cggaggcgta ctacgtgggc   52080
ctccaggcca acgtggacaa ggtgaaggcg aaccagccct tcaccgtctc cggcgtggtg   52140
gtggactggc agggcgctcc ctacggcaag gccgtcaaac cgctcgacgt ggagtacctg   52200
cgcctggatg aggagtacgg ctacttctat gacgagggct cgggcgagga gcgctaccag   52260
cgccacctgc gtcccgtgcg cgagggccgc accaccgtca agcccgaggg cgggaagttc   52320
tccttccagg tgacgccgtc cacgatgcc gcgggctacg tggtgcgggt gaagtccggc   52380
gcggcgcaga cggatctgca gctcgagggc cacggccgtt attactggtg gacgagtcc   52440
tcctcgcggg tggaccagac gccccggccg gcgcggccca cctcgctctc ggtggagctg   52500
ccacgctcgg cgaaggtggg ggactccatc acggtgaagg tgaaggctcc ctaccgtggc   52560
cgcatgctct tcaccgccga gacgatgggg gtgcaggccg ccgagtggaa ggcggtggag   52620
ccgggcgagg tgacgtggac cttcaagccc tcggccttcg cgcccaacgt ctacgtcagc   52680
accttcctgg tgaaggaccc gcacctcgag tccgcccagg ccttcatgcc ggaccgggcc   52740
ttcggcgtgc ccagcatgac tctgagccg gtggacttca gcaggccgt cacgctgaac   52800
gtgcccaagg aggttcgctc caatgacacc ctctcggtgg acctggagct gggctcggtg   52860
gaggcgggta ccttcgccac ggtggcgtg gtggacgagg gcatcctctc gctcacgcgc   52920
ttcaagagcc cggatccgct cgcggagctc ttcacccggc gggccctggg cgtgcagacg   52980
```

```
tacgagacgc tcgggtggac gttgctgatt cctcccgccg gcgccagccg ctccacgggt    53040
ggtgacggcg agggcgatgc ttcaggccgc gtgcagccgg tgaagccggt ggccctctgg    53100
agtggcgtgc tgccggtgcc cgccaacggc aagctgcgcg tccccttcaa gctgccgcag    53160
tatcgcggcg cggtgcgggt gatggcggtg acgagtggcc ccaagcgcat cggccacgcc    53220
agcgcgcagg tgctggtgcg ggatccgctg gtgttgcaga ccacgctgcc ccgcttcctc    53280
agccaggggg atgagattca aatccccgtc ttcgtgacca acctctccgg caaggcgcag    53340
gacgtgaagg tgtccctcac cgcggagaac ctcccggtgc cgggcatggc gatgcccgcg    53400
tccatggcct cgccgctgca actgctcggc aagagcgagg gcaaggtgcg gctggaggag    53460
ggcaaggcgg ccacgctcgt cttccaggcg aaggcggtgc aggccgtggg cgcggctcgc    53520
ctcaaggtga cggcggaggg cggtggacac acctccttcg agcagctcga cgtgcccttc    53580
cttccctcgg gcccgcgcga gcgcaaggtg cagcggctcg aactggccgc cggcacgttg    53640
gatctgtcgc agtacctgca gggctggctg cccaccagcg agcgctcgac gttctgggtg    53700
accacgaatc cctacgccga gtccttccag cacctctcgt acctggtgca gtacccgcac    53760
ggctgcatcg agcagacgac gtcctccacc cgcccgctgc tctacgtctc cgagctcgtg    53820
gacagcgtgg acccgacgct cacggccaac gcgaaggtgg aggacatggt gatgtcgggc    53880
gtgaaccggg tgctctccat gcagacgccc tcgggcggct tcggctactg gccgggcgcc    53940
accgagccgg tggagtgggg cacggcctac gccacgcaca tgctgttgga tgcgcagaag    54000
cgcaagtacg cggtgccgca ggaccgcatc gacaccgcga tcgattggat gaaccagcag    54060
gtgacgcgcc gcgagggccg ctcgggctcg ggtgactaca cgatggctc cgaggcctac     54120 atgcactacg tgctggccat gtccggcaag ggtcacaagg cgcgggtgca gaagctcatc    54180
gaccagctcg ggagccagaa gttctggagc aacggccagc gggcggagca ggaattcatg    54240
ctcaaggccg cgctgtacca ggccggcgac cgccgctacg agaaggacct gcgcaacccg    54300
gacgcctcgg cggtggtgga ggagcggtgg aacggttggt ccttctactc ggaccggcgc    54360
cggcgcggct tcatgctgag cacgttccag gacctgttcg gggatgacgc ggcgggcgag    54420
ccgctcgcgc agcaggtggc cgaggccctc aagcaggagc gcagcagcta ctacaccacg    54480
caggagctgg tctgggcat caccggcctg ggcaagcgcg tggcgggagc ggcctcgaag     54540
ttcgctccgg cggtgctgac ggcggatggc aaggaggtgg cgacgcggga gggcgtcaag    54600
caacgcgcct ccgatcggac gtgggcgctg gtgcgcgcga gcgagcgcaa gggcctgacc    54660
ttgaaggtcc cggagaaggg tgagggcaag ctctacctgg tgctcgcgag cgagggcgtg    54720
cgctcggacg gccagtaccg cacgggcggc gaggggcttt ccctggagcg tcactaccgc    54780
aacctcgcgg gcgacgtgct cgatgtgcag ggcggctcgg tggccctggc ggacctcgtc    54840
tacgtggagg tgaagatcaa gaacacctcg cgtgagcgca tccagaacat cgcgctggtg    54900
gaccggctgc cggcgggctg ggagatcgag aacgcacggc tcgggcgcgg gggcgcggtg    54960
gagtgggcct ccagcgagga gcagtggagc gcggactacg tgaacatccg ggacgaccgg    55020
atggaggtct tcggaagtct ggaggcgggc gagacgaaga cggtggtcta cgcggtgcgc    55080
gcggtgacgt cgggcaagtt cacgctgccg ccggtcgagg cggaggcgat gtacgacccc    55140
cgcatctggg cgcgcgaggt gggaggctcg gtcgaggtct ccggcccctg gaaggacttc    55200
ctgctgtagt catggcggag gcggtcgctc tggcggggac cctggaaaca gggtcctcgt    55260
caaagaacac gctggagcac tcgaggatcc acgacgggg caattaccag ccgggatatg     55320
gcgaaggcgc ttatgtcggt tccgatgcca gctcggccaa tgacaacacc ctcatccggt    55380
```

```
acaacgaagg ctaccggaac gggaacgcct ccgtggtgga cgccttccag gtccgcacgc    55440
acggcagcgg tgatgatgct ccgggatacg tggtgtatgc gacgagcgcg accacgggca    55500
cgacagcctc cggtgatgtc aggattggcg gcgggaatct gtataacggc aacgtgaaca    55560
gatgagacgc cgctccgggc cttcgaggtg cgccctcagc gctggggcca ggacaggatg    55620
atgcgcgctc cgcccagggg cgcgtccgct acacgggcgc ttccctggtg cgcctgcatg    55680
atgcggtgga cgatggccag gcccagtccg tggccacccg tcttgcggtt gcggctgtcg    55740
tccaggcggg tgaagggcag gaagatgcgc tccctgtccc gaggcgggat gccggggccg    55800
tcgtcgtcga cgagcacgga gtagcccgag tcgttcctct ccaactgg                 55848

<210> SEQ ID NO 2
<211> LENGTH: 2049
<212> TYPE: DNA
<213> ORGANISM: Artificial
<220> FEATURE:
<223> OTHER INFORMATION: Seq.-ID No. 2: arg1

<400> SEQUENCE: 2
atttgttgct cacgatacgc gtcccgggct tttctgatgg ccagaccga cctactcctg       60 ctgaacgcat ccaatcttcc gcagctcccg atctatccgt atgccttcgt gcaggttagc     120
gcgatcgctc gtcggtttgg cctttctgtg cggaggctcg atctattgca ggtgcgccgc     180
gagttctgga ggcccatgct gcgggagctc atccaacggc atcggccccg gatggtgggt     240
atccatctgc gccagcagga tacggtgctt catttcgact atcacaaccc acagatgggg     300
gtgatggcgg ggcgctattt cccggtgcag gacacgcggg cactgattga ggtgcttcgt     360
gaggtgggcg acatgcccat caccatggga ggattcgggt tcacgtccca tgcccatctc     420
ctgctcgatt atctcggggc tgacttcggg gtgcaggag atccggatgg attcttcgcc     480
cgcttcgagg acgtcgtcgc gagacgcgat ctggaatcgg ttccagggct ggcctatcgc     540
cgcgatggca cctatcagtt caatccgcga gggttctatc ctccggcggc ggagcgcgag     600
tatacggacg agatcgtcga tgagctgatc tccttctatg gacatgctca gctctacggt     660
tccaacccgc caacggtggc cgtggaggcc atgcgcggct gcccgttcag ttgcggtttc     720
tgtctggagc cccacgtcaa gggacgccgc atcgcgtacc gcgacatcga accatcgtg     780 agcgagctgg agttccttct cagccgcaac ctgcgccggt tctggttcgt tgcctccgag     840
ctcaacatcc aggggtcgga attcatcttg aagctcgccg agcgcgtcat ccggctcaac     900
gagacccatc ccgcagccc gatcgaatgg tccggtttca ccctgccacg attcaacgag     960
tcggatctcc ggctcctgca gcgcgcgggc tacgcgggtg ctctcaatga catcctctcg    1020
ctcgatgacg aaaacctgca ccggatgcgg gttccctacc gctcgggtca ggccatcacc    1080
tatctgaagg ccatggccaa gatggccgag gaggagagcc aggcacaggc cacgagtccc    1140
cacggggtgg aggggctgcg ccagcggctg gcgggctatt tcaccctgtt cctgggcaac    1200
tcccacgccg acgagcggac catccgccgc tcgctccagc aggtcgacga gcacggccta    1260
cgcgagaagt accgcgggc gttcgtgatg gccgcgactc gggtctacga catcgagggc    1320
aagtacatct gcgccacgag cgaggaagag gcgaagagca tcatctcgta cgacgagcgt    1380
ggtgagcgcc cgttcaacct gctgtggccg tccttctact accctcggtt cctgatgcag    1440
cggctcggct ccacgcggga gatcctcaag ttcttctcgt tcgttggaga caccttcctg    1500
tcgctcgctc atcgcatgcg caaggattgg aactggttct gtcgcggaa cacgagcgtg    1560
```

-continued

```
gaacaacttc gcgagtggct cgccggagcc tcctcggtgc ccctcggagc ccacgaggcg    1620
ccgccgcatg tcctcgagaa ggcggcgcac gtcctcggag agccccggac gcccgcgctc    1680
gtgtcgatga tggccccgga acccgagcag aagcccctct ggaacgaggt cgccagggtt    1740
ctgctcgagc acctcttccg ggtgcacggc aagtcagtgg cggcggtgac cacgcatctg    1800
gggattcagg cggatgagcg tggaattccg cgattgtcgg aataccggct catggagcgg    1860
ctgtaccaac gctacgattc agtggagcaa ctcatcgagg aggcaggatc ttgcctcgat    1920
gtgacaggcg attcgctggc gatgctctat ctgcaatggc tgctctatgc caacaacgtc    1980
acgattcgtc ccgaataccg cgaattgctc ttcgagccgc cggtcgagcc tgcttcagcg    2040
gttggctag                                                            2049
```

<210> SEQ ID NO 3
<211> LENGTH: 10617
<212> TYPE: DNA
<213> ORGANISM: Artificial
<220> FEATURE:
<223> OTHER INFORMATION: Seq.-ID No. 3: arg2

<400> SEQUENCE: 3

```
atgagccgtt gcaacagcg gcttcgagat agaacgaaaa tggatacgcg caagcaggcc      60
tctggcgagg tgtgtttcct cgacctcttt ctgcgtcaag cggagcttca tccgtcgaag     120
tccgcggtcg aatgcggctc ggcccggctc acctatcagg cgcttgtcgc caggagtgaa     180
cggctcgcat ccgcgctggg ggcgagcggc gttcatccag gggatcgcgt tgccgtcgtc     240
ctgcatcggg gactcgacac cgtggtcgcg atggtcgccg tgcttcggac cggtgccgtc     300
tatgtgccga ttgacgtcac ctggcccgac aaccgtatcc gttacatcct cgatgacctg     360
cagccgggcg cgatcctgtg tgacgaggag aactcgcggc gcgcttgctt cacgagtgat     420
gaccggctcc ttctggcctc ctccgagggg acaggggct cggatttcag gcctggcccg     480
atggcgcccg cctacttcat gtacacctcg ggctcaacgg ggcgacccaa gggcgtggtg     540
ctcgctcatg gcggtctggc gagccggctg catgcgttct ctcgcgcata tgagatccaa     600
cccgaggacc gctttctcgc cctgagctcg gtctccttcg acgtgtcggt cctcgacctg     660
atgcttcccc tcgtcaatgg atgctgcacc ttcattgcgt cggatgagca gcggcgcgat     720
ccggatgcgc tgcggaacct gttcgaggag cgggcgctga atgtcgcttt cgccacgccc     780
accacgatgc gcgccctcgt ctccgtggga tggaaggga gtccccgcac caagatcctc     840
tgcggtggtg aggcgatacc ccagtcgctg atgaacgaac tcgtcgcccg ggggcggttg     900
ttcaacgtct atggaccgac ggaagccacc gtcgcggtca cttcgccaga gctcttcgcg     960
ggtgacagtg tgcacctggg ccgcgcgctt ccggggtgg agttgctcgt cctggacgag    1020
gccggagcga tctgtggacc ccggcagcca ggagagctcg tcatcggcgg gatcggtgtg    1080
gcgctggggt attggaagaa tgacgagctc acccggaaga agttcgtcga cgggaagtac    1140
cggacgggcg atctcgtgag ctggggagag gacggcaatc tctactacca cggtcgcatg    1200
gatgagcagg tcaagctcca cggtcaccgc atcgagttgc tggagatcga ggagatggcc    1260
cgctcgttgg ggctcgtccg tgacatcaag gtcctgattc aggagaacgc ggcatccct    1320 cggctcgtgg ccttcttcat cggtgacgag gcagccgcac aatcgctgcg gaggaggctg    1380
gccagcgagc ttcctgccta catggtgccg tcggtgtggg tcggggtcga gggctttccc    1440
cagacgtcga ccggcaagct cgaccggaag gcgctcctgg cgaaggtcga cgagcgcgcc    1500 gagggctcg acagtcctcc ggaagcggct ccgtccggcg gtcgcgaggc gactctgctt    1560
```

-continued

```
ggtatctggc gggaggtatt gcagcggccg gatctgtccc cggacgatga tttcttcgcg   1620
agtggtgggg attcgattct ggcgatgcgc accctgagcc gggcacgcga agcgggaatc   1680
aactaccggg cggttcatat cttccagcac ccgacggtgc ggagtctgct ggagaccgtc   1740
gttcaggcgc acgaagggcc caggcccgaa ctgcccgagt tgaccacctc gggtctgacg   1800
cccgtccaga gatggttctt cgagcagccg ctggtcaacc ggggggttctg gaatcagagc   1860 attctgctcc ggctgacgcg cccgatggag ctgcgagagc tccgggagat cgcggactgc   1920
ttgacccgga cgcatcagat cctggcttgc gagatcgatg aaaagggaat gcgactgggc   1980
tccagggacg ccgacgcatg ctgcgcccag gtgtccctga ccacgggaag cgggacgtca   2040
tccccagaat ttgcccggat catcgacgat gcgcaccgga gcctgcgccc tgaggaggga   2100
aggctgcatc gcctggtcct gatcgaatcc aggggttctg gcgagtggta cctgttctgg   2160
acgattcacc acctggtcat cgacggtgtg tcgtggcgga tcctcttgag tgacctgggg   2220
acccttctcc agcagaaggc cagcggagac gcgctccatc tggagaaggc ccccgtgagc   2280
ttcctgcatt gcagtgagcg tatgcgggcg ctccacggga aggtgcggga ggcagagctt   2340
tcgtactgga ggaagctccc cgaggcgccg ttgccctgga gctccgaagt gcggcaggag   2400
gtgcccgaag cggcgcggac cgagctcgtg ctctcgctct cacaggaggc gacacgcggc   2460
ctgctccaga atgtgctggc cggtacgggg aagggcatca acgatgtcct gctctccgcg   2520
ctgctccagg ccgtgtatga cgtgtctgga gagagacgcc tgtcactgtg gctcgagggg   2580
cacgggcgcg aagaaggtct gctcgaattg gatacgtcca ggacggtggg ctggttcacg   2640
tccatgttcc ctgtctacct ggagagcccc tcgccggagg acttccagtc cacgctcgag   2700
gcgacacgcg cgtccctcgg cgcgatgccg aaccgtggcg ttggctacgg catcgtgcgc   2760
tacctgggag aggatgcgcg cggagaaggc cttcgtaccg gcaatgagcc gcgcatcagc   2820
ttcaactatc tgggccaatg ggacgacgtc gccagcgacc atttctcggt cgtgagcgaa   2880
cccggcctcg atgacatcgc gcccgagaac aagtggcatc gagaggtgga catcaactgc   2940
ctcgtcgccc aggggatatt taaggtccac ctgacattcg tgcggcggct ccaggacaag   3000
gagaagctcg agagtctgct gcgtcgcttc atcgcgcgct tggaaagcgc catcgacgcc   3060
tacaagggcg ccggcgagtt ccggcggaag ttccccctcc tgtcgattcc tcccgaggcc   3120
ttcgcccgca acggcatcga tctccaatcc gtgcaagatg cctacccgct gacgcccatg   3180
caggaaggca tgctgctgcg tgccctgacg gtgccggaga gcggcaacta tatcgttcgt   3240
accttcttcg acctcacggg agagctccat cccgacgcct ggcgggaggc gtggcgacgg   3300
gagttggccg agcaggaact gctgcgctcc gcgttcttct gggagcattc accgaccccc   3360
ttccaggtcg tcttctctca cgtcgacctc gattggcgga cgcacgactg gcccacctc    3420 ggcccggagg agcagcagca ggcgttctcg aagctggaga aggctcgtca tgccgaggga   3480
ttctccctga gcaaggcgcc tctgcttcgg atcgatttca tcgccagggg cggcagtgat   3540
tacaggctcc tcctgagctt ccaccatttg attctcgatg gctggagtct ccaggtcctc   3600
ctggagcggg tgctgaagcg gtatgggcag gcgcgaggtg gcggggaaga acggctgact   3660
ccagcatttc gtttccgcga ttacgtcgcc tggaaccgca accacgagtc ttctgatgcc   3720
ctgcggttct ggcgcgagca tctcgagggg gtcgaggagc cgaccctgct gggtgacgag   3780
cagggcaccc ggcacgagta cgcggaaacg gtactacgtc tggaagaggc ccggtggtct   3840
gggctcggtg cccggtgccg gcggcagggg atgaccaaga gcagcctgat tcaggctgtg   3900
```

```
tggtgctggg tggcgaagtc ctacgggcgg aagagccatg tggtctatgg cttgactcaa   3960
gcaggccggg ccgcggccat cggcgatatc gaaaacggcg tgggcctgtt catcaccacg   4020
agcccggtcg cggtggacct ggacaagcat ccaagctgt ccacggtggg aagattcatc    4080
cagcaggtca acgcccaggc cctacaccat gaccggctcc ccctgagtga gatccagcgc   4140
atctcggggc gcgagatcgg acaaccgcta ttcgattgcc tgttggtatt cgagcaggag   4200
ccgatcccg aactcgcggg aggcgtgagc ggcggcctgt cggtggccgg tactcggacg     4260
tatgagtcaa cggagtaccc tctgaccctg agcatcctgg agaagaggga tgggagctgc   4320
gatctccgct tctatttcaa caagaagaac ttcagtgagt tcagggtaga aggactccgg   4380
cttctgttcg aggaaatcct tgccgcgtgg gaaagagagc aggaactcga gctctcttcc   4440
ctgcctgcct tcccgagccg ggatggcgcg cttctctcgc ggtggaacgc gacccgggtcg  4500
gactacccgg cccaatccct gacggagctc ttcctgcagc aggcccggcg tacccccaac   4560
caccgtgccg tgcgatacgg cgagcgcgag ctatcgtacg cggaattggc cgagcggacg   4620
gggaccctgg cccggcgcct ggaggcgctc ggagtccgcc ccggaacccc cgtggcggtg   4680
cacatgcatc gcagcctcga gatggtcatc gcgctacacg cgattgttcg agcgggtggc   4740
gcctatgtgc cgatcgatcc ggagtatccg gcggcgcggg tgcggacgat cctggaggat   4800
gtggcggcac ccgtcgtcat cttccacgac gcggctccct tgaagtgcca ggtgggtggc   4860
accgttttgg atgtcacccg gattgtcgag gagggtcatg gcggggcgga ccaccgcgcc   4920
gcggagtatg accccgagcg gttgatgtac atcatctaca cctcgggctc cacgggacgg   4980
cccaagggcg tcaagtgtag acacgagggg gccgtcaacc ggatctgctg gatgcagcga   5040
agctacccgt tgtcatccga cgacgtggtc ctgcagaaga ccccgtacac gttcgacgtt   5100
tctgtctggg aatttcttctg gcctctggcg gtgggcgcca gctcgtggt cgcggcaccg   5160
ggcgtgcacc aggacgcgag cgccctggct gctctgatcg agcgcgaagg tgtcacacac   5220
ctgcacttcg tgccctccat gctggatgtg ttcctcgcga gcaaggggg cgctcgctgt   5280
gcctccttgc gccgtgtctt ctgcagcgga gaggcattgc cctcgccggt ggtcaaggag   5340
ttcttccgct ccgtgccaca tgcggagctg cacaatctct atgggccgac cgaggcctcc   5400
atcgacgtga cggcgtggga ctgtcggtcc gacagtccgg tggcctcgat tcccatcggc   5460
tacgcgatcc agaacgtgcg gctccatgtg ttggatgaga agcaggctcc cgtgcccac    5520
ggtgttccgg gcgagctctg catcgcggga atcgccctgg ccgaaggcta tgtgaaccgg   5580
ccggaggaga cggcgaagcg cttcgtccag tcctcgtggg atgcgcggga gcgcctctat   5640
cgcacgggcg atctggcccg ttacctcccc aatggagcca tcgaatacct ggggcgactg   5700
gatcagcagg tcaagctgcg agggttgcgg atcgagctcg atgaggtctc gagcgtgctc   5760
ttgcgcgatg cccgggtgcg gcaggccgtg gtccgcgtcg tcgcgggtcc cgcggggcaa   5820
cccgtgctgg ccgcctacgt cgttgctcac gaaggctcgg ccggaacgtt ggaggaggca   5880
ctgaaggcgg agctcgagcg ctccctgccg aggtacatgg tgccggagtt cttcttcttc   5940
ctggaggcgc tcccggtcaa tcgcaatggc aagctggatg ccgatgctct gcccaggccc   6000
ggggcctctt cctctcggga gtgggagccg cccagaccg aggtcgagaa ggatctcgcc    6060
gcgatctggc agcgggtgct gggtgtcgag agggtaggga ggaacgacag cttcttcgcc   6120
ctgggggcg attcgatcct gagcatccgg atcctggccg tcgcgaagga gcgcggatgg    6180
gacgtgagcc tcgggagtt gttccggtct ccgcggttga gcgacttcgc caggaccgcg   6240
aaggcggcgg cgcacacgcc cgtgctcgcg cgctccgcct tcagtctgat cagcgctcgt   6300
```

```
gaccgggccg cgatgccggc aagcgtggtg gatgccctcc ccatcgcggc cctgcaagcg    6360
ggaatgctct tccacacgaa gctcgcggag gaaggtgtca tgtaccgcga cagcttcctc    6420
tacgtcattg gtggggagtt caacgagcag gcgttccggc aggcgttgaa ggagttggtg    6480
catcgccacc cgatgctccg caccagtttc gagctcggtg catactccga gccctgcaa     6540
cgggtggagc gggaagtgga gttgccgctg cggctcgagg actggcgtga cagccaggat    6600
caggagcagc gtctgtcggc gtggcatgag agctaccgcc cgacgttcga catcactcga    6660
gcgccgctgt tcaagatgga ggtcaagctc ctgagcggtg ccaggttcgc cctgggtctc    6720
tgcttccacc atgcaatcct ggatgggtgg agcatcgcgt cgatgatgac ggagctgctc    6780
ctggactacc agcgcctgct gacgggtcgt gggcgggcga tcgagccgct ggggtctgga    6840
tacgctgact atctggagct ggagaagcgt gtcgtcgagg atccccagca gaaggccttc    6900
tggtccacgt acctgaatga cgcccagtcg ttgaggttgc ccgtcaagca ggaggtggag    6960
catcggaatc ggcgtggaac gagtgtccac ggccggttcg acattcccga ggagctcgtc    7020
gggcagctgg agcggatcgc caggtccctg agatcacca agaggcatct gttcctcgcg     7080
gcccatttcc gcgtcctcgc gatgatctgc gggcataagg acatcgtctc cggggtcgtt    7140
acgaacggaa gaccagagac ggtggacgct gaacggatcg tcgggttgtt cctcaatgcg    7200
cccccgatgc gcttgacgct cggggtgga agctggcgcc agctgatcca ggccatcgtc     7260
gaggaggagc ggaacatcct tccccacaga aggtatccgg tctccgagat gaaacggcat    7320
tgtgtccagg ccgacctctt cgacgtggcg ttcaactatg tggacttcca cgtctattcg    7380
cgggcgggcg agctggcgtc ggtgggcatc cagacgctca aggcgaagga ggtgacgaac    7440
ttcgggctgt acgtcacctt ctaccagggc tggccgtaca gcaatcagtt cacgctggcg    7500
tatgatccgg atctcttcga ccgggagcag gtcgatcaat cgcccggta ttatctggcg     7560
gcgctgcgtg cgatggcgca gtcgctcgag ggcaggtatg agctgtcatt gctcacgccc    7620
gaggagcggt ccgcgctcct gatctccggt gagccacctg cctccaagcc ggccctggtg    7680
gagaagatct ggagcaatgc ccgtgctcat ccggagcggc aggcactcac ggatgggtcg    7740
cggtccctca gctaccggga actcgcgtca ctcagcgact cgttggctcg tgcgctccat    7800
caggcggagg tgaaacccgg cgatatcgtc gcggtgaacc tccgcaggga cgtccatctg    7860
ccggtcgcgc tcctgggcgt gatgcgcgcg ggggccacct acctgccgct cgacaatcgc    7920
ttcccgctcg aacggcaggc gttcatgttg caggacagcg cgcgaagct ggtgctctgt     7980
gacaatgaga cgcgccccgc ctcgggcgga acggcccggc tcttcaatct ggacgaggag    8040
aagtggcagg accacggcgg cgagcggccg cttccagagc tccacgcgga gtcgatcgcg    8100
tacctgatct atacatctgg ctccacgggc aagcccaagg gcgtgctcat ccgccaccgg    8160
aatctcgaca acttcatcgc gagcatggag aggtctcccg gtttctccca gggcgaccgg    8220
ctgctcgcgg tcacgacggt ggcgttcgac atcgcggcgc tcgagctgtt cctgccactc    8280
tcttgtggcg gtcaggtcgt tctcgcgcca gagcaggtcg gcaaggatgc cacgctgttg    8340
atggagtggt tgaagcggca cgacatcacg gtcatgcagg ccactccagc cacgtggcag    8400
cagttcgtcg acctgggatg gcggggcaaa ccagacctga agatcctcgt tggtggtgag    8460
gctctgcccc cggcactcgc ccgtgggctc ttgacccgct gccgtgagct gtggaacatg    8520
tatgggccca ccgagaccac ggtgtggtcc agctgcatgc ggatcgcgga cagcacccgt    8580
atccggatcg gccagccgat cgcggacacc cggctctatg tcctggatgc ctatggaaac    8640
```

| | |
|---|---|
| ccggctcccc ggcagaccgt gggcgagctg tacatcgcgg gcggaggtgt tgccgcgggc | 8700 |
| tactggcggc ggccggatct gacccgtgag cgcttccagg atgacccctt cttcgggggt | 8760 |
| ccgatgtatc ggaccggcga tctggcgagg atcgattcgc gcaacgaagt cgagtgcctg | 8820 |
| gggcgtacgg accaccaggt gaagctgcgg ggttatcgca tcgagctcgg cgagatcgat | 8880 |
| gcggccatcc aggagcaccc ggacgtcagt cagtccgccg tgattctccg gaggcactcg | 8940 |
| gaacgtggtg atgagctggc cggctactac accctgcacg atgaagcgct ctccaggcgg | 9000 |
| gcgaatgagc tctatggaga gcaggtcgtc cgctgggagg ccgtctggtc ggagacctat | 9060 |
| ggccggtcga aggagaaccg gggcgcgttg aatctggcgg gttggaacag cagctacacg | 9120 |
| ggtcaaccca tgcccgaagc ggagatgcgg gagtggattg acgagacggt cgcacggatt | 9180 |
| cgctcactcg gcgcgaagcg gatactcgag attggttgcg gtacgggtct cctgctggcc | 9240 |
| cgtctggccc ccattgcga gcggtacacc gccaccgact tctctccggc cgcgctggag | 9300 |
| tatgtccaga gcgccatcgt ccctcagctc tctcacctgg actgtgaggt gcaactggtc | 9360 |
| cgcgccacgg ccgacaggtt ggaggggtg gaggatgggc agttcgatct ggtcatcctg | 9420 |
| aactcggtgg ttcagtactt cccgagccgg gagtacctcg acaaggtgct cgcggcggcg | 9480 |
| atccggaaga cccggcagcc gggtaggatc ttcgtgggtg atgtcaggca tttcggcctg | 9540 |
| ggccgcgcgt tccatgcctc catcgccgac taccagtcca agggagcact ggctccggcg | 9600 |
| gccctggagg agaaggtcgc gcagggcctg cggaaggaga cggagctcct gttgtcgccg | 9660 |
| cgctacttcc tctccctgtc ctctctgggc gtcgcccatg cggagatcga gctcaggcgg | 9720 |
| gggacgcacc acaatgagtt gacccggttc cgctatgacg cggtgctgtc cattggccag | 9780 |
| cgtccggagc agctcgagac ccgctggtac gagtgggaaa cccatcctct ttccggggat | 9840 |
| gagctctcga cgaagttgaa gcaggcgggt gagtgctttg gactccgagc cgtcggcaac | 9900 |
| gcgcggctgg cgagagagcg tgagctgctg ggggctcgga gtgacgagac ccagggctca | 9960 |
| gcgggagctg cgcgcgggact cgatccggag cagctctacc ggctggcgga ggctcatggg | 10020 |
| tacagggcca agacgagctg ggcctcggag cacgcctatg gcgcgttcga tgtggccttc | 10080 |
| atcccggccg gaaagaacgc cacgcccctg ttcgagctgg cgcaaggctc ggcacgtttg | 10140 |
| agcaatgccc ccttgctctc acagattgat gtccgggtgg gcgcggagat ccggcgggcc | 10200 |
| ctccagaaga acctcccgga gtacatggtc ccgcgcggc tcgttctcct ggattcgatg | 10260 |
| ccgcacacgc ccaatggcaa ggtggaccgg agcaggttgc cggatgtggg gcgcaacgcc | 10320 |
| gtctcctccg agttcgtcga gcctcggaac gagaacgagc gcaagctctg ccagatgtgg | 10380 |
| caggagttgc tgggcctgga gcgcgtgggc gtgagggacg acttcttcgc cctgggcggc | 10440 |
| cactcgctgc tcgccacaca gctgatcaca cgtatcaaca aacagttcga gtgcaatctc | 10500 |
| agcctgcggg ccctcttcga tttcccgacg atcgagcagc tcgtccggga gattgagcgg | 10560 |
| agccggacgc tccagggccc cgccatgccg aagattcagc gccgcaagaa gaattag | 10617 |

<210> SEQ ID NO 4
<211> LENGTH: 17841
<212> TYPE: DNA
<213> ORGANISM: Artificial
<220> FEATURE:
<223> OTHER INFORMATION: Seq.-ID No. 4: arg3

<400> SEQUENCE: 4

| | |
|---|---|
| atgcatctcc ccgagcttct tcctttgtcg tttgctcaga cccggttgtg gttcctcgag | 60 |
| cagttgttcc ctggccgggc cacgtaccac atccccagt tctggcgtct gcggggggg | 120 |

```
gtgaacgtga gtgccctggt gaaggccttg aagaacacgg cggcgcgtca cgagtccctc    180
cggaccacgt tcgtcaccga gaacggtgag ccgaggcagg ccatccacga ggacatggcg    240
ctggacttcg agtgtgagac gctggatgag cgaggggag agacgctcga ctcctatctc    300
tcggcgttga cggcgcggac attcagcgtc tccgagggc cgctatggcg tgtgcggctg    360
gtgcggacga gcgctcgtga acaggtgttg gccgtcgtct tccaccacat catctgcgat    420
gggtggtcga tggggatctt cagccgggag gtcagccatc attacaacca ggccatcggc    480
gaaagcttgg gtgagctgag tgagcctccc attcaattcg gagacttcgc ccagtggcag    540
cgggagtggt tgcagggcga gcgtctggag cttcagctgt cgtactgggc ggagaaattg    600
aagggtgccc ctgacctgct cgcgttgcca acggacttct cgcggcctcc agcggcgagc    660
aacaagggca agctctacgg gacattcgtt ccccagagg tcgtgcagcg cctgaaggac    720
ctggcccggc aggagaaggc caccctgttc atggtgctca tggctgcctt caaggtgctt    780
ctccgccggt attcgggctc ggatgacatc gtcgtgggaa cgccgattgc caaccggcat    840
tatcccgatg tcgaggaggt gttcgggtac ttcgcgaaca ccctggccct tcgcaccccg    900
ctggagggca gcgcgagctt caggcaggtg ctgcagcggg tgaagcactc gacgctcgag    960
gcgtatgagc atcaggacct tccctcgag ctcgtcgtcg acaagctggg cgtggagcgg   1020
gacctgagca ggcatcccgt gttccaggtg atgttcgctc tcctgaccga aggccgctcg   1080
accctgggtg ttggcaagac ggagcttcgc ctcgaaggac tggaggtgga gagcctgcgg   1140
ggcgtcggtg attgtgccaa gttcgacctg gcgctgctcg ccgaggagac agagcagggt   1200
ctgttcctcg agttcgagta ttcgaccgac ctcttcgaac aggcgaccat cgagcgggtt   1260
gcccgccact tccagaacct cctcgtggag gtggtcgccg ggccgggatc gtcgatcgat   1320
gactacttcg tcctgagtga tgcggaaatc gccgagcgga tcgcctgtct ggatggatat   1380
ggactccccc acgacaccga gatctgtctg catcagtggg tggagcgctt cgcggcacga   1440
acgcctcagg cgatcgccct ccgggatcag acggggtcga tgacctaccg ggagttgaac   1500
gaggaggcga accggctggc gcgctgtctg ctcgagcgtg gtctgggcca tggacagatt   1560
gtcgggctcg ccctccctcg gacgaggag ctcatcgtcg cgatggtcgc ggccttgaag   1620
gcacgagcgg cctatcttcc gctggacctc ggctatccga ccagcgtct gcgcttcatc   1680 ctggaggacg cggagaccgc cgcggtcctc accacccggg cgcatgtcga gtccctgcgg   1740
gggcactgca agcacatcat cgccctggag gatgtggcgg cggaggtcgc tggccagtcc   1800
gcggggaacc tggacctgga ttacgcgtcc ggggatctgg cgtacctgat ctacacctcg   1860
ggctccacgg gcaagcccaa gggcgccacg atctgccacc gcaatgtgac gcggctcttt   1920
cccgatccgg aacctctcta ccggttccgc ccggatgatt gctggacgtt cttccactcg   1980
tgcgcgttcg atctctctgt ctgggagatc tggggcgcgt tgagccacgg ctccacgctc   2040
tccgtggtgc cagccgaggt ggctcgatcg accgacgagt tccgcgagtg gctggtcgcg   2100
catcgggtta cggtcctcaa ccagacgccc tctgcctacg agcagcttct ctcgtatatc   2160 agcaggggagg gcgggagcga cgggctgcgg ctgcacaccg tgatgcttgg cggcgaggg    2220 tggggagagg ccttggcgga cgccatcgc cagctcctac cgcatgtctc cctttacaac   2280
gagtacggtc cggcggagtg cgccgtctgg acgacacacg gctgcgtcta tgatgcggag   2340
acggtgcagt cgtatccgct ggatctgggg atcgcgcaca gccagagtct ggccctcatc   2400
ctgaacgatg gtcatcgtgt taccccgacg ggcgtcgtgg gcgagctcta cctcggcggt   2460
```

```
gagggtgtca cccaggggta ttggaagcgg ccagagctga caaggagaa gttcgtccac    2520
gtctccctt ccggaaaggg caacgtccgc ctctacaaga cgggcgatct cggaaggtac    2580
aagagcaacg gacgtatcga attcatcggc cggcgcgatc accaggtgaa ggtgagaggc    2640
taccggatcg agctgggtga gattgagagc atcctccgga gccttccggg tgtccgggat    2700
gcgctcgtca tgttgagcga gagcggccgt cagctcgtgg cctacgtcgt ggtgggtgag    2760
ggcgggacgc tcacgcagga gacgatcgcg taccagctca aggatgcgct gccagcctac    2820
atggtgcctt ccttcttcgt gctcctggag cgcttcccga tgacgaataa cgggaaggtg    2880
gatcgggccg ccctccccaa gccccacgcg acgacaggtc agtcggttgg ggctcaggcc    2940
ttcgtcgcac ccagcgggcc actcgaggaa ggtatcgcca gtgtgttctc cgagctgctg    3000
gcgatcaccc ccttctccgc ggagggcaat ttcttctcgt tgggtgggca ctcgctgctc    3060
gccacacagg cggcggcgaa gatccatcag cgtctgggca tcgcgtgccc ggtgcgtacc    3120
ttgttcgaga gcagcacccc gagggcgttg gcctggaagt tgggacagga gggcacgaag    3180
caggccgtgg ctggagccgc gctgcccgtg ctccagccga atgagcagga ccgtcaccag    3240
cccttcccgc tgacggacat ccaggaggcc tactggattg gccgcaaggg ggcactgacg    3300
ctcggggaag tctcggtcca ttgctacatc gagtacgaca tggacgagct ggacgtgggt    3360
cggctggagc gggcgctcaa ccgcctcgtt cagcgccacg aggccatgcg tctggtggtg    3420
gaggagagcg gacagcagcg ggtgctgaa agcgtcccct tctacaagat cgaggtgacg    3480
gagctgtccc gggggtcgcg agaggaggag gcacgtgctc tcgccagcgt gcgtgagcgc    3540
atggctcacc aggtgctccc cgcggatcgt tggccgctgt tcgagatcag ggcgagcagg    3600
gctcatggct tctggcgtct gcacgtgagc ctggatcgc tcgtgctgga tgcctggagc    3660
ctgaatctga tcttcaatga gtgggcccgg ctctaccgcg atgaggagac ccggctcgag    3720
ccctgaacg tcagcttccg ggactacgtc atcgccgaga aggcgttcaa gagcacgcag    3780
acgtggcaga aggcgaagga ctactggctc gcacgagtcg ccacgttgcc ggatgcgccg    3840
cagttgccgc tggcgcagag ccagacacgg ctcgacgcgc agcacttcaa tcgcgagcag    3900
aagcgcctga ctcccgaggc cctgcggtca ctgcggaagc tcgcggacaa gcacaaggtg    3960
tccctgtcca gcgtcctggg cgcggtcttc gccgacgtcc tgtcactgtg gagcagcaag    4020
ccgcacttca ccctgaacat gacgctcttc aaccggctgc cggttcatga gcagatcaac    4080
gacatcgccg gtgatttcac gtcactcaat ctgctcgagg tcgactggcg cggaagtgac    4140
gtgccgttca tcgagcgcgt ccgcaaggtg caggagcaac tctggagcga cctggatcac    4200
cggttcttca gcggcgtgca ggtgctgcgt gagctggccc gggctcgcaa caacccggca    4260
gtggccatgc cagtggtgtt cacgtgcctg ctgggatcga ccgaagggga gggacaggct    4320
cacgagtggg agcgtctgtt cccgaacgag gtcttcaaca tcacccagac tcctcaggtg    4380
tggctcgact accaggtcta cgagtcccag ggcgagctgg tggtctgctg ggattatgtc    4440
gagggtctct tccccgaggg actggtgggg gccatgcacg aggcctacat caccagcctc    4500
gagaggctcc tgcgcgagga gagcgcctgg aatgagacgc gcctgacgaa tctccccgag    4560
tcccagcgaa tccggcgtga ggaggcgaac gcgacggcct ggcgtgagcc ggaactgctc    4620
atgcatcagt tgttcgagcg ccaggtcggc gtggctcccg atgcgaccgc ggtcatcgac    4680
agcgagggaa gttacaccta ccgccagttg aatgtggccg cgaaccggat cgcacgaagg    4740
ctcgcgtccc tgggtctgga gccgaacgag cgcgtcgccg tgctggcgcc gaaggggtgg    4800
cggcaggtcg tggcctgtct gggtatccag aaggctggcg ccgcgtacct gcccgtggat    4860
```

```
gggagtgcac ccgccgagcg gatcaacaag gtcctggagc ttggacgggt gagggccgct    4920
gtcgtcgcgt ctctcgagta cggcggggcg ttcggaagca atgccctcat cgtcctcgat    4980
gacgggctgc tggcgcccgc ttccggaacg gaggatgtga gcaatccggc gccgaagcag    5040
accttggcgg acctcgcgta tgtgatcttc acctccggtt cgacgggaac acccaagggc    5100
gtgatgatcg atcaccgggg ggcggtgaac accctcctgg acatcaacga gagattcggc    5160
gtgcgccagg atgacagggt gctcgcgctc tcgagcctga ctttcgacct gagcgtctac    5220
gacatcttcg ggttgctggc cgctggtgga gcggtcgtca ttcctcccga ggcccatgtc    5280
aaggagccgg cggagtggtg tcactggctc gtccagcacc aggtgaccgt gtggaacacg    5340
gtcccgatgt tcatgcagat gctcatggag ttcgtgggcg cactgccagt ggccgaacgg    5400
gaggcgctct cgcggacgct ccggctggtc atgatgagtg cgactggat tcccgtcgag    5460 ctgccgaaca cgatcaagcg ggtcttccaa cgcgaggacc tgcgggtgat gagcctcggt    5520
ggcgccacgg aggcgtcgat ctggtcgatc gcctacgaga tcaaggacgt cgcgaaggac    5580
tggacgagca tcccgtacgg gaagccgctg cggaatcaga ccttccatgt cctggacgaa    5640
gggatgcgtc ctcgtccgga cttcgtgcca ggccagctct acatcggcgg catgggcgtc    5700
gccctcgggt acttcggaga cgaggcgaag acagccgcga gcttcctccg ccatcccac    5760 accgagaac ggctctatcg gaccggagac ctcgggcgct acctggccga cgggaacatc    5820
gagttcctcg gcagagagga tctgcaggtc aaggtgggtg gccaccggat cgagctcggt    5880
gagatcgacc accatctgca caagtgcgga tggatccgtc aggggttgac gcacgtcttc    5940
aagcccgatg gcaggaaccc gcagctcgtc gcctacctgg ttcccgaggg agtgacaggc    6000
aagagcgagc aggagcgtgc ggaagagctc tcgttcaagc tggccgggca caacctcagg    6060
aagacggggg gcgcgggcca tcggctcgtg acggagctcg aacccaaggt ctacttccag    6120
cgcaagagct atcgcgtgtt cgccggagag gagtcccggt tgagccagct ggaggcgtgg    6180
ctgcggagcg cgctgctccc gggcaagcct tcgcgacgg agcggcggga atggacggtg    6240
gcggagatgc tcgcgccgct gctggctctt cgtgaggacg gcctgctgct gccgaaatac    6300
cgctacggtt ccgcgggctc gctctacccg gttcagacct acctcgtcat gggagagggg    6360
cggaaggagc tcgccccgg cgtctattac ctcgaccccg tgaagcacga gctggtgcgt    6420
ctcgcggacg gcgcgctggc ctgctcctgg ttgagccggc gaggtgttcc cctggcgctg    6480
tgcttcgtcg agaagcgctc ggcgatcgaa cccctctatg gcacgcgcag tgacctctac    6540
agcgccatcg aggccgggag catggcggcg ctcgtcgcct cctcgaccgc gcggccggc    6600 atttcgtggc ggacccggtc cgcaccagac ctggaggaac tggcgcccgt cgtcctggag    6660
tccgctgact gctccgcgat cgcggtcctc gagccccgcg agctccaggc cctcgacgag    6720
cgcggcaagg actccgatgt ctccgtcctg atgtacgtga tgcgagggtc ggagcatggc    6780
ccacggacgg gttggtaccg ctggtccggg gaccacttcg aggccttcag tgctccggcg    6840
ctcagcatgg tgccgtcgaa ccccgcgaac tggtccatct gccagaatgc gtccttcgcg    6900
ctcttcgtga tggagggaaa ggcacagccg cggacctcct cggcgctctt cacggggcgt    6960
ctgatccagt ccttgatgga gaaaggcgtg gggctgggcc tgggtggctg ctcgatcgga    7020
gaaatggacc ccgagggcgg gcggctcctg agagaagtgc atgacggtga gttcgttcat    7080
gccttcttcg gtgaccggt ggattccgcc cagatctccg cggtgggcac ttccgaggcg    7140
gagccgttcg agcaactcgt gaagcggaag acgcgctcgg tcctcgaggg ctcgcttccc    7200
```

-continued

```
gggtacatgg ttcccgacca ctacgtcctg ctcgacagct tcccctgtc gagcaatggc      7260
aaggtcgatc gttcccggct cgccgcccg gagttggaga gacccagaa gcaagacgcc       7320
ctggtgcggc cctggaacag caccgaggcg gtcatcgcga gcatctgggc gcagttgttg     7380
ggcgtggagc cggacgcggc cgacaacttc ttcgcgctgg gcggccattc gctgaccgcc    7440
acgcagctct gtacgcgtct gcgagaggcg tttggcgtag aggttcctct gcgcgaggtc    7500
tttggtaggg cggatgtgcg gtcccaggcc agcatggtcg agggcctgct gaaacagcac    7560
gtcggtcgtg gggcttcgat tccccgcaga gccgggacgg gccggtccgt ggcgtcgtat    7620
gcgcagaagc ggctctggtt cgtcgagcaa ctggcggaga acggttcggt ctacggaatg    7680
ccggtcgcgg tcgcgctcca gggccccatg gactgggatg ccttcaagaa ggcgctcgcg    7740
ggggtcgtgg cgcggcatga aatccttcgt acgaccttcc acatggagca ggggagttg     7800
tggcaggtga tccacgagga gatcaccgcc cccttcgaga cggagcagtg ccccgagggc    7860
tccgtgatgg agaagcgcgc gtatgtgcgc aagcggatgc gcgagctggc gcgggtgccg    7920
ttcgacttga gcaccggtcc gctgctccgg ttccatgcgt tcgcgctgtc cagggagcag    7980
cacatcctgt tcggcgcgat gcaccacatc atctccgatg gctggtccgt ggatgtcttc    8040
cagtcggagt tgagcgctct ctacaacgcg gcgctgagcg ggagcacgcc ccagttccag    8100
gagctctcca tccagtacgc ggatttcgcg gcctggcagc gggattggct ccgtgggccg    8160
cgctccgaga agcagctcca gttctggaag gactccctcg cgggtgctcc ggagctcctc    8220
caactcccca ccgatctccc caggcccgaa cgtcagagct ccgcggtgg cgtggttcgc    8280
aggacgctcg atgcgcagtt gaccgcggag atcgactcgc gctgccgtga gtgggcgtc    8340
acccccttca tgttctatct cgcggcctac aaggtgcttc tgtccaagct gagtggacag    8400
gcggacattc tcgtgggcac cccggccgcg aaccggcact actcccaggt cgaacgcctg    8460
attggttact tcgcgaacac gctggccatc cggagccgcg tcgagggca gcggagcttc    8520
gccgagtatg tccaggcggt tcgtgaagga gtgctggcgg cgaacgagaa ccaggacgtt    8580
cccttcgagc aggtcgtcga gagcctccag cttcgtcgca gtctggcgta ccagcctgtc    8640
ttccaggtca tgttcgtgtt cgagaacgag gggcgctcca gcctttcgtt gaacggcgtg    8700
agcgtgcagc cggtatccct ggacgcgcag gtcgcgcgct tcgatctgac gctgctcatc    8760
cgcaacgcgg gagacgcacg ggagatctcc ttcgagtatt cggaggacct gttcaagcgc    8820
gaaacggccg ctgaatggct cgatggagtc atcagcctgg tggaagccgc gacgcgggac    8880
agcagccagc cctggccgc gctgcccctcg atgtccgagg ccacgctgga gaaggtcctc    8940
ggccagttca gccggggaga gcgcacggcg agccccaagc tgtgtctgca tgagcagttc    9000
gagcgtgtgg tggcccggca gggagagctc tgcgccattc aaacgcctcg cagtgagatc    9060
acgtacgagc agctcaacga cagggcgaac cgcgtggcgc gtctgttgtc ctcgcatggg    9120
atccgcaagg gggacgtggt cgcgctctgt ctgaagcgct cgccggatct gttcgcctgt    9180
tacctggcgg tgctcaagct gggtgcgtg tatgtgccca tcgatgggga gtacccggaa     9240
cgccggatcc agcacatgct gaccgacgcg ggcgcgaagc tcgtcgtggc ctcccccgtc    9300
tatgcggaca agctgggaac ggccccggtc ctcgtgacgc tggaggagtg tgaggaccgg    9360
ctggagtcga tggcgggctc caacctctcc gtcaaggtct cccggagga tgtggcgtac    9420
atcatctaca cctcgggaac gaccggtctg cccaagggcg cgcgggtcaa gcatcgcggt    9480
gtctccaacc tcgtgctcgc gcagcaggag tacttcgtgg cggggccgg aaagcggctc    9540
ctgcaattcg cctcgtgcag cttcgacggg gccatctggg agtggacgac cgcgttgctc    9600
```

```
aacggcgcga ccctctgcct cgtcgcggag agcagcgccg aggtcgtcag ccgcctcacc   9660
cgccgcgacg agcagccgcg gatcgacatc gccgccctgc ctccgtccgt ggtcgccagc   9720
cttccggacg attgcctgcc agggctcgag gtgctgctgg tcgcagggga gagctgcccg   9780
cggggtgtgg tggaccgctg gtctcggcgt acgcggatgt tcaacgccta tggcccgtgt   9840
gaagccagtg tgacgtcgac gatgttcgag ttcgatggca ctcgcggtgc gtcgaccatc   9900
gggcgtcctc tgcgcaactg cgatgtctac atcctggatg agcggatgct ccctgtccct   9960
ccaggagtgg ccggagagct ctgcatcgcg ggactgggac tcgcggaggg gtaccacaac  10020
cgggcggagg agacggagcg gcggttcgtc gaggcgagca tcggctcgga gaccgtgcgg  10080
atgtaccgca cgggtgatcg tgggcgttgg gcgagcgacg gaacatcga gttcctgggc   10140
cgcctcgaca atcagatcaa gatccgcggg attcgcgtgg aaccggatga ggtccgcacg  10200
cagctcctcc aggtgcccgg tgtggcccag gcggctgtcg tcgtcgatcg ggaggggcag  10260
gagacgcggt tgctcgcata cgtcgtggcc tcgccggagg tccgctcga cctggagcac   10320
gtgcgcaaac ggctacgggc cgcgctgccc gaggccctgg ttccctcgtg gttctgcccg  10380
gttgctacgc ttccgatgac gctcaatggg aagctcgatg tggaggccct tcccaggcca  10440
ggcgaggagc ggaccgaagc gcggttcgaa gagggtgcca cggaggtgga gcggaagctc  10500
caggccctca tcgcgggcgt gctggagggc aggcggctcg gccggcacga cgacttcttc  10560
cgaaacggag gtcattcgct caaggcgatc catctcgtcg cggagatccg gaaggaactc  10620
ggtgccgagt tggcggtgaa gaccatcttc gacgctccga cagtggccga gctggccgg   10680
gtgatcgaat ccgaaagaag acaggaaggt ccgaccgcct cgcgtccccg cctggagggc  10740
tcccggttca cgctgtccgc cctgcagcgg cagatgtggc tggccgagaa ggtgttgcag  10800
cggagcggcg cctacaacat gccgctctgc ctggagcttc gtggcgcgcc ggatgcttcc  10860
gccctgcaga acgccgtcga catgctcctg cagcggcatg gtgtcttgcg gtggcagttc  10920
aaggaggagt cgggcgagcc ctatgcggag gattgtggcg tcgacacggt gacgctcgcc  10980
acgctcgact ggagggagct ggggcagcag gagaaggaca ccgcactcgc cgggctcatc  11040
gcgacgccgt tcaacctgtc tcagggggcct ttgtggcggg gcgcgctcat ccgaatcgga  11100
gaggagcgct tctggctcct gctctgcgcc catcacctgc tggcggatgg atggtcgctg  11160
ggactccttc tcgagagct ggccgagctc tacaacgcgc gagtaggtca tggcacggcc  11220
cggttgccgg cgcctggcac cgagtactcc cgctatgtcg agcagagtgt cggggatgag  11280
cgggagctcg agcgtcaact cgagttctgg cgtcatcagc tcgagggtgc tccgcagcgg  11340
ctggcgttgc ccatggagtt gaagcggtcc ctgtcacccg gaaaggccgg tgccgtcgac  11400
ttcgaggtgg gtccggagct gaccgctcgt ctccgtgagc tggcggaaca gcggggcagc  11460
agcctcgtca tggtgctcat gagcacgtat caggccgtgc tcgcccggtt cgcgggcgcc  11520
gatgacgtgc tcatcggaac gcctgtcgcg tgccggcaca agccggagct gttgaacacg  11580
atcgggctcc tggtgaatac cctccccatc cgtttgagcc tcaccccgcg tacgacattc  11640
gccgaggcgc tcgcgcaggt ccggcagcgg ttgctcgagg ggatggctca catggacgtt  11700
cccttcgagc gcatcgtctc cgcggtcgca caggagcgcg agcccggtgt ccccgcgctc  11760
tgtcaggcga tgttcgtctg ggaggagggc gctcgtggtg acctgaagct cggggtctc   11820
gacgtctcac tgaaggcgac cccggtcacc tccgcgaaat cgacctcgc cctcttggcg  11880
agcgaacagg acggccgtgt cacggggcgg ctcgagtatc ccgaggggct ctatgaccgg  11940
```

```
gcatccgtgg agcagctcgc cctcagctac gtgaagctgc tctccgagat ggcgaaggat   12000
ctggagggga tcgtcgcgca ggccgagctg atgtcccagg agcagcggcg caattggag    12060 gcgtggttcg agtaccggcc ggagttcctc gaggctccca acctccacac gctgatcgag   12120
cgtcaggcgg ccaccgcgcc cgcgtcgtca gcgctgcgct acaagggtga gagctacagc   12180
tacgagtggt tgaataccca ggccaataga ctggcgcgct acctcggggc tcggggcatc   12240
gggcgcggca gcgtcgtcgc gctgtgcctc gcgcgctcgc cggagctcgt ggtcgcgtgg   12300
gtggccgtgc tcaagtccgg ggcggcgttc gtctcgctcg atccccatat gcctcaggcc   12360
aggaggcggt tcatcctgga tgacagcagg accgcgctcg tgctgtcgca cgccgccttc   12420
gcggaggagc tcgggaccgg tacggacatc gccgtctggg aagaggtggc gaagcagctg   12480
accgggctcc cggcgagaaa cctggagctg gaggtccgtc aggaggagct ggcgtacctc   12540
atctacacct cggggaccac gggcaatccc aaggggacca tgctggcgca ccgggggatg   12600
atcaacctgg cggtcagcga gaagcagcgc agcggaatgg gtcctcagag caaggtcctc   12660
cagttcacca ccgccacctg tgacggttcg atctgggagt ggacctcggc cctggtgaat   12720
ggcgccgagc tctggctgtt ggatgcgagc aatccgcagg agcaggtggc tcaggccatg   12780
caactcctgt cggagcctgg gattaccacc gtcgcgctga cgccgagtgt ggtggagctc   12840 ctcccccccgg aagcgatgcc cacggtgcaa tcactcaccc tggcgggtga ggcttgcccg   12900
ttggcgctgc tggagaagtg gtccgcgagg atccccggag tcgccaacgt ctatggtccg   12960
accgaagcaa cggtgaccac ggccacattc cccttccggc ccggctatcc cgcgaacacc   13020
atcggcaagc cgctggcgaa cgtgcaggtc tacatcctgg atgagcacgg caagctgctc   13080
cctccaggcg tcatcggcga gctctgcatc gcgggtgtgg gtctggctct gggctatctg   13140
gatcgcgacg agctgacaca acggaagttc gtcacccatc cgattggacc tcgaggcgag   13200
cccgttcgcg tctaccgctc gggtgacctg gcccgctatc tgccggatgg ccatatcgtg   13260
ttcgagggcc gcaggacaa tcaggtcaag gtgcgaggct atcgcgtcga gctggatgag   13320
gtggcctggg tcctcaagca gcacccgcag gttcagcagg cctcggtgat cgtctcgcag   13380
gccgggaagc ggtatccgta tctcgttgcc tacgtcgtgc cgcgcacccc gccgtcttct   13440
ccggccagcc tgcgggcgga gctgcgtgcg tacatggccg agcggttgag ccactacatg   13500
gttccggagg cctacgtctt catcgagtcg ctgccgctca atcgctccag catgaaggtg   13560
gaggtctcgc tgctgcctcc tcccgagggg gactccttcg ttcgtgacac gctggtgccg   13620
ccagagacgg ccgtggagaa ggagctggcc accctgtgga tggagctcct cggtgtgggg   13680
agcaccggcc gtcatgacag cttcttccgg ctcggcggca actccctgct cgccgtcaag   13740
ctgggtcacg ccatcggcga gcggtggggt tgtgacatct ccctcccacg tatcttcgag   13800
aacgacacgt tggcggcgct cgcgcggtgc atcgaggccg acgagagaag gagccatgac   13860
ctccagctcg ccagggccag tgagcgcgag agctggcccc tctcttttgc tcagggacgg   13920
atgtggttcc tcgagcatct gacccagggg agctccgcct accacgtgcc actcgtcctc   13980
cggctcatcg gcaaggtctc gttcgagcgg ctcgcccagg ccttgagcgc gttggtggtt   14040
cgccatgagg tcctgcgcac cgcctatgtc gaagacggga acacgctgag ccagaagatc   14100
ctcgacgccg ttgccgtcga gatggcgagc agcgacctga gcccgatcgc tcccagtgaa   14160
cggcaggcgg ccgtggatcg tctcctcggt gcggatctcg gcggccgtt cgcactggcc    14220 gcgggcgaga acgtgagggc acggctcgtg cgcttctcgg aggacgagca cctgctctgc   14280
ctctgcctgc accacatcgc gttggatggt tggtcgatca gcgttcttct gcgggagctg   14340
```

```
ggttcgctgt accggggggca gccactccaa ccccctgccgc tgcggtacgt ggacttcgcc   14400
tgctggcagc gcgacgtcct cgagaagcgc ttcgcggagc agctggacta ctggaaggcc   14460
gagctgcggg agctcccgcg gcagctcgag ctgccatggg atcatccccg tccgcccagg   14520
caggactacc gtggtgcttc cgcgcgtcgc ccactgtccg ggaactacg agccgcgttg    14580 aagcaggtgg ccgagcgcta cgatgtgacc gacttcatgc tctacctgac gtcgttccag   14640
ctctggctcg gacggctcag caacagctgc gatgtggtgg tcggcacacc ggtagccaat   14700
cgccactaca acggcgtcga gtccatcgtc ggcctgttcg tcaacacgct gccgctccgc   14760
cttcggtatg acgctccga gacgttcggc ggcgtcgttc gcaggatgaa gtcgaaggtg    14820
ctggaggcgt acagccacca ggatgtgccc ttcgagtacc tcgtggacca tctggaagtg   14880
cccagggagc tgagccacgc ccccatcttc caggcgatgt tcctgctgca ggacgagtcg   14940
gggcgcgaga tcgacctggg tgacgtccag gggcggatcg ctcccgtggc tggcacggtc   15000
gccagattcg atgtgtcgct cctggttgag ttcgatgagg aaggcgcgga gctgaatctc   15060
gagtacgcga gcgctctctt caggcccgag accatcgacg agtggttgga gagcttcgag   15120
ctgttcttgc gcgcgatcgc ggcggacgcg gaggctccgg ttcggcggtt cgagctgttg   15180
ccgccgcgga tgcggtcctt cctgtccgag gtgggcaccg gaccccggcg agagtatggg   15240
agccttcctc tgcccgagct cgtagcggag caggcgaagc atggcggaca gcggatcgcg   15300
gtcgagggtg tccgggaatc gtggacctat ggtgagctcc tcgccgccgc ggagcgtgtc   15360
gcggccggcc tgcagcgccg cggggttcgt cctggcgacg gggtggcgat cgcgctgcct   15420
cgcgaccatc ggttgccctc cgccatgctg ggcgtcctga aggcaggtgc cttctacgtt   15480
cccctggatc tcacgcatcc ggagcgcagg ctccagtaca tcgcggggga tgcgaaggcg   15540
cggttcgtca tcacgggagg cgagacccgg ttcggattcg acatccctcg tgtgaacctg   15600
gacgagctgt tggaggagac ctcggaagcg cggccggtgc ccatcgcacc gtcgagcctg   15660
gcgtacgtca tctacacctc gggctccacc ggtgaaccca agggcgtcat ggtgagccac   15720
gccagcctct cgaacttcct gcacgcgatg gtggaggagc tcggcttcgg gccggatgag   15780
cgtctgctgg ccatcacgac gatcgcgttc gacatctcgg gcctggagct gttcctgccg   15840
ctcatccgcg gggctcgcgt cgtgatcgcg gacgaggact ccacgaggga tccgcggctc   15900
ctgtccaggt ggatcgacga gcgacggatc tccgtcatgc aggccactcc ggcgacctgg   15960
cggatgctca tggatgcctc ctgggtggca cctggatcct tcaaggcgct ggtcggcgga   16020
gaggcgttgc cgcggaacct ggcggacttc atgacgagcc gggtgagcca ggtctggaat   16080
gtgtacggtc ccaccgaggc gacgatctgg agcacgatcg cgcggctgaa gtcgggtgag   16140
cgggtccaca tcgggcggcc cctggcgaac accgaggcct tcgtgctcga tgatgggttg   16200
cgagccgtgc ctcgcggaac cctgggcgag ctccatctcg gtggttccgg tctggccacg   16260
gggtacctgg gtagggagga gctcacccgg cagaagttcg tgcatcaccc ggagctcggc   16320
cggcggctct acaagaccgg agacctcgcc cgggtcttgc cctccggcga catcgagttc   16380
gtcgcccggc gggatgcgca gctgaagatc cgtggcttcc ggatcgagcc gggagaggtc   16440
gaggccgtcc tgagcagggt ccccggggtg gcgcgagtca cagtcctgcc cgtggggagg   16500
ggggagggca cccagctcgc cgcgttccta ttgacggggg atgagcggct ccaggcccag   16560
gcgagagcac tcgcggagca gcaactgccc gaatacatgc ggcctgcccg gtacgtggtc   16620
gtgcccgagt tcccgctgac gcccaacggc aaggtggata cgaaggcgct gcgggcgctg   16680
```

```
gtctcggagc aggtggaaga ggcggcgggt tccgcgccga aaaacccgat cgagttcagg    16740
atctcccggt tgtggtcggc gctcctgggc gtccgccatc cgggcacgcg ggacaacttc    16800
ttcgcgctcg ggggcacgtc actggccgcg gtccggctcg ctcgcgagct ggagagcgaa    16860
ttcggtatcg aggtgcgggt cggtgacatc ttccggaagc ccacgatcgc ggagctcgcg    16920
ggtctggtgg agacgcaagg ctcggagcgg gtcctcgagc ccctcgtcct cttgagccgg    16980
gagcagcaga agccgcccct cttcgtgatc caccccgcgg gtgggatggc gtactgctac    17040
gccgggctcg cacaggaact ctccggattc acggtccacg gcctgaatca accgcactac    17100
tacgagctgg agcaccgctt cgagacgttg gcggagatgg cggcggatta cgtcgccaga    17160
atcaagcggc tccagccgac cggaccctac cgtctcctgg gctggtcgtt tggtgggacc    17220
ctggcctatg agatggcgag gcagttggag caggcgggag aggccatctc cggcgtggtg    17280
atgctggacg cgcatcacgt ctccgccgctg ggcgcgaacc tgccaacggt cgatgtctcg    17340
gcgatgctgg ccaacctggg tctgggcggc gagatggccg acccctacct ggagaaggac    17400
atccgcgaga gcgagcggct ctcccgggac tacaaggcct cgcccgtgcg cttccccgtg    17460
ctcctgttca agcccaccga gcggaatggg ttcgaggaga ggctttacgc ggacctctac    17520
aacggttgga gggagtgcgc ggagaactcc gtggtgcgca gtgtcaccgg cgatcatggt    17580
ggagtcctgg accggcgcaa cgtcagcgag ctggccaggg tcgtcgaggc cttcctgtca    17640
ggaggttacg gagtgctcct gcgtgaagcg gttcagcccg ccctcgcgtt cgcgctcgcg    17700
gagcgtgacc gtttcgtcgc caggcggctg gtggagcaac tgccgcggga tctggtggag    17760
cgctggctga agtcggcgat cgactgtctg ccggagtcag tccggccaga ggggtcgttc    17820
gttcaggcgc tgctcgaata g                                              17841

<210> SEQ ID NO 5
<211> LENGTH: 1011
<212> TYPE: DNA
<213> ORGANISM: Artificial
<220> FEATURE:
<223> OTHER INFORMATION: Seq.-ID No. 5: arg4

<400> SEQUENCE: 5
atgattccca gcagcctcga aaaggccatc tacggtgtgt atgcaacgca tgccctgcac      60
ctggcggaca agcacaacgt cttcgcgtat ctggcggaga agggcgccgc ggcgcctgga     120
gagatcgcga aggcggtggc ggtcgatggg gagaccctcg agaggttgat gctcgtcctg     180
ggtgccttgg agctcgtcca ggccgggtcc gacgggaagt accggttgcg tgaggggatg     240
gggccctatc tggacaagaa ggatccccgc tacgtgggtg gtttcgtcac gcatctcatc     300
aacagcacgt ctggccggat gggacacctg gatgcatacc tgtccaaagg caaggcggtg     360
gtggacgcgg ctctgccttc gccgttcgac gtcatctaca aggacgaggc gtcgacgaag     420
gagttcatgg acgccatgtg gcagttgagc ttcgacgtct cacggagct cgtgaagctg     480 gcgggtctgg attcctgccg gcagctcgtg gatgtgggcg gcgcgagtgg gcctttctcg     540
gtcgccgcgc tgcagcactc cagggagttg cggtccaccc tgttcgatct gcccaaggtc     600
gggcgctacg tcgatgagac ccgccggacc tacgggctcg aggagcggct gcgtttcgtc     660
ccgggcgact tcttccggga ggagctcccg gaggggact gttttcgcctt cgggtacatc     720 ctctcggatt gggacgatgc gacatgtctc gagctgcttc gaaaagccca tcgagcgtgt     780
agggcgggcg ggcgcgtgct cgtgatggag cggctgttcg atgaagacaa gcgagggcct     840
ttcgcgaccg ttttcatgaa cctctcgatg catgtcgaga cccagggcag gcacaggacc     900
```

```
gcccgggaat acgtgggcct gttggaggcc gcgggtttcc gtgggtgcga ggtgcggcgc    960
tcctcgcgcg acaagcatct ggtcatcggt ttgaaacacg tcaccacctg a           1011
```

<210> SEQ ID NO 6
<211> LENGTH: 1152
<212> TYPE: DNA
<213> ORGANISM: Artificial
<220> FEATURE:
<223> OTHER INFORMATION: Seq.-ID No. 6: arg5

<400> SEQUENCE: 6

```
atgcgggttc acctgccagg cgagtgcgaa gacattgtcc ggctgcaaaa gagagcgggc     60
cgtgctgccc tgctggagtc cgagtgcgag gcgctgtcgc tgctgtatga ccgggtctcg    120
gtggagggcc cctccgagga ggaggagatc ctggccctgc tgacgaggcc cttcagccgg    180
cgtctggcca tcccggagta ctaccagtac accagcctgc acgtgtacgg ctggttcctg    240
tcccactacc ggagggatcc gctccgcggg tccctcgtcg cactgcacac gaccctggtc    300
gatctgctgt cggtggagga gcagggagcc cggctcggcg aggccacgcc ggcctatatt    360
catgagcgga ttcgcgggtt gcgaggtctg ctcgggcagc tcgatgagat ccccgtggat    420
cggaacgggc ccctgttcgt cgcggacgtg ctcaagggca gcaagaagga tgctcaggag    480
cagtggcgcg ccttcgtcct ggcgcgttgt acgggattcc cgaagtcgca agtacacgat    540
gagtacatct tcctccggtc ggtccacgcc tgtgagatcg tcttcttcca ggtgcggtgg    600
ttggccctgc gcatctcgga gatgatcgcc gtggaccgga aggaagccgt cttcctcctg    660
gggcagttga cgagcttcgc agagctcctg aacaagatct tcgacgtgct gaagaccatg    720
tcgcccgagc gtttcatgag ctttcgagca caaacgggaa acgccagcgc agttcagtcc    780
ctgaatcatc acgcgatgga gatcgccgtc tttggcttcg accccgggcg ggcgagcgtg    840
ttcgatggct tcgagcatct gaagcggttg aacgagccgc tgtttcggga gcacgcgtcg    900
ttgcggagtg tcgtcgaagc cacggcggac ggggcgctgg cggaaggatt cgcgaaactc    960
gataggtgtc tcctccgctg gcggggaggg cactatgggt tcgcccgaaa gtacctgccg   1020
gttgacatca agggctctgg aggaacggag ggggctccgt atctcaagag gttcatcaag   1080
aaggacgact gtcagtcagg cgggcagcgg ccgggtaccg acagcgagct ggcgcggttc   1140
ttcttctgct ga                                                      1152
```

<210> SEQ ID NO 7
<211> LENGTH: 682
<212> TYPE: PRT
<213> ORGANISM: Artificial
<220> FEATURE:
<223> OTHER INFORMATION: Seq.-ID No. 7: Arg1

<400> SEQUENCE: 7

```
Met Cys Cys Ser Arg Tyr Ala Ser Arg Ala Phe Leu Met Gly Gln Thr
1               5                   10                  15

Asp Leu Leu Leu Leu Asn Ala Ser Asn Leu Pro Gln Leu Pro Ile Tyr
            20                  25                  30

Pro Tyr Ala Phe Val Gln Val Ser Ala Ile Ala Arg Arg Phe Gly Leu
        35                  40                  45

Ser Val Arg Arg Leu Asp Leu Leu Gln Val Arg Arg Glu Phe Trp Arg
    50                  55                  60

Pro Met Leu Arg Glu Leu Ile Gln Arg His Arg Pro Arg Met Val Gly
65                  70                  75                  80
```

```
Ile His Leu Arg Gln Gln Asp Thr Val Leu His Phe Asp Tyr His Asn
                85                  90                  95
Pro Gln Met Gly Val Met Ala Gly Arg Tyr Phe Pro Val Gln Asp Thr
            100                 105                 110
Arg Ala Leu Ile Glu Val Leu Arg Glu Val Gly Asp Met Pro Ile Thr
            115                 120                 125
Met Gly Gly Phe Gly Phe Thr Ser His Ala His Leu Leu Leu Asp Tyr
130                 135                 140
Leu Gly Ala Asp Phe Gly Val Gln Gly Asp Pro Asp Gly Phe Phe Ala
145                 150                 155                 160
Arg Phe Glu Asp Val Val Ala Arg Arg Asp Leu Glu Ser Val Pro Gly
                165                 170                 175
Leu Ala Tyr Arg Arg Asp Gly Thr Tyr Gln Phe Asn Pro Arg Gly Phe
            180                 185                 190
Tyr Pro Pro Ala Ala Glu Arg Glu Tyr Thr Asp Glu Ile Val Asp Glu
            195                 200                 205
Leu Ile Ser Phe Tyr Gly His Ala Gln Leu Tyr Gly Ser Asn Pro Pro
            210                 215                 220
Thr Val Ala Val Glu Ala Met Arg Gly Cys Pro Phe Ser Cys Gly Phe
225                 230                 235                 240
Cys Leu Glu Pro His Val Lys Gly Arg Arg Ile Ala Tyr Arg Asp Ile
                245                 250                 255
Glu Thr Ile Val Ser Glu Leu Glu Phe Leu Leu Ser Arg Asn Leu Arg
            260                 265                 270
Arg Phe Trp Phe Val Ala Ser Glu Leu Asn Ile Gln Gly Ser Glu Phe
            275                 280                 285
Ile Leu Lys Leu Ala Glu Arg Val Ile Arg Leu Asn Glu Thr His Pro
            290                 295                 300
Gly Ser Pro Ile Glu Trp Ser Gly Phe Thr Leu Pro Arg Phe Asn Glu
305                 310                 315                 320
Ser Asp Leu Arg Leu Leu Gln Arg Ala Gly Tyr Ala Gly Ala Leu Asn
                325                 330                 335
Asp Ile Leu Ser Leu Asp Asp Glu Asn Leu His Arg Met Arg Val Pro
            340                 345                 350
Tyr Arg Ser Gly Gln Ala Ile Thr Tyr Leu Lys Ala Met Ala Lys Met
            355                 360                 365
Ala Glu Glu Glu Ser Gln Ala Gln Ala Thr Ser Pro His Gly Val Glu
370                 375                 380
Gly Leu Arg Gln Arg Leu Ala Gly Tyr Phe Thr Leu Phe Leu Gly Asn
385                 390                 395                 400
Ser His Ala Asp Glu Arg Thr Ile Arg Arg Ser Leu Gln Gln Val Asp
                405                 410                 415
Glu His Gly Leu Arg Glu Lys Tyr Arg Gly Ala Phe Val Met Ala Ala
            420                 425                 430
Thr Arg Val Tyr Asp Ile Glu Gly Lys Tyr Ile Cys Ala Thr Ser Glu
            435                 440                 445
Glu Glu Ala Lys Ser Ile Ile Ser Tyr Asp Glu Arg Gly Glu Arg Pro
450                 455                 460
Phe Asn Leu Leu Trp Pro Ser Phe Tyr Tyr Pro Arg Phe Leu Met Gln
465                 470                 475                 480
Arg Leu Gly Ser Thr Ala Glu Ile Leu Lys Phe Phe Ser Phe Val Gly
                485                 490                 495
```

Asp Thr Phe Leu Ser Leu Ala His Arg Met Arg Lys Asp Trp Asn Trp
            500                 505                 510

Phe Leu Ser Arg Asn Thr Ser Val Glu Gln Leu Arg Glu Trp Leu Ala
        515                 520                 525

Gly Ala Ser Ser Val Pro Leu Gly Ala His Glu Ala Pro Pro His Val
    530                 535                 540

Leu Glu Lys Ala Ala His Val Leu Gly Glu Pro Arg Thr Pro Ala Leu
545                 550                 555                 560

Val Ser Met Met Ala Pro Glu Pro Gln Lys Pro Leu Trp Asn Glu
            565                 570                 575

Val Ala Arg Val Leu Leu Glu His Leu Phe Arg Val His Gly Lys Ser
        580                 585                 590

Val Ala Ala Val Thr Thr His Leu Gly Ile Gln Ala Asp Glu Arg Gly
    595                 600                 605

Ile Pro Arg Leu Ser Glu Tyr Arg Leu Met Glu Arg Leu Tyr Gln Arg
        610                 615                 620

Tyr Asp Ser Val Glu Gln Leu Ile Glu Gly Ala Gly Ser Cys Leu Asp
625                 630                 635                 640

Val Thr Gly Asp Ser Leu Ala Met Leu Tyr Leu Gln Trp Leu Leu Tyr
            645                 650                 655

Ala Asn Asn Val Thr Ile Arg Pro Gly Tyr Arg Glu Leu Leu Phe Glu
        660                 665                 670

Pro Pro Val Glu Pro Ala Ser Ala Val Gly
            675                 680

<210> SEQ ID NO 8
<211> LENGTH: 3538
<212> TYPE: PRT
<213> ORGANISM: Artificial
<220> FEATURE:
<223> OTHER INFORMATION: Seq.-ID No. 8: Arg2

<400> SEQUENCE: 8

Met Ser Arg Cys Glu Gln Arg Leu Arg Asp Arg Thr Lys Met Asp Thr
1               5                   10                  15

Arg Lys Gln Ala Ser Gly Glu Val Cys Phe Leu Asp Leu Phe Leu Arg
            20                  25                  30

Gln Ala Glu Leu His Pro Ser Lys Ser Ala Val Glu Cys Gly Ser Ala
        35                  40                  45

Arg Leu Thr Tyr Gln Ala Leu Val Ala Arg Ser Glu Arg Leu Ala Ser
    50                  55                  60

Ala Leu Gly Ala Ser Gly Val His Pro Gly Asp Arg Val Ala Val Val
65                  70                  75                  80

Leu His Arg Gly Leu Asp Thr Val Ala Met Val Ala Val Leu Arg
            85                  90                  95

Thr Gly Ala Val Tyr Val Pro Ile Asp Val Thr Trp Pro Asp Asn Arg
        100                 105                 110

Ile Arg Tyr Ile Leu Asp Asp Leu Gln Pro Gly Ala Ile Leu Cys Asp
    115                 120                 125

Glu Glu Asn Ser Arg Arg Ala Cys Phe Thr Ser Asp Asp Arg Leu Leu
130                 135                 140

Leu Ala Ser Ser Glu Gly Thr Gly Gly Ser Asp Phe Arg Pro Gly Pro
145                 150                 155                 160

Met Ala Pro Ala Tyr Phe Met Tyr Thr Ser Gly Ser Thr Gly Arg Pro
            165                 170                 175

```
Lys Gly Val Val Leu Ala His Gly Gly Leu Ala Ser Arg Leu His Ala
            180                 185                 190

Phe Ser Arg Ala Tyr Glu Ile Gln Pro Glu Asp Arg Phe Leu Ala Leu
        195                 200                 205

Ser Ser Val Ser Phe Asp Val Ser Val Leu Asp Leu Met Leu Pro Leu
    210                 215                 220

Val Asn Gly Cys Cys Thr Phe Ile Ala Ser Asp Glu Gln Arg Arg Asp
225                 230                 235                 240

Pro Asp Ala Leu Arg Asn Leu Phe Glu Glu Arg Ala Leu Asn Val Ala
                245                 250                 255

Phe Ala Thr Pro Thr Thr Met Arg Ala Leu Val Ser Val Gly Trp Lys
            260                 265                 270

Gly Ser Pro Arg Thr Lys Ile Leu Cys Gly Gly Glu Ala Ile Pro Gln
        275                 280                 285

Ser Leu Met Asn Glu Leu Val Ala Arg Gly Arg Leu Phe Asn Val Tyr
    290                 295                 300

Gly Pro Thr Glu Ala Thr Val Ala Val Thr Ser Pro Glu Leu Phe Ala
305                 310                 315                 320

Gly Asp Ser Val His Leu Gly Arg Ala Leu Pro Gly Val Glu Leu Leu
                325                 330                 335

Val Leu Asp Glu Ala Gly Ala Ile Cys Gly Pro Arg Gln Pro Gly Glu
            340                 345                 350

Leu Val Ile Gly Gly Ile Gly Val Ala Leu Gly Tyr Trp Lys Asn Asp
        355                 360                 365

Glu Leu Thr Arg Lys Lys Phe Val Asp Gly Lys Tyr Arg Thr Gly Asp
    370                 375                 380

Leu Val Ser Trp Gly Glu Asp Gly Asn Leu Tyr Tyr His Gly Arg Met
385                 390                 395                 400

Asp Glu Gln Val Lys Leu His Gly His Arg Ile Glu Leu Leu Glu Ile
                405                 410                 415

Glu Glu Met Ala Arg Ser Leu Gly Leu Val Arg Asp Ile Lys Val Leu
            420                 425                 430

Ile Gln Glu Asn Ala Ala Ser Pro Arg Leu Val Ala Phe Phe Ile Gly
        435                 440                 445

Asp Glu Ala Ala Ala Gln Ser Leu Arg Arg Arg Leu Ala Ser Glu Leu
    450                 455                 460

Pro Ala Tyr Met Val Pro Ser Val Trp Val Gly Val Glu Gly Phe Pro
465                 470                 475                 480

Gln Thr Ser Thr Gly Lys Leu Asp Arg Lys Ala Leu Leu Ala Lys Val
                485                 490                 495

Asp Glu Arg Ala Glu Gly Leu Asp Ser Pro Glu Ala Ala Pro Ser
            500                 505                 510

Gly Gly Arg Glu Ala Thr Leu Leu Gly Ile Trp Arg Glu Val Leu Gln
        515                 520                 525

Arg Pro Asp Leu Ser Pro Asp Asp Phe Phe Ala Ser Gly Gly Asp
    530                 535                 540

Ser Ile Leu Ala Met Arg Thr Leu Ser Arg Ala Arg Glu Ala Gly Ile
545                 550                 555                 560

Asn Tyr Arg Ala Val His Ile Phe Gln His Pro Thr Val Arg Ser Leu
                565                 570                 575

Leu Glu Thr Val Val Gln Ala His Glu Gly Pro Arg Pro Glu Leu Pro
            580                 585                 590

Glu Leu Thr Thr Ser Gly Leu Thr Pro Val Gln Arg Trp Phe Phe Glu
```

```
                 595                 600                 605
Gln Pro Leu Val Asn Arg Gly Phe Trp Asn Gln Ser Ile Leu Leu Arg
610                 615                 620

Leu Thr Arg Pro Met Glu Leu Arg Glu Leu Arg Glu Ile Ala Asp Cys
625                 630                 635                 640

Leu Thr Arg Thr His Gln Ile Leu Ala Cys Glu Ile Asp Glu Lys Gly
                645                 650                 655

Met Arg Leu Gly Ser Arg Asp Ala Asp Ala Cys Cys Ala Gln Val Ser
                660                 665                 670

Leu Thr Thr Gly Ser Gly Thr Ser Ser Pro Glu Phe Ala Arg Ile Ile
                675                 680                 685

Asp Asp Ala His Arg Ser Leu Arg Pro Glu Glu Arg Leu His Arg
690                 695                 700

Leu Val Leu Ile Glu Ser Arg Gly Ser Gly Glu Trp Tyr Leu Phe Trp
705                 710                 715                 720

Thr Ile His His Leu Val Ile Asp Gly Val Ser Trp Arg Ile Leu Leu
                725                 730                 735

Ser Asp Leu Gly Thr Leu Leu Gln Gln Lys Ala Ser Gly Asp Ala Leu
                740                 745                 750

His Leu Glu Lys Ala Pro Val Ser Phe Leu His Cys Ser Glu Arg Met
                755                 760                 765

Arg Ala Leu His Gly Lys Val Arg Glu Ala Glu Leu Ser Tyr Trp Arg
770                 775                 780

Lys Leu Pro Glu Ala Pro Leu Pro Trp Ser Glu Val Arg Gln Glu
785                 790                 795                 800

Val Pro Glu Ala Ala Arg Thr Glu Leu Val Leu Ser Leu Ser Gln Glu
                805                 810                 815

Ala Thr Arg Gly Leu Leu Gln Asp Val Leu Ala Gly Thr Gly Lys Gly
                820                 825                 830

Ile Asn Asp Val Leu Leu Ser Ala Leu Leu Gln Ala Val Tyr Asp Val
                835                 840                 845

Ser Gly Glu Arg Arg Leu Ser Leu Trp Leu Gly His Gly Arg Glu
850                 855                 860

Glu Gly Leu Leu Glu Leu Asp Thr Ser Arg Thr Val Gly Trp Phe Thr
865                 870                 875                 880

Ser Met Phe Pro Val Tyr Leu Glu Ser Pro Ser Pro Glu Asp Phe Gln
                885                 890                 895

Ser Thr Leu Glu Ala Thr Arg Ala Ser Leu Gly Ala Met Pro Asn Arg
                900                 905                 910

Gly Val Gly Tyr Gly Ile Val Arg Tyr Leu Gly Glu Asp Ala Arg Gly
                915                 920                 925

Glu Gly Leu Arg Thr Gly Asn Glu Pro Arg Ile Ser Phe Asn Tyr Leu
                930                 935                 940

Gly Gln Trp Asp Asp Val Ala Ser Asp His Phe Ser Val Val Ser Glu
945                 950                 955                 960

Pro Gly Leu Asp Asp Ile Ala Pro Glu Asn Lys Trp His Arg Glu Val
                965                 970                 975

Asp Ile Asn Cys Leu Val Ala Gln Gly Ile Phe Lys Val His Leu Thr
                980                 985                 990

Phe Val Arg Arg Leu Gln Asp Lys Glu Lys Leu Glu Ser Leu Leu Arg
                995                1000                1005

Arg Phe Ile Ala Arg Leu Glu Ser Ala Ile Asp Ala Tyr Lys Gly
                1010                1015                1020
```

```
Ala Gly Glu Phe Arg Arg Lys Phe Pro Leu Leu Ser Ile Pro Pro
    1025                1030                1035

Glu Ala Phe Ala Arg Asn Gly Ile Asp Leu Gln Ser Val Gln Asp
    1040                1045                1050

Ala Tyr Pro Leu Thr Pro Met Gln Glu Gly Met Leu Leu Arg Ala
    1055                1060                1065

Leu Thr Val Pro Glu Ser Gly Asn Tyr Ile Val Arg Thr Phe Phe
    1070                1075                1080

Asp Leu Thr Gly Glu Leu His Pro Asp Ala Trp Arg Glu Ala Trp
    1085                1090                1095

Arg Arg Glu Leu Ala Glu Gln Glu Leu Leu Arg Ser Ala Phe Phe
    1100                1105                1110

Trp Glu His Ser Pro Thr Pro Phe Gln Val Val Phe Ser His Val
    1115                1120                1125

Asp Leu Asp Trp Arg Thr His Asp Trp Gly His Leu Gly Pro Glu
    1130                1135                1140

Glu Gln Gln Gln Ala Phe Ser Lys Leu Glu Lys Ala Arg His Ala
    1145                1150                1155

Glu Gly Phe Ser Leu Ser Lys Ala Pro Leu Leu Arg Ile Asp Phe
    1160                1165                1170

Ile Ala Arg Gly Gly Ser Asp Tyr Arg Leu Leu Leu Ser Phe His
    1175                1180                1185

His Leu Ile Leu Asp Gly Trp Ser Leu Gln Val Leu Leu Glu Arg
    1190                1195                1200

Val Leu Lys Arg Tyr Gly Gln Ala Arg Gly Gly Gly Glu Glu Arg
    1205                1210                1215

Leu Thr Pro Ala Phe Arg Phe Arg Asp Tyr Val Ala Trp Asn Arg
    1220                1225                1230

Asn His Glu Ser Ser Asp Ala Leu Arg Phe Trp Arg Glu His Leu
    1235                1240                1245

Glu Gly Val Glu Glu Pro Thr Leu Leu Gly Asp Glu Gln Gly Thr
    1250                1255                1260

Arg His Glu Tyr Ala Glu Thr Val Leu Arg Leu Glu Glu Ala Arg
    1265                1270                1275

Trp Ser Gly Leu Gly Ala Arg Cys Arg Arg Gln Gly Met Thr Lys
    1280                1285                1290

Ser Ser Leu Ile Gln Ala Val Trp Cys Trp Val Ala Lys Ser Tyr
    1295                1300                1305

Gly Arg Lys Ser His Val Val Tyr Gly Leu Thr Gln Ala Gly Arg
    1310                1315                1320

Ala Ala Ala Ile Gly Asp Ile Glu Asn Gly Val Gly Leu Phe Ile
    1325                1330                1335

Thr Thr Ser Pro Val Ala Val Asp Leu Asp Lys His Ser Lys Leu
    1340                1345                1350

Ser Thr Val Gly Arg Phe Ile Gln Gln Val Asn Ala Gln Ala Leu
    1355                1360                1365

His His Asp Arg Leu Pro Leu Ser Glu Ile Gln Arg Ile Ser Gly
    1370                1375                1380

Arg Glu Ile Gly Gln Pro Leu Phe Asp Cys Leu Leu Val Phe Glu
    1385                1390                1395

Gln Glu Pro Ile Pro Glu Leu Ala Gly Gly Val Ser Gly Gly Leu
    1400                1405                1410
```

```
Ser Val Ala Gly Thr Arg Thr Tyr Glu Ser Thr Glu Tyr Pro Leu
1415                1420                1425

Thr Leu Ser Ile Leu Glu Lys Arg Asp Gly Ser Cys Asp Leu Arg
1430                1435                1440

Phe Tyr Phe Asn Lys Lys Asn Phe Ser Glu Phe Arg Val Glu Gly
1445                1450                1455

Leu Arg Leu Leu Phe Glu Glu Ile Leu Ala Ala Trp Glu Arg Glu
1460                1465                1470

Gln Glu Leu Glu Leu Ser Ser Leu Pro Ala Phe Pro Ser Arg Asp
1475                1480                1485

Gly Ala Leu Leu Ser Arg Trp Asn Ala Thr Gly Ser Asp Tyr Pro
1490                1495                1500

Ala Gln Ser Leu Thr Glu Leu Phe Leu Gln Gln Ala Arg Arg Thr
1505                1510                1515

Pro Asn His Arg Ala Val Arg Tyr Gly Glu Arg Glu Leu Ser Tyr
1520                1525                1530

Ala Glu Leu Ala Glu Arg Thr Gly Thr Leu Ala Arg Arg Leu Glu
1535                1540                1545

Ala Leu Gly Val Arg Pro Gly Thr Pro Val Ala Val His Met His
1550                1555                1560

Arg Ser Leu Glu Met Val Ile Ala Leu His Ala Ile Val Arg Ala
1565                1570                1575

Gly Gly Ala Tyr Val Pro Ile Asp Pro Glu Tyr Pro Ala Ala Arg
1580                1585                1590

Val Arg Thr Ile Leu Glu Asp Val Ala Ala Pro Val Val Ile Phe
1595                1600                1605

His Asp Ala Ala Pro Leu Lys Cys Gln Val Gly Gly Thr Val Leu
1610                1615                1620

Asp Val Thr Arg Ile Val Glu Glu Gly His Gly Gly Ala Asp His
1625                1630                1635

Arg Ala Ala Glu Tyr Asp Pro Glu Arg Leu Met Tyr Ile Ile Tyr
1640                1645                1650

Thr Ser Gly Ser Thr Gly Arg Pro Lys Gly Val Lys Cys Arg His
1655                1660                1665

Glu Gly Ala Val Asn Arg Ile Cys Trp Met Gln Arg Ser Tyr Pro
1670                1675                1680

Leu Ser Ser Asp Asp Val Val Leu Gln Lys Thr Pro Tyr Thr Phe
1685                1690                1695

Asp Val Ser Val Trp Glu Phe Phe Trp Pro Leu Ala Val Gly Ala
1700                1705                1710

Ser Leu Val Val Ala Ala Pro Gly Val His Gln Asp Ala Ser Ala
1715                1720                1725

Leu Ala Ala Leu Ile Glu Arg Glu Gly Val Thr His Leu His Phe
1730                1735                1740

Val Pro Ser Met Leu Asp Val Phe Leu Ala Ser Lys Gly Gly Ala
1745                1750                1755

Arg Cys Ala Ser Leu Arg Arg Val Phe Cys Ser Gly Glu Ala Leu
1760                1765                1770

Pro Ser Pro Val Val Lys Glu Phe Phe Arg Ser Val Pro His Ala
1775                1780                1785

Glu Leu His Asn Leu Tyr Gly Pro Thr Glu Ala Ser Ile Asp Val
1790                1795                1800

Thr Ala Trp Asp Cys Arg Ser Asp Ser Pro Val Ala Ser Ile Pro
```

```
                1805                1810                1815

Ile Gly Tyr Ala Ile Gln Asn Val Arg Leu His Val Leu Asp Glu
    1820                1825                1830

Lys Gln Ala Pro Val Pro His Gly Val Pro Gly Glu Leu Cys Ile
    1835                1840                1845

Ala Gly Ile Ala Leu Ala Glu Gly Tyr Val Asn Arg Pro Glu Glu
    1850                1855                1860

Thr Ala Lys Arg Phe Val Gln Ser Ser Trp Asp Ala Arg Glu Arg
    1865                1870                1875

Leu Tyr Arg Thr Gly Asp Leu Ala Arg Tyr Leu Pro Asn Gly Ala
    1880                1885                1890

Ile Glu Tyr Leu Gly Arg Leu Asp Gln Gln Val Lys Leu Arg Gly
    1895                1900                1905

Leu Arg Ile Glu Leu Asp Glu Val Ser Ser Val Leu Leu Arg Asp
    1910                1915                1920

Ala Arg Val Arg Gln Ala Val Val Arg Val Val Ala Gly Pro Ala
    1925                1930                1935

Gly Gln Pro Val Leu Ala Ala Tyr Val Val Ala His Glu Gly Ser
    1940                1945                1950

Ala Gly Thr Leu Glu Glu Ala Leu Lys Ala Glu Leu Glu Arg Ser
    1955                1960                1965

Leu Pro Arg Tyr Met Val Pro Glu Phe Phe Phe Leu Glu Ala
    1970                1975                1980

Leu Pro Val Asn Arg Asn Gly Lys Leu Asp Ala Asp Ala Leu Pro
    1985                1990                1995

Arg Pro Gly Ala Ser Ser Ser Arg Glu Trp Glu Pro Pro Gln Thr
    2000                2005                2010

Glu Val Glu Lys Asp Leu Ala Ala Ile Trp Gln Arg Val Leu Gly
    2015                2020                2025

Val Glu Arg Val Gly Arg Asn Asp Ser Phe Phe Ala Leu Gly Gly
    2030                2035                2040

Asp Ser Ile Leu Ser Ile Arg Ile Leu Ala Leu Ala Lys Glu Arg
    2045                2050                2055

Gly Trp Asp Val Ser Leu Gly Glu Leu Phe Arg Ser Pro Arg Leu
    2060                2065                2070

Ser Asp Phe Ala Arg Thr Ala Lys Ala Ala Ala His Thr Pro Val
    2075                2080                2085

Leu Ala Arg Ser Ala Phe Ser Leu Ile Ser Ala Arg Asp Arg Ala
    2090                2095                2100

Ala Met Pro Ala Ser Val Val Asp Ala Leu Pro Ile Ala Ala Leu
    2105                2110                2115

Gln Ala Gly Met Leu Phe His Thr Lys Leu Ala Glu Glu Gly Val
    2120                2125                2130

Met Tyr Arg Asp Ser Phe Leu Tyr Val Ile Gly Gly Glu Phe Asn
    2135                2140                2145

Glu Gln Ala Phe Arg Gln Ala Leu Lys Glu Leu Val His Arg His
    2150                2155                2160

Pro Met Leu Arg Thr Ser Phe Glu Leu Gly Ala Tyr Ser Glu Pro
    2165                2170                2175

Leu Gln Arg Val Glu Arg Glu Val Glu Leu Pro Leu Arg Leu Glu
    2180                2185                2190

Asp Trp Arg Asp Ser Gln Asp Gln Glu Gln Arg Leu Ser Ala Trp
    2195                2200                2205
```

-continued

```
His Glu Ser Tyr Arg Pro Thr Phe Asp Ile Thr Arg Ala Pro Leu
    2210                2215                2220
Phe Lys Met Glu Val Lys Leu Leu Ser Gly Ala Arg Phe Ala Leu
    2225                2230                2235
Gly Leu Cys Phe His His Ala Ile Leu Asp Gly Trp Ser Ile Ala
    2240                2245                2250
Ser Met Met Thr Glu Leu Leu Leu Asp Tyr Gln Arg Leu Leu Thr
    2255                2260                2265
Gly Arg Gly Arg Ala Ile Glu Pro Leu Gly Ser Gly Tyr Ala Asp
    2270                2275                2280
Tyr Leu Glu Leu Glu Lys Arg Val Val Glu Asp Pro Gln Gln Lys
    2285                2290                2295
Ala Phe Trp Ser Thr Tyr Leu Asn Asp Ala Gln Ser Leu Arg Leu
    2300                2305                2310
Pro Val Lys Gln Glu Val Glu His Arg Asn Arg Gly Thr Ser
    2315                2320                2325
Val His Gly Arg Phe Asp Ile Pro Glu Glu Leu Val Gly Gln Leu
    2330                2335                2340
Glu Arg Ile Ala Arg Ser Leu Glu Ile Thr Lys Arg His Leu Phe
    2345                2350                2355
Leu Ala Ala His Phe Arg Val Leu Ala Met Ile Cys Gly His Lys
    2360                2365                2370
Asp Ile Val Ser Gly Val Val Thr Asn Gly Arg Pro Glu Thr Val
    2375                2380                2385
Asp Ala Glu Arg Ile Val Gly Leu Phe Leu Asn Ala Pro Pro Met
    2390                2395                2400
Arg Leu Thr Leu Gly Gly Gly Ser Trp Arg Gln Leu Ile Gln Ala
    2405                2410                2415
Ile Val Glu Glu Glu Arg Asn Ile Leu Pro His Arg Arg Tyr Pro
    2420                2425                2430
Val Ser Glu Met Lys Arg His Cys Val Gln Ala Asp Leu Phe Asp
    2435                2440                2445
Val Ala Phe Asn Tyr Val Asp Phe His Val Tyr Ser Arg Ala Gly
    2450                2455                2460
Glu Leu Ala Ser Val Gly Ile Gln Thr Leu Lys Ala Lys Glu Val
    2465                2470                2475
Thr Asn Phe Gly Leu Tyr Val Thr Phe Tyr Gln Gly Trp Pro Tyr
    2480                2485                2490
Ser Asn Gln Phe Thr Leu Ala Tyr Asp Pro Asp Leu Phe Asp Arg
    2495                2500                2505
Glu Gln Val Asp Gln Phe Ala Arg Tyr Tyr Leu Ala Ala Leu Arg
    2510                2515                2520
Ala Met Ala Gln Ser Leu Glu Gly Arg Tyr Glu Leu Ser Leu Leu
    2525                2530                2535
Thr Pro Glu Glu Arg Ser Ala Leu Leu Ile Ser Gly Glu Pro Pro
    2540                2545                2550
Ala Ser Lys Pro Ala Leu Val Glu Lys Ile Trp Ser Asn Ala Arg
    2555                2560                2565
Ala His Pro Glu Arg Gln Ala Leu Thr Asp Gly Ser Arg Ser Leu
    2570                2575                2580
Ser Tyr Arg Glu Leu Ala Ser Leu Ser Asp Ser Leu Ala Arg Ala
    2585                2590                2595
```

```
Leu His Gln Ala Glu Val Lys Pro Gly Asp Ile Val  Ala Val Asn
    2600                2605                2610

Leu Arg Arg Asp Val His Leu Pro Val Ala Leu Leu  Gly Val Met
    2615                2620                2625

Arg Ala Gly Ala Thr Tyr Leu Pro Leu Asp Asn Arg  Phe Pro Leu
    2630                2635                2640

Glu Arg Gln Ala Phe Met Leu Gln Asp Ser Gly Ala  Lys Leu Val
    2645                2650                2655

Leu Cys Asp Asn Glu Thr Arg Pro Ala Ser Gly Gly  Thr Ala Arg
    2660                2665                2670

Leu Phe Asn Leu Asp Glu Glu Lys Trp Gln Asp His  Gly Gly Glu
    2675                2680                2685

Arg Pro Leu Pro Glu Leu His Ala Glu Ser Ile Ala  Tyr Leu Ile
    2690                2695                2700

Tyr Thr Ser Gly Ser Thr Gly Lys Pro Lys Gly Val  Leu Ile Arg
    2705                2710                2715

His Arg Asn Leu Asp Asn Phe Ile Ala Ser Met Glu  Arg Ser Pro
    2720                2725                2730

Gly Phe Ser Gln Gly Asp Arg Leu Leu Ala Val Thr  Thr Val Ala
    2735                2740                2745

Phe Asp Ile Ala Ala Leu Glu Leu Phe Leu Pro Leu  Ser Cys Gly
    2750                2755                2760

Gly Gln Val Val Leu Ala Pro Glu Gln Val Gly Lys  Asp Ala Thr
    2765                2770                2775

Leu Leu Met Glu Trp Leu Lys Arg His Asp Ile Thr  Val Met Gln
    2780                2785                2790

Ala Thr Pro Ala Thr Trp Gln Gln Phe Val Asp Leu  Gly Trp Arg
    2795                2800                2805

Gly Lys Pro Asp Leu Lys Ile Leu Val Gly Gly Glu  Ala Leu Pro
    2810                2815                2820

Pro Ala Leu Ala Arg Gly Leu Leu Thr Arg Cys Arg  Glu Leu Trp
    2825                2830                2835

Asn Met Tyr Gly Pro Thr Glu Thr Thr Val Trp Ser  Ser Cys Met
    2840                2845                2850

Arg Ile Ala Asp Ser Thr Arg Ile Arg Ile Gly Gln  Pro Ile Ala
    2855                2860                2865

Asp Thr Arg Leu Tyr Val Leu Asp Ala Tyr Gly Asn  Pro Ala Pro
    2870                2875                2880

Arg Gln Thr Val Gly Glu Leu Tyr Ile Ala Gly Gly  Gly Val Ala
    2885                2890                2895

Ala Gly Tyr Trp Arg Arg Pro Asp Leu Thr Arg Glu  Arg Phe Gln
    2900                2905                2910

Asp Asp Pro Phe Phe Gly Gly Pro Met Tyr Arg Thr  Gly Asp Leu
    2915                2920                2925

Ala Arg Ile Asp Ser Arg Asn Glu Val Glu Cys Leu  Gly Arg Thr
    2930                2935                2940

Asp His Gln Val Lys Leu Arg Gly Tyr Arg Ile Glu  Leu Gly Glu
    2945                2950                2955

Ile Asp Ala Ala Ile Gln Glu His Pro Asp Val Ser  Gln Ser Ala
    2960                2965                2970

Val Ile Leu Arg Arg His Ser Glu Arg Gly Asp Glu  Leu Ala Gly
    2975                2980                2985

Tyr Tyr Thr Leu His Asp Glu Ala Leu Ser Arg Arg  Ala Asn Glu
```

```
                    2990              2995                3000

Leu Tyr Gly Glu Gln Val Val Arg Trp Glu Ala Val Trp Ser Glu
        3005                3010                3015

Thr Tyr Gly Arg Ser Lys Glu Asn Arg Gly Ala Leu Asn Leu Ala
        3020                3025                3030

Gly Trp Asn Ser Ser Tyr Thr Gly Gln Pro Met Pro Glu Ala Glu
        3035                3040                3045

Met Arg Glu Trp Ile Asp Glu Thr Val Ala Arg Ile Arg Ser Leu
        3050                3055                3060

Gly Ala Lys Arg Ile Leu Glu Ile Gly Cys Gly Thr Gly Leu Leu
        3065                3070                3075

Leu Ala Arg Leu Ala Pro His Cys Glu Arg Tyr Thr Ala Thr Asp
        3080                3085                3090

Phe Ser Pro Ala Ala Leu Glu Tyr Val Gln Ser Ala Ile Val Pro
        3095                3100                3105

Gln Leu Ser His Leu Asp Cys Glu Val Gln Leu Val Arg Ala Thr
        3110                3115                3120

Ala Asp Arg Leu Glu Gly Val Glu Asp Gly Gln Phe Asp Leu Val
        3125                3130                3135

Ile Leu Asn Ser Val Val Gln Tyr Phe Pro Ser Arg Glu Tyr Leu
        3140                3145                3150

Asp Lys Val Leu Ala Ala Ile Arg Lys Thr Arg Gln Pro Gly
        3155                3160                3165

Arg Ile Phe Val Gly Asp Val Arg His Phe Gly Leu Gly Arg Ala
        3170                3175                3180

Phe His Ala Ser Ile Ala Asp Tyr Gln Ser Lys Gly Ala Leu Ala
        3185                3190                3195

Pro Ala Ala Leu Glu Glu Lys Val Ala Gln Gly Leu Arg Lys Glu
        3200                3205                3210

Thr Glu Leu Leu Leu Ser Pro Arg Tyr Phe Leu Ser Leu Ser Ser
        3215                3220                3225

Leu Gly Val Ala His Ala Glu Ile Glu Leu Arg Arg Gly Thr His
        3230                3235                3240

His Asn Glu Leu Thr Arg Phe Arg Tyr Asp Ala Val Leu Ser Ile
        3245                3250                3255

Gly Gln Arg Pro Glu Gln Leu Glu Thr Arg Trp Tyr Glu Trp Glu
        3260                3265                3270

Thr His Pro Leu Ser Gly Asp Glu Leu Ser Thr Lys Leu Lys Gln
        3275                3280                3285

Ala Gly Glu Cys Phe Gly Leu Arg Ala Val Gly Asn Ala Arg Leu
        3290                3295                3300

Ala Arg Glu Arg Glu Leu Leu Gly Ala Arg Ser Asp Glu Thr Gln
        3305                3310                3315

Gly Ser Ala Gly Ala Gly Ala Gly Leu Asp Pro Glu Gln Leu Tyr
        3320                3325                3330

Arg Leu Ala Glu Ala His Gly Tyr Arg Ala Lys Thr Ser Trp Ala
        3335                3340                3345

Ser Glu His Ala Tyr Gly Ala Phe Asp Val Ala Phe Ile Pro Ala
        3350                3355                3360

Gly Lys Asn Ala Thr Pro Leu Phe Glu Leu Ala Gln Gly Ser Ala
        3365                3370                3375

Arg Leu Ser Asn Ala Pro Leu Leu Ser Gln Ile Asp Val Arg Val
        3380                3385                3390
```

-continued

Gly Ala Glu Ile Arg Arg Ala Leu Gln Lys Asn Leu Pro Glu Tyr
    3395            3400                3405

Met Val Pro Ala Arg Leu Val Leu Leu Asp Ser Met Pro His Thr
    3410            3415                3420

Pro Asn Gly Lys Val Asp Arg Ser Arg Leu Pro Asp Val Gly Arg
    3425            3430                3435

Asn Ala Val Ser Ser Glu Phe Val Glu Pro Arg Asn Glu Asn Glu
    3440            3445                3450

Arg Lys Leu Cys Gln Met Trp Gln Glu Leu Leu Gly Leu Glu Arg
    3455            3460                3465

Val Gly Val Arg Asp Asp Phe Phe Ala Leu Gly Gly His Ser Leu
    3470            3475                3480

Leu Ala Thr Gln Leu Ile Thr Arg Ile Asn Lys Gln Phe Glu Cys
    3485            3490                3495

Asn Leu Ser Leu Arg Ala Leu Phe Asp Phe Pro Thr Ile Glu Gln
    3500            3505                3510

Leu Val Arg Glu Ile Glu Arg Ser Arg Thr Leu Gln Gly Pro Ala
    3515            3520                3525

Met Pro Lys Ile Gln Arg Arg Lys Lys Asn
    3530            3535

<210> SEQ ID NO 9
<211> LENGTH: 5946
<212> TYPE: PRT
<213> ORGANISM: Artificial
<220> FEATURE:
<223> OTHER INFORMATION: Seq.-ID No. 9: Arg3

<400> SEQUENCE: 9

Met His Leu Pro Glu Leu Leu Pro Leu Ser Phe Ala Gln Thr Arg Leu
1               5                   10                  15

Trp Phe Leu Glu Gln Leu Phe Pro Gly Arg Ala Thr Tyr His Ile Pro
            20                  25                  30

Gln Phe Trp Arg Leu Arg Gly Gly Val Asn Val Ser Ala Leu Val Lys
        35                  40                  45

Ala Leu Lys Asn Thr Ala Ala Arg His Glu Ser Leu Arg Thr Thr Phe
    50                  55                  60

Val Thr Glu Asn Gly Glu Pro Arg Gln Ala Ile His Glu Asp Met Ala
65                  70                  75                  80

Leu Asp Phe Glu Cys Glu Thr Leu Asp Glu Arg Gly Gly Glu Thr Leu
                85                  90                  95

Asp Ser Tyr Leu Ser Ala Leu Thr Ala Arg Thr Phe Ser Val Ser Glu
            100                 105                 110

Gly Pro Leu Trp Arg Val Arg Leu Val Arg Thr Ser Ala Arg Glu Gln
        115                 120                 125

Val Leu Ala Val Val Phe His His Ile Ile Cys Asp Gly Trp Ser Met
    130                 135                 140

Gly Ile Phe Ser Arg Glu Val Ser His His Tyr Asn Gln Ala Ile Gly
145                 150                 155                 160

Glu Ser Leu Gly Glu Leu Ser Pro Pro Ile Gln Phe Gly Asp Phe
                165                 170                 175

Ala Gln Trp Gln Arg Glu Trp Leu Gln Gly Glu Arg Leu Glu Leu Gln
            180                 185                 190

Leu Ser Tyr Trp Ala Glu Lys Leu Lys Gly Ala Pro Asp Leu Leu Ala
        195                 200                 205

```
Leu Pro Thr Asp Phe Ser Arg Pro Ala Ala Ser Asn Lys Gly Lys
    210                 215                 220
Leu Tyr Gly Thr Phe Val Pro Pro Glu Val Val Gln Arg Leu Lys Asp
225                 230                 235                 240
Leu Ala Arg Gln Glu Lys Ala Thr Leu Phe Met Val Leu Met Ala Ala
                245                 250                 255
Phe Lys Val Leu Leu Arg Arg Tyr Ser Gly Ser Asp Asp Ile Val Val
                260                 265                 270
Gly Thr Pro Ile Ala Asn Arg His Tyr Pro Asp Val Glu Glu Val Phe
            275                 280                 285
Gly Tyr Phe Ala Asn Thr Leu Ala Leu Arg Thr Pro Leu Glu Gly Ser
        290                 295                 300
Ala Ser Phe Arg Gln Val Leu Gln Arg Val Lys His Ser Thr Leu Glu
305                 310                 315                 320
Ala Tyr Glu His Gln Asp Leu Pro Leu Glu Leu Val Val Asp Lys Leu
                325                 330                 335
Gly Val Glu Arg Asp Leu Ser Arg His Pro Val Phe Gln Val Met Phe
                340                 345                 350
Ala Leu Leu Thr Glu Gly Arg Ser Thr Leu Gly Val Gly Lys Thr Glu
            355                 360                 365
Leu Arg Leu Glu Gly Leu Glu Val Glu Ser Leu Arg Gly Val Gly Asp
        370                 375                 380
Cys Ala Lys Phe Asp Leu Ala Leu Leu Ala Glu Glu Thr Glu Gln Gly
385                 390                 395                 400
Leu Phe Leu Glu Phe Glu Tyr Ser Thr Asp Leu Phe Glu Gln Ala Thr
                405                 410                 415
Ile Glu Arg Val Ala Arg His Phe Gln Asn Leu Leu Val Glu Val Val
                420                 425                 430
Ala Gly Pro Gly Ser Ser Ile Asp Asp Tyr Phe Val Leu Ser Asp Ala
            435                 440                 445
Glu Ile Ala Glu Arg Ile Ala Cys Leu Asp Gly Tyr Gly Leu Pro His
        450                 455                 460
Asp Thr Glu Ile Cys Leu His Gln Trp Val Glu Arg Phe Ala Ala Arg
465                 470                 475                 480
Thr Pro Gln Ala Ile Ala Leu Arg Asp Gln Thr Gly Ser Met Thr Tyr
                485                 490                 495
Arg Glu Leu Asn Glu Glu Ala Asn Arg Leu Ala Arg Cys Leu Leu Glu
                500                 505                 510
Arg Gly Leu Gly His Gly Gln Ile Val Gly Leu Ala Leu Pro Arg Thr
            515                 520                 525
Arg Glu Leu Ile Val Ala Met Val Ala Ala Leu Lys Ala Arg Ala Ala
        530                 535                 540
Tyr Leu Pro Leu Asp Leu Gly Tyr Pro Ser Gln Arg Leu Arg Phe Ile
545                 550                 555                 560
Leu Glu Asp Ala Glu Thr Ala Ala Val Leu Thr Thr Arg Ala His Val
                565                 570                 575
Glu Ser Leu Arg Gly His Cys Lys His Ile Ile Ala Leu Glu Asp Val
                580                 585                 590
Ala Ala Glu Val Ala Gly Gln Ser Ala Gly Asn Leu Asp Leu Asp Tyr
            595                 600                 605
Ala Ser Gly Asp Leu Ala Tyr Leu Ile Tyr Thr Ser Gly Ser Thr Gly
        610                 615                 620
```

```
Lys Pro Lys Gly Ala Thr Ile Cys His Arg Asn Val Thr Arg Leu Phe
625                 630                 635                 640

Pro Asp Pro Glu Pro Leu Tyr Arg Phe Arg Pro Asp Asp Cys Trp Thr
            645                 650                 655

Phe Phe His Ser Cys Ala Phe Asp Leu Ser Val Trp Glu Ile Trp Gly
            660                 665                 670

Ala Leu Ser His Gly Ser Thr Leu Ser Val Val Pro Ala Glu Val Ala
            675                 680                 685

Arg Ser Thr Asp Glu Phe Arg Glu Trp Leu Val Ala His Arg Val Thr
690                 695                 700

Val Leu Asn Gln Thr Pro Ser Ala Tyr Glu Gln Leu Leu Ser Tyr Ile
705                 710                 715                 720

Ser Arg Glu Gly Gly Ser Asp Gly Leu Arg Leu His Thr Val Met Leu
                725                 730                 735

Gly Gly Glu Gly Trp Gly Glu Ala Leu Ala Glu Arg His Arg Gln Leu
                740                 745                 750

Leu Pro His Val Ser Leu Tyr Asn Glu Tyr Gly Pro Ala Glu Cys Ala
            755                 760                 765

Val Trp Thr Thr His Gly Cys Val Tyr Asp Ala Glu Thr Val Gln Ser
770                 775                 780

Tyr Pro Leu Asp Leu Gly Ile Ala His Ser Gln Ser Leu Ala Leu Ile
785                 790                 795                 800

Leu Asn Asp Gly His Arg Val Thr Pro Thr Gly Val Val Gly Glu Leu
                805                 810                 815

Tyr Leu Gly Gly Glu Gly Val Thr Gln Gly Tyr Trp Lys Arg Pro Glu
                820                 825                 830

Leu Asn Lys Glu Lys Phe Val His Val Ser Leu Pro Gly Lys Gly Asn
835                 840                 845

Val Arg Leu Tyr Lys Thr Gly Asp Leu Gly Arg Tyr Lys Ser Asn Gly
850                 855                 860

Arg Ile Glu Phe Ile Gly Arg Arg Asp His Gln Val Lys Val Arg Gly
865                 870                 875                 880

Tyr Arg Ile Glu Leu Gly Glu Ile Glu Ser Ile Leu Arg Ser Leu Pro
                885                 890                 895

Gly Val Arg Asp Ala Leu Val Met Leu Ser Glu Ser Gly Arg Gln Leu
                900                 905                 910

Val Ala Tyr Val Val Gly Glu Gly Gly Thr Leu Thr Gln Glu Thr
            915                 920                 925

Ile Ala Tyr Gln Leu Lys Asp Ala Leu Pro Ala Tyr Met Val Pro Ser
930                 935                 940

Phe Phe Val Leu Leu Glu Arg Phe Pro Met Thr Asn Asn Gly Lys Val
945                 950                 955                 960

Asp Arg Ala Ala Leu Pro Lys Pro His Ala Thr Thr Gly Gln Ser Val
            965                 970                 975

Gly Ala Gln Ala Phe Val Ala Pro Ser Gly Pro Leu Glu Gly Ile
            980                 985                 990

Ala Ser Val Phe Ser Glu Leu Leu Ala Ile Thr Pro Phe Ser Ala Glu
            995                 1000                1005

Gly Asn Phe Phe Ser Leu Gly Gly His Ser Leu Leu Ala Thr Gln
        1010                1015                1020

Ala Ala Ala Lys Ile His Gln Arg Leu Gly Ile Ala Cys Pro Val
        1025                1030                1035

Arg Thr Leu Phe Glu Ser Ser Thr Pro Arg Ala Leu Ala Trp Lys
```

-continued

Leu Gly Gln Glu Gly Thr Lys Gln Ala Val Ala Gly Ala Ala Leu
1055                1060                1065

Pro Val Leu Gln Pro Asn Glu Gln Asp Arg His Gln Pro Phe Pro
1070                1075                1080

Leu Thr Asp Ile Gln Glu Ala Tyr Trp Ile Gly Arg Lys Gly Ala
1085                1090                1095

Leu Thr Leu Gly Glu Val Ser Val His Cys Tyr Ile Glu Tyr Asp
1100                1105                1110

Met Asp Glu Leu Asp Val Gly Arg Leu Glu Arg Ala Leu Asn Arg
1115                1120                1125

Leu Val Gln Arg His Glu Ala Met Arg Leu Val Val Glu Glu Ser
1130                1135                1140

Gly Gln Gln Arg Val Leu Glu Ser Val Pro Phe Tyr Lys Ile Glu
1145                1150                1155

Val Thr Glu Leu Ser Arg Gly Ser Arg Glu Glu Ala Arg Ala
1160                1165                1170

Leu Ala Ser Val Arg Glu Arg Met Ala His Gln Val Leu Pro Ala
1175                1180                1185

Asp Arg Trp Pro Leu Phe Glu Ile Arg Ala Ser Arg Ala His Gly
1190                1195                1200

Phe Trp Arg Leu His Val Ser Leu Asp Ala Leu Val Leu Asp Ala
1205                1210                1215

Trp Ser Leu Asn Leu Ile Phe Asn Glu Trp Ala Arg Leu Tyr Arg
1220                1225                1230

Asp Glu Glu Thr Arg Leu Glu Pro Leu Asn Val Ser Phe Arg Asp
1235                1240                1245

Tyr Val Ile Ala Glu Lys Ala Phe Lys Ser Thr Gln Thr Trp Gln
1250                1255                1260

Lys Ala Lys Asp Tyr Trp Leu Ala Arg Val Ala Thr Leu Pro Asp
1265                1270                1275

Ala Pro Gln Leu Pro Leu Ala Gln Ser Gln Thr Arg Leu Asp Ala
1280                1285                1290

Gln His Phe Asn Arg Glu Gln Lys Arg Leu Thr Pro Glu Ala Leu
1295                1300                1305

Arg Ser Leu Arg Lys Leu Ala Asp Lys His Lys Val Ser Leu Ser
1310                1315                1320

Ser Val Leu Gly Ala Val Phe Ala Asp Val Leu Ser Leu Trp Ser
1325                1330                1335

Ser Lys Pro His Phe Thr Leu Asn Met Thr Leu Phe Asn Arg Leu
1340                1345                1350

Pro Val His Glu Gln Ile Asn Asp Ile Ala Gly Asp Phe Thr Ser
1355                1360                1365

Leu Asn Leu Leu Glu Val Asp Trp Arg Gly Ser Asp Val Pro Phe
1370                1375                1380

Ile Glu Arg Val Arg Lys Val Gln Glu Gln Leu Trp Ser Asp Leu
1385                1390                1395

Asp His Arg Phe Phe Ser Gly Val Gln Val Leu Arg Glu Leu Ala
1400                1405                1410

Arg Ala Arg Asn Asn Pro Ala Val Ala Met Pro Val Val Phe Thr
1415                1420                1425

Cys Leu Leu Gly Ser Thr Glu Gly Glu Gly Gln Ala His Glu Trp
1430                1435                1440

```
Glu Arg Leu Phe Pro Asn Glu Val Phe Asn Ile Thr Gln Thr Pro
1445                1450                1455

Gln Val Trp Leu Asp Tyr Gln Val Tyr Glu Ser Gln Gly Glu Leu
1460                1465                1470

Val Val Cys Trp Asp Tyr Val Glu Gly Leu Phe Pro Glu Gly Leu
1475                1480                1485

Val Gly Ala Met His Glu Ala Tyr Ile Thr Ser Leu Glu Arg Leu
1490                1495                1500

Leu Arg Glu Glu Ser Ala Trp Asn Glu Thr Arg Leu Thr Asn Leu
1505                1510                1515

Pro Glu Ser Gln Arg Ile Arg Arg Glu Glu Ala Asn Ala Thr Ala
1520                1525                1530

Trp Arg Glu Pro Glu Leu Leu Met His Gln Leu Phe Glu Arg Gln
1535                1540                1545

Val Gly Val Ala Pro Asp Ala Thr Ala Val Ile Asp Ser Glu Gly
1550                1555                1560

Ser Tyr Thr Tyr Arg Gln Leu Asn Val Ala Ala Asn Arg Ile Ala
1565                1570                1575

Arg Arg Leu Ala Ser Leu Gly Leu Glu Pro Asn Glu Arg Val Ala
1580                1585                1590

Val Leu Ala Pro Lys Gly Trp Arg Gln Val Val Ala Cys Leu Gly
1595                1600                1605

Ile Gln Lys Ala Gly Ala Ala Tyr Leu Pro Val Asp Gly Ser Ala
1610                1615                1620

Pro Ala Glu Arg Ile Asn Lys Val Leu Glu Leu Gly Arg Val Arg
1625                1630                1635

Ala Ala Val Val Ala Ser Leu Glu Tyr Gly Gly Ala Phe Gly Ser
1640                1645                1650

Asn Ala Leu Ile Val Leu Asp Asp Gly Leu Leu Ala Pro Ala Ser
1655                1660                1665

Gly Thr Glu Asp Val Ser Asn Pro Ala Pro Lys Gln Thr Leu Ala
1670                1675                1680

Asp Leu Ala Tyr Val Ile Phe Thr Ser Gly Ser Thr Gly Thr Pro
1685                1690                1695

Lys Gly Val Met Ile Asp His Arg Gly Ala Val Asn Thr Leu Leu
1700                1705                1710

Asp Ile Asn Glu Arg Phe Gly Val Arg Gln Asp Arg Val Leu
1715                1720                1725

Ala Leu Ser Ser Leu Thr Phe Asp Leu Ser Val Tyr Asp Ile Phe
1730                1735                1740

Gly Leu Leu Ala Ala Gly Gly Ala Val Val Ile Pro Pro Glu Ala
1745                1750                1755

His Val Lys Glu Pro Ala Glu Trp Cys His Trp Leu Val Gln His
1760                1765                1770

Gln Val Thr Val Trp Asn Thr Val Pro Met Phe Met Gln Met Leu
1775                1780                1785

Met Glu Phe Val Gly Ala Leu Pro Val Ala Glu Arg Glu Ala Leu
1790                1795                1800

Ser Arg Thr Leu Arg Leu Val Met Met Ser Gly Asp Trp Ile Pro
1805                1810                1815

Val Glu Leu Pro Asn Thr Ile Lys Arg Val Phe Gln Arg Glu Asp
1820                1825                1830
```

```
Leu Arg Val Met Ser Leu Gly Gly Ala Thr Glu Ala Ser Ile Trp
    1835                1840                1845

Ser Ile Ala Tyr Glu Ile Lys Asp Val Ala Lys Asp Trp Thr Ser
    1850                1855                1860

Ile Pro Tyr Gly Lys Pro Leu Arg Asn Gln Thr Phe His Val Leu
    1865                1870                1875

Asp Glu Gly Met Arg Pro Arg Pro Asp Phe Val Pro Gly Gln Leu
    1880                1885                1890

Tyr Ile Gly Gly Met Gly Val Ala Leu Gly Tyr Phe Gly Asp Glu
    1895                1900                1905

Ala Lys Thr Ala Ala Ser Phe Leu Arg His Pro His Thr Gly Glu
    1910                1915                1920

Arg Leu Tyr Arg Thr Gly Asp Leu Gly Arg Tyr Leu Ala Asp Gly
    1925                1930                1935

Asn Ile Glu Phe Leu Gly Arg Glu Asp Leu Gln Val Lys Val Gly
    1940                1945                1950

Gly His Arg Ile Glu Leu Gly Glu Ile Asp His His Leu His Lys
    1955                1960                1965

Cys Gly Trp Ile Arg Gln Gly Leu Thr His Val Phe Lys Pro Asp
    1970                1975                1980

Gly Arg Asn Pro Gln Leu Val Ala Tyr Leu Val Pro Glu Gly Val
    1985                1990                1995

Thr Gly Lys Ser Glu Gln Glu Arg Ala Glu Glu Leu Ser Phe Lys
    2000                2005                2010

Leu Ala Gly His Asn Leu Arg Lys Thr Gly Gly Ala Gly His Arg
    2015                2020                2025

Leu Val Thr Glu Leu Glu Pro Lys Val Tyr Phe Gln Arg Lys Ser
    2030                2035                2040

Tyr Arg Val Phe Ala Gly Glu Glu Ser Arg Leu Ser Gln Leu Glu
    2045                2050                2055

Ala Trp Leu Arg Ser Ala Leu Leu Pro Gly Lys Pro Leu Ala Thr
    2060                2065                2070

Glu Arg Arg Glu Trp Thr Val Ala Glu Met Leu Ala Pro Leu Leu
    2075                2080                2085

Ala Leu Arg Glu Asp Gly Leu Leu Leu Pro Lys Tyr Arg Tyr Gly
    2090                2095                2100

Ser Ala Gly Ser Leu Tyr Pro Val Gln Thr Tyr Leu Val Met Gly
    2105                2110                2115

Glu Gly Arg Lys Glu Leu Ala Pro Gly Val Tyr Tyr Leu Asp Pro
    2120                2125                2130

Val Lys His Glu Leu Val Arg Leu Ala Asp Gly Ala Leu Ala Cys
    2135                2140                2145

Ser Trp Leu Ser Arg Arg Gly Val Pro Leu Ala Leu Cys Phe Val
    2150                2155                2160

Glu Lys Arg Ser Ala Ile Glu Pro Leu Tyr Gly Thr Arg Ser Asp
    2165                2170                2175

Leu Tyr Ser Ala Ile Glu Gly Ser Met Ala Ala Leu Val Ala
    2180                2185                2190

Ser Ser Thr Ala Ala Ala Gly Ile Ser Trp Arg Thr Arg Ser Ala
    2195                2200                2205

Pro Asp Leu Glu Glu Leu Ala Pro Val Val Leu Glu Ser Ala Asp
    2210                2215                2220

Cys Ser Ala Ile Ala Val Leu Glu Pro Arg Glu Leu Gln Ala Leu
```

```
            2225                2230                2235
Asp Glu Arg Gly Lys Asp Ser Asp Val Ser Val Leu Met Tyr Val
    2240                2245                2250
Met Arg Gly Ser Glu His Gly Pro Arg Thr Gly Trp Tyr Arg Trp
    2255                2260                2265
Ser Gly Asp His Phe Glu Ala Phe Ser Ala Pro Ala Leu Ser Met
    2270                2275                2280
Val Pro Ser Asn Pro Ala Asn Trp Ser Ile Cys Gln Asn Ala Ser
    2285                2290                2295
Phe Ala Leu Phe Val Met Glu Gly Lys Ala Gln Pro Arg Thr Ser
    2300                2305                2310
Ser Ala Leu Phe Thr Gly Arg Leu Ile Gln Ser Leu Met Glu Lys
    2315                2320                2325
Gly Val Gly Leu Gly Leu Gly Gly Cys Ser Ile Gly Glu Met Asp
    2330                2335                2340
Pro Glu Gly Gly Arg Leu Leu Arg Glu Val His Asp Gly Glu Phe
    2345                2350                2355
Val His Ala Phe Phe Gly Gly Pro Val Asp Ser Ala Gln Ile Ser
    2360                2365                2370
Ala Val Gly Thr Ser Glu Ala Glu Pro Phe Glu Gln Leu Val Lys
    2375                2380                2385
Arg Lys Thr Arg Ser Val Leu Glu Gly Ser Leu Pro Gly Tyr Met
    2390                2395                2400
Val Pro Asp His Tyr Val Leu Leu Asp Ser Phe Pro Leu Ser Ser
    2405                2410                2415
Asn Gly Lys Val Asp Arg Ser Arg Leu Ala Ala Pro Glu Leu Glu
    2420                2425                2430
Arg Pro Gln Lys Gln Asp Ala Leu Val Arg Pro Trp Asn Ser Thr
    2435                2440                2445
Glu Ala Val Ile Ala Ser Ile Trp Ala Gln Leu Leu Gly Val Glu
    2450                2455                2460
Pro Asp Ala Ala Asp Asn Phe Phe Ala Leu Gly Gly His Ser Leu
    2465                2470                2475
Thr Ala Thr Gln Leu Cys Thr Arg Leu Arg Glu Ala Phe Gly Val
    2480                2485                2490
Glu Val Pro Leu Arg Glu Val Phe Gly Arg Ala Asp Val Arg Ser
    2495                2500                2505
Gln Ala Ser Met Val Glu Gly Leu Leu Lys Gln His Val Gly Arg
    2510                2515                2520
Gly Ala Ser Ile Pro Arg Arg Ala Gly Thr Gly Arg Ser Val Ala
    2525                2530                2535
Ser Tyr Ala Gln Lys Arg Leu Trp Phe Val Glu Gln Leu Ala Glu
    2540                2545                2550
Asn Gly Ser Val Tyr Gly Met Pro Val Ala Val Ala Leu Gln Gly
    2555                2560                2565
Pro Met Asp Trp Asp Ala Phe Lys Lys Ala Leu Ala Gly Val Val
    2570                2575                2580
Ala Arg His Glu Ile Leu Arg Thr Thr Phe His Met Glu Gln Gly
    2585                2590                2595
Glu Leu Trp Gln Val Ile His Glu Glu Ile Thr Ala Pro Phe Glu
    2600                2605                2610
Thr Glu Gln Cys Pro Glu Gly Ser Val Met Glu Lys Arg Ala Tyr
    2615                2620                2625
```

```
Val Arg Lys Arg Met Arg Glu Leu Ala Arg Val Pro Phe Asp Leu
2630             2635             2640

Ser Thr Gly Pro Leu Leu Arg Phe His Ala Phe Ala Leu Ser Arg
2645             2650             2655

Glu Gln His Ile Leu Phe Gly Ala Met His His Ile Ile Ser Asp
2660             2665             2670

Gly Trp Ser Val Asp Val Phe Gln Ser Glu Leu Ser Ala Leu Tyr
2675             2680             2685

Asn Ala Ala Leu Ser Gly Ser Thr Pro Gln Phe Gln Glu Leu Ser
2690             2695             2700

Ile Gln Tyr Ala Asp Phe Ala Ala Trp Gln Arg Asp Trp Leu Arg
2705             2710             2715

Gly Pro Arg Ser Glu Lys Gln Leu Gln Phe Trp Lys Asp Ser Leu
2720             2725             2730

Ala Gly Ala Pro Glu Leu Leu Gln Leu Pro Thr Asp Leu Pro Arg
2735             2740             2745

Pro Glu Arg Gln Ser Phe Arg Gly Gly Val Val Arg Arg Thr Leu
2750             2755             2760

Asp Ala Gln Leu Thr Ala Glu Ile Asp Ser Arg Cys Arg Glu Trp
2765             2770             2775

Gly Val Thr Pro Phe Met Phe Tyr Leu Ala Ala Tyr Lys Val Leu
2780             2785             2790

Leu Ser Lys Leu Ser Gly Gln Ala Asp Ile Leu Val Gly Thr Pro
2795             2800             2805

Ala Ala Asn Arg His Tyr Ser Gln Val Glu Arg Leu Ile Gly Tyr
2810             2815             2820

Phe Ala Asn Thr Leu Ala Ile Arg Ser Arg Val Glu Gly Gln Arg
2825             2830             2835

Ser Phe Ala Glu Tyr Val Gln Ala Val Arg Glu Gly Val Leu Ala
2840             2845             2850

Ala Asn Glu Asn Gln Asp Val Pro Phe Glu Gln Val Val Glu Ser
2855             2860             2865

Leu Gln Leu Arg Arg Ser Leu Ala Tyr Gln Pro Val Phe Gln Val
2870             2875             2880

Met Phe Val Phe Glu Asn Glu Gly Arg Ser Ser Leu Ser Leu Asn
2885             2890             2895

Gly Val Ser Val Gln Pro Val Ser Leu Asp Ala Gln Val Ala Arg
2900             2905             2910

Phe Asp Leu Thr Leu Leu Ile Arg Asn Ala Gly Asp Ala Arg Glu
2915             2920             2925

Ile Ser Phe Glu Tyr Ser Glu Asp Leu Phe Lys Arg Glu Thr Ala
2930             2935             2940

Ala Glu Trp Leu Asp Gly Val Ile Ser Leu Val Glu Ala Ala Thr
2945             2950             2955

Arg Asp Ser Ser Gln Pro Leu Ala Ala Leu Pro Ser Met Ser Glu
2960             2965             2970

Ala Thr Leu Glu Lys Val Leu Gly Gln Phe Ser Arg Gly Glu Arg
2975             2980             2985

Thr Ala Ser Pro Lys Leu Cys Leu His Glu Gln Phe Glu Arg Val
2990             2995             3000

Val Ala Arg Gln Gly Glu Leu Cys Ala Ile Gln Thr Pro Arg Ser
3005             3010             3015
```

```
Glu Ile Thr Tyr Glu Gln Leu Asn Asp Arg Ala Asn Arg Val Ala
3020                3025                3030

Arg Leu Leu Ser Ser His Gly Ile Arg Lys Gly Asp Val Val Ala
3035                3040                3045

Leu Cys Leu Lys Arg Ser Pro Asp Leu Phe Ala Cys Tyr Leu Ala
3050                3055                3060

Val Leu Lys Leu Gly Ala Val Tyr Val Ala Ile Asp Gly Glu Tyr
3065                3070                3075

Pro Glu Arg Arg Ile Gln His Met Leu Thr Asp Ala Gly Ala Lys
3080                3085                3090

Leu Val Val Ala Ser Pro Val Tyr Ala Asp Lys Leu Gly Thr Ala
3095                3100                3105

Pro Val Leu Val Thr Leu Glu Glu Cys Glu Asp Arg Leu Glu Ser
3110                3115                3120

Met Ala Gly Ser Asn Leu Ser Val Lys Val Ser Pro Glu Asp Val
3125                3130                3135

Ala Tyr Ile Ile Tyr Thr Ser Gly Thr Thr Gly Leu Pro Lys Gly
3140                3145                3150

Ala Arg Val Lys His Arg Gly Val Ser Asn Leu Val Leu Ala Gln
3155                3160                3165

Gln Glu Tyr Phe Val Ala Gly Pro Gly Lys Arg Leu Leu Gln Phe
3170                3175                3180

Ala Ser Cys Ser Phe Asp Gly Ala Ile Trp Glu Trp Thr Thr Ala
3185                3190                3195

Leu Leu Asn Gly Ala Thr Leu Cys Leu Val Ala Glu Ser Ser Ala
3200                3205                3210

Glu Val Val Ser Arg Leu Thr Arg Arg Asp Glu Gln Pro Arg Ile
3215                3220                3225

Asp Ile Ala Ala Leu Pro Pro Ser Val Val Ala Ser Leu Pro Asp
3230                3235                3240

Asp Cys Leu Pro Gly Leu Glu Val Leu Leu Val Ala Gly Glu Ser
3245                3250                3255

Cys Pro Arg Gly Val Val Asp Arg Trp Ser Arg Arg Thr Arg Met
3260                3265                3270

Phe Asn Ala Tyr Gly Pro Cys Glu Ala Ser Val Thr Ser Thr Met
3275                3280                3285

Phe Glu Phe Asp Gly Thr Arg Gly Ala Ser Thr Ile Gly Arg Pro
3290                3295                3300

Leu Arg Asn Cys Asp Val Tyr Ile Leu Asp Glu Arg Met Leu Pro
3305                3310                3315

Val Pro Pro Gly Val Ala Gly Glu Leu Cys Ile Ala Gly Leu Gly
3320                3325                3330

Leu Ala Glu Gly Tyr His Asn Arg Ala Glu Glu Thr Glu Arg Arg
3335                3340                3345

Phe Val Glu Ala Ser Ile Gly Ser Glu Thr Val Arg Met Tyr Arg
3350                3355                3360

Thr Gly Asp Arg Gly Arg Trp Ala Ser Asp Gly Asn Ile Glu Phe
3365                3370                3375

Leu Gly Arg Leu Asp Asn Gln Ile Lys Ile Arg Gly Ile Arg Val
3380                3385                3390

Glu Pro Asp Glu Val Arg Thr Gln Leu Leu Gln Val Pro Gly Val
3395                3400                3405

Ala Gln Ala Ala Val Val Val Asp Arg Glu Gly Gln Glu Thr Arg
```

```
              3410               3415                3420
Leu Leu Ala Tyr Val Val Ala Ser Pro Glu Val Pro Leu Asp Leu
    3425               3430                3435

Glu His Val Arg Lys Arg Leu Arg Ala Ala Leu Pro Glu Ala Leu
    3440               3445                3450

Val Pro Ser Trp Phe Cys Pro Val Ala Thr Leu Pro Met Thr Leu
    3455               3460                3465

Asn Gly Lys Leu Asp Val Glu Ala Leu Pro Arg Pro Gly Glu Glu
    3470               3475                3480

Arg Thr Glu Ala Arg Phe Glu Glu Gly Ala Thr Glu Val Glu Arg
    3485               3490                3495

Lys Leu Gln Ala Leu Ile Ala Gly Val Leu Glu Gly Arg Arg Leu
    3500               3505                3510

Gly Arg His Asp Asp Phe Phe Arg Asn Gly Gly His Ser Leu Lys
    3515               3520                3525

Ala Ile His Leu Val Ala Glu Ile Arg Lys Glu Leu Gly Ala Glu
    3530               3535                3540

Leu Ala Val Lys Thr Ile Phe Asp Ala Pro Thr Val Ala Glu Leu
    3545               3550                3555

Ala Arg Val Ile Glu Ser Glu Arg Arg Gln Glu Gly Pro Thr Ala
    3560               3565                3570

Ser Arg Pro Arg Leu Glu Gly Ser Arg Phe Thr Leu Ser Ala Leu
    3575               3580                3585

Gln Arg Gln Met Trp Leu Ala Glu Lys Val Leu Gln Arg Ser Gly
    3590               3595                3600

Ala Tyr Asn Met Pro Leu Cys Leu Glu Leu Arg Gly Ala Pro Asp
    3605               3610                3615

Ala Ser Ala Leu Gln Asn Ala Val Asp Met Leu Leu Gln Arg His
    3620               3625                3630

Gly Val Leu Arg Trp Gln Phe Lys Glu Glu Ser Gly Glu Pro Tyr
    3635               3640                3645

Ala Glu Asp Cys Gly Val Asp Thr Val Thr Leu Ala Thr Leu Asp
    3650               3655                3660

Trp Arg Glu Leu Gly Gln Gln Glu Lys Asp Thr Ala Leu Ala Gly
    3665               3670                3675

Leu Ile Ala Thr Pro Phe Asn Leu Ser Gln Gly Pro Leu Trp Arg
    3680               3685                3690

Gly Ala Leu Ile Arg Ile Gly Glu Glu Arg Phe Trp Leu Leu Leu
    3695               3700                3705

Cys Ala His His Leu Leu Ala Asp Gly Trp Ser Leu Gly Leu Leu
    3710               3715                3720

Leu Gly Glu Leu Ala Glu Leu Tyr Asn Ala Arg Val Gly His Gly
    3725               3730                3735

Thr Ala Arg Leu Pro Ala Pro Gly Thr Glu Tyr Ser Arg Tyr Val
    3740               3745                3750

Glu Gln Ser Val Gly Asp Glu Arg Glu Leu Glu Arg Gln Leu Glu
    3755               3760                3765

Phe Trp Arg His Gln Leu Glu Gly Ala Pro Gln Arg Leu Ala Leu
    3770               3775                3780

Pro Met Glu Leu Lys Arg Ser Leu Ser Pro Gly Lys Ala Gly Ala
    3785               3790                3795

Val Asp Phe Glu Val Gly Pro Glu Leu Thr Ala Arg Leu Arg Glu
    3800               3805                3810
```

```
Leu Ala Glu Gln Arg Gly Ser  Ser Leu Val Met  Val Leu Met Ser
3815             3820                3825

Thr Tyr Gln Ala Val Leu Ala  Arg Phe Ala Gly  Ala Asp Asp Val
3830             3835                3840

Leu Ile Gly Thr Pro Val Ala  Cys Arg His Lys  Pro Glu Leu Leu
3845             3850                3855

Asn Thr Ile Gly Leu Leu Val  Asn Thr Leu Pro  Ile Arg Leu Ser
3860             3865                3870

Leu Thr Pro Arg Thr Thr Phe  Ala Glu Ala Leu  Ala Gln Val Arg
3875             3880                3885

Gln Arg Leu Leu Glu Gly Met  Ala His Met Asp  Val Pro Phe Glu
3890             3895                3900

Arg Ile Val Ser Ala Val Ala  Gln Glu Arg Glu  Pro Gly Val Pro
3905             3910                3915

Ala Leu Cys Gln Ala Met Phe  Val Trp Glu Gly  Ala Arg Gly
3920             3925                3930

Asp Leu Lys Leu Arg Gly Leu  Asp Val Ser Leu  Lys Ala Thr Pro
3935             3940                3945

Val Thr Ser Ala Lys Tyr Asp  Leu Ala Leu Leu  Ala Ser Glu Gln
3950             3955                3960

Asp Gly Arg Val Thr Gly Arg  Leu Glu Tyr Pro  Glu Gly Leu Tyr
3965             3970                3975

Asp Arg Ala Ser Val Glu Gln  Leu Ala Leu Ser  Tyr Val Lys Leu
3980             3985                3990

Leu Ser Glu Met Ala Lys Asp  Leu Glu Gly Ile  Val Ala Gln Ala
3995             4000                4005

Glu Leu Met Ser Gln Glu Gln  Arg Arg Gln Leu  Glu Ala Trp Phe
4010             4015                4020

Glu Tyr Arg Pro Glu Phe Leu  Glu Ala Pro Asn  Leu His Thr Leu
4025             4030                4035

Ile Glu Arg Gln Ala Ala Thr  Ala Pro Ala Ser  Ser Ala Leu Arg
4040             4045                4050

Tyr Lys Gly Glu Ser Tyr Ser  Tyr Glu Trp Leu  Asn Thr Gln Ala
4055             4060                4065

Asn Arg Leu Ala Arg Tyr Leu  Gly Ala Arg Gly  Ile Gly Arg Gly
4070             4075                4080

Ser Val Val Ala Leu Cys Leu  Ala Arg Ser Pro  Glu Leu Val Val
4085             4090                4095

Ala Trp Val Ala Val Leu Lys  Ser Gly Ala Ala  Phe Val Ser Leu
4100             4105                4110

Asp Pro His Met Pro Gln Ala  Arg Arg Arg Phe  Ile Leu Asp Asp
4115             4120                4125

Ser Arg Thr Ala Leu Val Leu  Ser His Ala Ala  Phe Ala Glu Glu
4130             4135                4140

Leu Gly Thr Gly Thr Asp Ile  Ala Val Trp Glu  Glu Val Ala Lys
4145             4150                4155

Gln Leu Thr Gly Leu Pro Ala  Glu Asn Leu Glu  Leu Glu Val Arg
4160             4165                4170

Gln Glu Glu Leu Ala Tyr Leu  Ile Tyr Thr Ser  Gly Thr Thr Gly
4175             4180                4185

Asn Pro Lys Gly Thr Met Leu  Ala His Arg Gly  Met Ile Asn Leu
4190             4195                4200
```

```
Ala Val Ser Glu Lys Gln Arg Ser Gly Met Gly Pro Gln Ser Lys
4205                     4210                    4215

Val Leu Gln Phe Thr Thr Ala Thr Cys Asp Gly Ser Ile Trp Glu
4220                     4225                    4230

Trp Thr Ser Ala Leu Val Asn Gly Ala Glu Leu Trp Leu Leu Asp
4235                     4240                    4245

Ala Ser Asn Pro Gln Glu Gln Val Ala Gln Ala Met Gln Leu Leu
4250                     4255                    4260

Ser Glu Pro Gly Ile Thr Thr Val Ala Leu Thr Pro Ser Val Val
4265                     4270                    4275

Glu Leu Leu Pro Pro Glu Ala Met Pro Thr Val Gln Ser Leu Thr
4280                     4285                    4290

Leu Ala Gly Glu Ala Cys Pro Leu Ala Leu Leu Glu Lys Trp Ser
4295                     4300                    4305

Ala Arg Ile Pro Gly Val Ala Asn Val Tyr Gly Pro Thr Glu Ala
4310                     4315                    4320

Thr Val Thr Thr Ala Thr Phe Pro Phe Arg Pro Gly Tyr Pro Ala
4325                     4330                    4335

Asn Thr Ile Gly Lys Pro Leu Ala Asn Val Gln Val Tyr Ile Leu
4340                     4345                    4350

Asp Glu His Gly Lys Leu Leu Pro Pro Gly Val Ile Gly Glu Leu
4355                     4360                    4365

Cys Ile Ala Gly Val Gly Leu Ala Leu Gly Tyr Leu Asp Arg Asp
4370                     4375                    4380

Glu Leu Thr Gln Arg Lys Phe Val Thr His Pro Ile Gly Pro Arg
4385                     4390                    4395

Gly Glu Pro Val Arg Val Tyr Arg Ser Gly Asp Leu Ala Arg Tyr
4400                     4405                    4410

Leu Pro Asp Gly His Ile Val Phe Glu Gly Arg Arg Asp Asn Gln
4415                     4420                    4425

Val Lys Val Arg Gly Tyr Arg Val Glu Leu Asp Glu Val Ala Trp
4430                     4435                    4440

Val Leu Lys Gln His Pro Gln Val Gln Gln Ala Ser Val Ile Val
4445                     4450                    4455

Ser Gln Ala Gly Lys Arg Tyr Pro Tyr Leu Val Ala Tyr Val Val
4460                     4465                    4470

Pro Arg Thr Pro Pro Ser Ser Pro Ala Ser Leu Arg Ala Glu Leu
4475                     4480                    4485

Arg Ala Tyr Met Ala Glu Arg Leu Ser His Tyr Met Val Pro Glu
4490                     4495                    4500

Ala Tyr Val Phe Ile Glu Ser Leu Pro Leu Asn Arg Ser Ser Met
4505                     4510                    4515

Lys Val Glu Val Ser Leu Leu Pro Pro Glu Gly Asp Ser Phe
4520                     4525                    4530

Val Arg Asp Thr Leu Val Pro Pro Glu Thr Ala Val Glu Lys Glu
4535                     4540                    4545

Leu Ala Thr Leu Trp Met Glu Leu Leu Gly Val Gly Ser Thr Gly
4550                     4555                    4560

Arg His Asp Ser Phe Phe Arg Leu Gly Gly Asn Ser Leu Leu Ala
4565                     4570                    4575

Val Lys Leu Gly His Ala Ile Gly Glu Arg Trp Gly Cys Asp Ile
4580                     4585                    4590

Ser Leu Pro Arg Ile Phe Glu Asn Asp Thr Leu Ala Ala Leu Ala
```

-continued

```
              4595                4600                4605

Arg Cys Ile Glu Ala Asp Glu Arg Arg Ser His Asp Leu Gln Leu
    4610                4615                4620

Ala Arg Ala Ser Glu Arg Glu Ser Trp Pro Leu Ser Phe Ala Gln
    4625                4630                4635

Gly Arg Met Trp Phe Leu Glu His Leu Thr Gln Gly Ser Ser Ala
    4640                4645                4650

Tyr His Val Pro Leu Val Leu Arg Leu Ile Gly Lys Val Ser Phe
    4655                4660                4665

Glu Arg Leu Ala Gln Ala Leu Ser Ala Leu Val Val Arg His Glu
    4670                4675                4680

Val Leu Arg Thr Ala Tyr Val Glu Asp Gly Asn Thr Leu Ser Gln
    4685                4690                4695

Lys Ile Leu Asp Ala Val Ala Val Glu Met Ala Ser Ser Asp Leu
    4700                4705                4710

Ser Pro Ile Ala Pro Ser Glu Arg Gln Ala Ala Val Asp Arg Leu
    4715                4720                4725

Leu Gly Ala Asp Leu Ala Arg Pro Phe Ala Leu Ala Ala Gly Glu
    4730                4735                4740

Asn Val Arg Ala Arg Leu Val Arg Phe Ser Glu Asp Glu His Leu
    4745                4750                4755

Leu Cys Leu Cys Leu His His Ile Ala Leu Asp Gly Trp Ser Ile
    4760                4765                4770

Ser Val Leu Leu Arg Glu Leu Gly Ser Leu Tyr Arg Gly Gln Pro
    4775                4780                4785

Leu Gln Pro Leu Pro Leu Arg Tyr Val Asp Phe Ala Cys Trp Gln
    4790                4795                4800

Arg Asp Val Leu Glu Lys Arg Phe Ala Glu Gln Leu Asp Tyr Trp
    4805                4810                4815

Lys Ala Glu Leu Arg Glu Leu Pro Arg Gln Leu Glu Leu Pro Trp
    4820                4825                4830

Asp His Pro Arg Pro Pro Arg Gln Asp Tyr Arg Gly Ala Ser Ala
    4835                4840                4845

Arg Arg Pro Leu Ser Gly Glu Leu Arg Ala Ala Leu Lys Gln Val
    4850                4855                4860

Ala Glu Arg Tyr Asp Val Thr Asp Phe Met Leu Tyr Leu Thr Ser
    4865                4870                4875

Phe Gln Leu Trp Leu Gly Arg Leu Ser Asn Ser Cys Asp Val Val
    4880                4885                4890

Val Gly Thr Pro Val Ala Asn Arg His Tyr Asn Gly Val Glu Ser
    4895                4900                4905

Ile Val Gly Leu Phe Val Asn Thr Leu Pro Leu Arg Leu Arg Tyr
    4910                4915                4920

Asp Gly Ser Glu Thr Phe Gly Gly Val Val Arg Arg Met Lys Ser
    4925                4930                4935

Lys Val Leu Glu Ala Tyr Ser His Gln Asp Val Pro Phe Glu Tyr
    4940                4945                4950

Leu Val Asp His Leu Glu Val Pro Arg Glu Leu Ser His Ala Pro
    4955                4960                4965

Ile Phe Gln Ala Met Phe Leu Leu Gln Asp Glu Ser Gly Arg Glu
    4970                4975                4980

Ile Asp Leu Gly Asp Val Gln Gly Arg Ile Ala Pro Val Ala Gly
    4985                4990                4995
```

```
Thr Val Ala Arg Phe Asp Val Ser Leu Leu Val Glu Phe Asp Glu
    5000              5005                5010

Glu Gly Ala Glu Leu Asn Leu Glu Tyr Ala Ser Ala Leu Phe Arg
    5015              5020                5025

Pro Glu Thr Ile Asp Glu Trp Leu Glu Ser Phe Glu Leu Phe Leu
    5030              5035                5040

Arg Ala Ile Ala Ala Asp Ala Glu Ala Pro Val Arg Arg Phe Glu
    5045              5050                5055

Leu Leu Pro Pro Arg Met Arg Ser Phe Leu Ser Glu Val Gly Thr
    5060              5065                5070

Gly Pro Arg Arg Glu Tyr Gly Ser Leu Pro Leu Pro Glu Leu Val
    5075              5080                5085

Ala Glu Gln Ala Lys His Gly Gly Gln Arg Ile Ala Val Glu Gly
    5090              5095                5100

Val Arg Glu Ser Trp Thr Tyr Gly Glu Leu Leu Ala Ala Ala Glu
    5105              5110                5115

Arg Val Ala Ala Gly Leu Gln Arg Arg Gly Val Arg Pro Gly Asp
    5120              5125                5130

Gly Val Ala Ile Ala Leu Pro Arg Asp His Arg Leu Pro Ser Ala
    5135              5140                5145

Met Leu Gly Val Leu Lys Ala Gly Ala Phe Tyr Val Pro Leu Asp
    5150              5155                5160

Leu Thr His Pro Glu Arg Arg Leu Gln Tyr Ile Ala Gly Asp Ala
    5165              5170                5175

Lys Ala Arg Phe Val Ile Thr Gly Gly Glu Thr Arg Phe Gly Phe
    5180              5185                5190

Asp Ile Pro Arg Val Asn Leu Asp Glu Leu Leu Glu Glu Thr Ser
    5195              5200                5205

Glu Ala Arg Pro Val Pro Ile Ala Pro Ser Ser Leu Ala Tyr Val
    5210              5215                5220

Ile Tyr Thr Ser Gly Ser Thr Gly Glu Pro Lys Gly Val Met Val
    5225              5230                5235

Ser His Ala Ser Leu Ser Asn Phe Leu His Ala Met Val Glu Glu
    5240              5245                5250

Leu Gly Phe Gly Pro Asp Glu Arg Leu Leu Ala Ile Thr Thr Ile
    5255              5260                5265

Ala Phe Asp Ile Ser Gly Leu Glu Leu Phe Leu Pro Leu Ile Arg
    5270              5275                5280

Gly Ala Arg Val Val Ile Ala Asp Glu Asp Ser Thr Arg Asp Pro
    5285              5290                5295

Arg Leu Leu Ser Arg Trp Ile Asp Glu Arg Arg Ile Ser Val Met
    5300              5305                5310

Gln Ala Thr Pro Ala Thr Trp Arg Met Leu Met Asp Ala Ser Trp
    5315              5320                5325

Val Ala Pro Gly Ser Phe Lys Ala Leu Val Gly Gly Glu Ala Leu
    5330              5335                5340

Pro Arg Asn Leu Ala Asp Phe Met Thr Ser Arg Val Ser Gln Val
    5345              5350                5355

Trp Asn Val Tyr Gly Pro Thr Glu Ala Thr Ile Trp Ser Thr Ile
    5360              5365                5370

Ala Arg Leu Lys Ser Gly Glu Arg Val His Ile Gly Arg Pro Leu
    5375              5380                5385
```

```
Ala Asn Thr Glu Ala Phe Val Leu Asp Asp Gly Leu Arg Ala Val
5390                5395                5400

Pro Arg Gly Thr Leu Gly Glu Leu His Leu Gly Gly Ser Gly Leu
5405                5410                5415

Ala Thr Gly Tyr Leu Gly Arg Glu Glu Leu Thr Arg Gln Lys Phe
5420                5425                5430

Val His His Pro Glu Leu Gly Arg Arg Leu Tyr Lys Thr Gly Asp
5435                5440                5445

Leu Ala Arg Val Leu Pro Ser Gly Asp Ile Glu Phe Val Ala Arg
5450                5455                5460

Arg Asp Ala Gln Leu Lys Ile Arg Gly Phe Arg Ile Glu Pro Gly
5465                5470                5475

Glu Val Glu Ala Val Leu Ser Arg Val Pro Gly Val Ala Arg Val
5480                5485                5490

Thr Val Leu Pro Val Gly Glu Gly Gly Thr Gln Leu Ala Ala
5495                5500                5505

Phe Leu Leu Thr Gly Asp Glu Arg Leu Gln Ala Gln Ala Arg Ala
5510                5515                5520

Leu Ala Glu Gln Gln Leu Pro Glu Tyr Met Arg Pro Ala Arg Tyr
5525                5530                5535

Val Val Val Pro Glu Phe Pro Leu Thr Pro Asn Gly Lys Val Asp
5540                5545                5550

Thr Lys Ala Leu Arg Ala Leu Val Ser Glu Gln Val Glu Glu Ala
5555                5560                5565

Ala Gly Ser Ala Pro Lys Asn Pro Ile Glu Phe Arg Ile Ser Arg
5570                5575                5580

Leu Trp Ser Ala Leu Leu Gly Val Arg His Pro Gly Thr Arg Asp
5585                5590                5595

Asn Phe Phe Ala Leu Gly Gly Thr Ser Leu Ala Ala Val Arg Leu
5600                5605                5610

Ala Arg Glu Leu Glu Ser Glu Phe Gly Ile Glu Val Arg Val Gly
5615                5620                5625

Asp Ile Phe Arg Lys Pro Thr Ile Ala Glu Leu Ala Gly Leu Val
5630                5635                5640

Glu Thr Gln Gly Ser Glu Arg Val Leu Glu Pro Leu Val Leu Leu
5645                5650                5655

Ser Arg Glu Gln Gln Lys Pro Pro Leu Phe Val Ile His Pro Ala
5660                5665                5670

Gly Gly Met Ala Tyr Cys Tyr Ala Gly Leu Ala Gln Glu Leu Ser
5675                5680                5685

Gly Phe Thr Val His Gly Leu Asn Gln Pro His Tyr Tyr Glu Leu
5690                5695                5700

Glu His Arg Phe Glu Thr Leu Ala Glu Met Ala Ala Asp Tyr Val
5705                5710                5715

Ala Arg Ile Lys Arg Leu Gln Pro Thr Gly Pro Tyr Arg Leu Leu
5720                5725                5730

Gly Trp Ser Phe Gly Gly Thr Leu Ala Tyr Glu Met Ala Arg Gln
5735                5740                5745

Leu Glu Gln Ala Gly Glu Ala Ile Ser Gly Val Val Met Leu Asp
5750                5755                5760

Ala His His Val Ser Pro Leu Gly Ala Asn Leu Pro Thr Val Asp
5765                5770                5775

Val Ser Ala Met Leu Ala Asn Leu Gly Leu Gly Gly Glu Met Ala
```

```
                5780                5785                5790

Asp Pro Tyr Leu Glu Lys Asp Ile Arg Glu Ser Glu Arg Leu Ser
    5795                5800                5805

Arg Asp Tyr Lys Ala Ser Pro Val Arg Phe Pro Val Leu Leu Phe
    5810                5815                5820

Lys Pro Thr Glu Arg Asn Gly Phe Glu Glu Arg Leu Tyr Ala Asp
    5825                5830                5835

Leu Tyr Asn Gly Trp Arg Glu Cys Ala Glu Asn Ser Val Val Arg
    5840                5845                5850

Ser Val Thr Gly Asp His Gly Gly Val Leu Asp Arg Arg Asn Val
    5855                5860                5865

Ser Glu Leu Ala Arg Val Val Glu Ala Phe Leu Ser Gly Gly Tyr
    5870                5875                5880

Gly Val Leu Leu Arg Glu Ala Val Gln Pro Ala Leu Ala Phe Ala
    5885                5890                5895

Leu Ala Glu Arg Asp Arg Phe Val Ala Arg Arg Leu Val Glu Gln
    5900                5905                5910

Leu Pro Arg Asp Leu Val Glu Arg Trp Leu Lys Ser Ala Ile Asp
    5915                5920                5925

Cys Leu Pro Glu Ser Val Arg Pro Glu Gly Ser Phe Val Gln Ala
    5930                5935                5940

Leu Leu Glu
    5945

<210> SEQ ID NO 10
<211> LENGTH: 336
<212> TYPE: PRT
<213> ORGANISM: Artificial
<220> FEATURE:
<223> OTHER INFORMATION: Seq.-ID No. 10: Arg4

<400> SEQUENCE: 10

Met Ile Pro Ser Ser Leu Glu Lys Ala Ile Tyr Gly Val Tyr Ala Thr
1               5                   10                  15

His Ala Leu His Leu Ala Asp Lys His Asn Val Phe Ala Tyr Leu Ala
            20                  25                  30

Glu Lys Gly Ala Ala Ala Pro Gly Glu Ile Ala Lys Ala Val Ala Val
        35                  40                  45

Asp Gly Glu Thr Leu Glu Arg Leu Met Leu Val Leu Gly Ala Leu Glu
    50                  55                  60

Leu Val Gln Ala Gly Ser Asp Gly Lys Tyr Arg Leu Arg Glu Gly Met
65                  70                  75                  80

Gly Pro Tyr Leu Asp Lys Lys Asp Pro Arg Tyr Val Gly Gly Phe Val
                85                  90                  95

Thr His Leu Ile Asn Ser Thr Ser Gly Arg Met Gly His Leu Asp Ala
            100                 105                 110

Tyr Leu Ser Lys Gly Lys Ala Val Val Asp Ala Ala Leu Pro Ser Pro
        115                 120                 125

Phe Asp Val Ile Tyr Lys Asp Glu Ala Ser Thr Lys Glu Phe Met Asp
    130                 135                 140

Ala Met Trp Gln Leu Ser Phe Asp Val Ser Arg Glu Leu Val Lys Leu
145                 150                 155                 160

Ala Gly Leu Asp Ser Cys Arg Gln Leu Val Asp Val Gly Gly Ala Ser
                165                 170                 175

Gly Pro Phe Ser Val Ala Ala Leu Gln His Ser Arg Glu Leu Arg Ser
```

```
                    180                 185                 190
Thr Leu Phe Asp Leu Pro Lys Val Gly Arg Tyr Val Asp Glu Thr Arg
                195                 200                 205
Arg Thr Tyr Gly Leu Glu Glu Arg Leu Arg Phe Val Pro Gly Asp Phe
            210                 215                 220
Phe Arg Glu Glu Leu Pro Glu Gly Asp Cys Phe Ala Phe Gly Tyr Ile
225                 230                 235                 240
Leu Ser Asp Trp Asp Asp Ala Thr Cys Leu Glu Leu Arg Lys Ala
                245                 250                 255
His Arg Ala Cys Arg Ala Gly Arg Val Leu Val Met Glu Arg Leu
                260                 265                 270
Phe Asp Glu Asp Lys Arg Gly Pro Phe Ala Thr Val Phe Met Asn Leu
                275                 280                 285
Ser Met His Val Glu Thr Gln Gly Arg His Arg Thr Ala Arg Glu Tyr
                290                 295                 300
Val Gly Leu Leu Glu Ala Ala Gly Phe Arg Gly Cys Glu Val Arg Arg
305                 310                 315                 320
Ser Ser Arg Asp Lys His Leu Val Ile Gly Leu Lys His Val Thr Thr
                325                 330                 335

<210> SEQ ID NO 11
<211> LENGTH: 383
<212> TYPE: PRT
<213> ORGANISM: Artificial
<220> FEATURE:
<223> OTHER INFORMATION: Seq.-ID No. 11: Arg5

<400> SEQUENCE: 11

Met Arg Val His Leu Pro Gly Glu Cys Glu Asp Ile Val Arg Leu Gln
1               5                   10                  15
Lys Arg Ala Gly Arg Ala Ala Leu Leu Glu Ser Glu Cys Glu Ala Leu
                20                  25                  30
Ser Leu Leu Tyr Asp Arg Val Ser Val Glu Gly Pro Ser Glu Glu Glu
            35                  40                  45
Glu Ile Leu Ala Leu Leu Thr Arg Pro Phe Ser Arg Arg Leu Ala Ile
50                  55                  60
Pro Glu Tyr Tyr Gln Tyr Thr Ser Leu His Val Tyr Gly Trp Phe Leu
65              70                  75                  80
Ser His Tyr Arg Arg Asp Pro Leu Arg Gly Ser Leu Val Ala Leu His
                85                  90                  95
Thr Thr Leu Val Asp Leu Leu Ser Val Glu Glu Gln Gly Ala Arg Leu
                100                 105                 110
Gly Glu Ala Thr Pro Ala Tyr Ile His Glu Arg Ile Arg Gly Leu Arg
            115                 120                 125
Gly Leu Leu Gly Gln Leu Asp Glu Ile Pro Val Asp Arg Asn Gly Pro
130                 135                 140
Leu Phe Val Ala Asp Val Leu Lys Gly Ser Lys Lys Asp Ala Gln Glu
145                 150                 155                 160
Gln Trp Arg Ala Phe Val Leu Ala Arg Cys Thr Gly Phe Pro Lys Ser
                165                 170                 175
Gln Val His Asp Glu Tyr Ile Phe Leu Arg Ser Val His Ala Cys Glu
                180                 185                 190
Ile Val Phe Phe Gln Val Arg Trp Leu Ala Leu Arg Ile Ser Glu Met
            195                 200                 205
Ile Ala Val Asp Arg Lys Glu Ala Val Phe Leu Leu Gly Gln Leu Thr
```

```
Ser Phe Ala Glu Leu Leu Asn Lys Ile Phe Asp Val Leu Lys Thr Met
225                 230                 235                 240

Ser Pro Glu Arg Phe Met Ser Phe Arg Ala Gln Thr Gly Asn Ala Ser
                245                 250                 255

Ala Val Gln Ser Leu Asn His His Ala Met Glu Ile Ala Val Phe Gly
            260                 265                 270

Phe Asp Pro Gly Arg Ala Ser Val Phe Asp Gly Phe Glu His Leu Lys
            275                 280                 285

Arg Leu Asn Glu Pro Leu Phe Arg Glu His Ala Ser Leu Arg Ser Val
        290                 295                 300

Val Glu Ala Thr Ala Asp Gly Ala Leu Ala Glu Gly Phe Ala Lys Leu
305                 310                 315                 320

Asp Arg Cys Leu Leu Arg Trp Arg Gly Gly His Tyr Gly Phe Ala Arg
                325                 330                 335

Lys Tyr Leu Pro Val Asp Ile Lys Gly Ser Gly Gly Thr Glu Gly Ala
            340                 345                 350

Pro Tyr Leu Lys Arg Phe Ile Lys Lys Asp Asp Cys Gln Ser Gly Gly
        355                 360                 365

Gln Arg Pro Gly Thr Asp Ser Glu Leu Ala Arg Phe Phe Phe Cys
    370                 375                 380

<210> SEQ ID NO 12
<211> LENGTH: 27
<212> TYPE: DNA
<213> ORGANISM: Artificial
<220> FEATURE:
<223> OTHER INFORMATION: primer fw1

<400> SEQUENCE: 12
ctcgatatcc cagcgcaaga gctatcg                                         27

<210> SEQ ID NO 13
<211> LENGTH: 27
<212> TYPE: DNA
<213> ORGANISM: Artificial
<220> FEATURE:
<223> OTHER INFORMATION: primer bw1

<400> SEQUENCE: 13
ctcggatccg gtcgggaacc atgtacc                                         27
```

SYNTHETIC PATHWAY ENZYMES FOR THE PRODUCTION OF ARGYRINS

REFERENCE TO RELATED APPLICATIONS AND PRIORITY CLAIM

Figure 1:

This application is a divisional application of and claims priority under 35 U.S.C. §120 from prior pending application Ser. No. 12/999,872, filed Mar. 14, 2011 which is now U.S. Pat. No. 8,404,462, which application was a §371 application of PCT/EP09/57336, filed Jun. 15, 2009, and claimed priority from European Application No. 08159743.7, filed Jul. 4, 2008.

FIELD

The invention relates to nucleic acid sequences encoding synthetic pathway enzymes, which catalyze the production of Argyrins. Accordingly, the invention also relates to the synthetic pathway enzymes, to microorganisms expressing the synthetic pathway enzymes and to a method for production of Argyrins, making use of the synthetic pathway enzymes, preferably expressed in a micro-organism. The invention provides the proteins forming part of or constituting the non-ribosomal peptide synthetases (NRPS) having the activity to catalyse at least one conversion step in the synthesis of Argyrins, including the NRPS constituting the enzymes having the activity to catalyse the synthesis of pre-Argyrin, and additional enzymes having the activity which catalyse the conversion of pre-Argyrin to at least one derivative having the core structure I of Argyrin, including e.g. natural derivatives thereof comprising Argyrin A, Argyrin B, Argyrin C, Argyrin D, Argyrin E, Argyrin F, Argyrin G, and Argyrin H. Synthetic derivatives of Argyrin contain different substituents as R1, R2, R3, and R4 to common structure I.

The synthetic pathway enzymes catalyzing the synthesis of at least one Argyrin comprising the core structure I are encoded by nucleic acid sequences of the invention, containing the structural genes for the synthetic pathway enzymes.

BACKGROUND

Argyrins share the common core structure I:

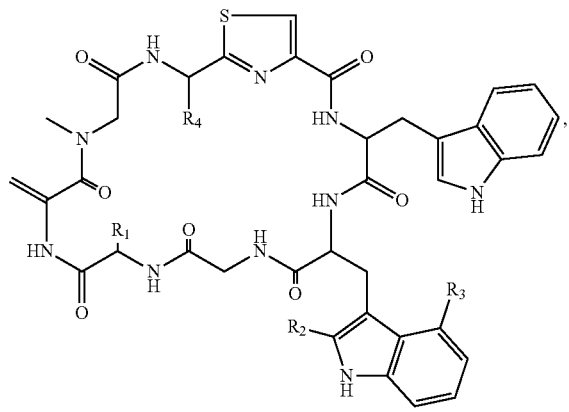

(I)

wherein substituents to R1, R2, R3, and R4 can vary, giving e.g. rise to natural derivatives designated Argyrins A-H. Generally, R1 can be selected from an alkyl group, preferably methyl and ethyl, R2 preferably is hydrogen or methyl, R3 preferably is hydrogen or methoxy, and R4 preferably is selected from hydrogen, methyl and hydroxymethyl, as described in Vollbrecht et al. (Journal of Antibiotics 8, 715-721 (2002)) for Argyrins obtained from *Archangium gephyra*. In dependence on the pattern of substitution, natural Argyrins are designated as follows:

Argyrin A $R_1{=}CH_3$; $R_2{=}H$; $R_3{=}OCH_3$; $R_4{=}CH_3$
Argyrin B $R_1{=}C_2H_5$; $R_2{=}H$; $R_3{=}OCH_3$; $R_4{=}CH_3$
Argyrin C $R_1{=}CH_3$; $R_2{=}CH_3$; $R_3{=}OCH_3$; $R_4{=}CH_3$
Argyrin D $R_1{=}C_2H_5$; $R_2{=}CH_3$; $R_3{=}OCH_3$; $R_4{=}CH_3$
Argyrin E $R_1{=}CH_3$; $R_2{=}H$; $R_3{=}H$; $R_4{=}CH_3$
Argyrin F $R_1{=}CH_3$; $R_2{=}H$; $R_3{=}OCH_3$; $R_4{=}CH_2OH$
Argyrin G $R_1{=}C_2H_5$; $R_2{=}H$; $R_3{=}OCH_3$; $R_4{=}CH_2OH$
Argyrin H $R_1{=}CH_3$; $R_2{=}H$; $R_3{=}OCH_3$; $R_4{=}H$ To-date, Argyrins are obtained from the natural producer organism *Archangium gephyra*, e.g. as a mixture of one or more of the above mentioned Argyrins, collectively referred to as Argyrins A-H, e.g. by isolation from the fermentation broth, and purification by standard methods, e.g. using partition and chromatography.

The use of the original producer strain in production only allows to influence the production rate of Argyrins or the predominant synthesis of one specific Argyrin by altering culture conditions.

U.S. Pat. No. 6,833,447 describes a nucleic acid sequence which encodes a nitrite reductase.

Sasse et al. in The Journal of Antibiotics 543-551 (2002) describe the production of the cell inhibiting compound termed Argyrin B in an *Archangium* strain. No nucleic acid sequence or amino acid sequences for synthetic pathway enzymes for the production of an Argyrin is given.

Rachid et al. in the Journal of Biotechnology 429-441 (2006) describe that *Cytobacter fuscus* is a producer of Argyrin. No nucleic acid sequence or amino acid sequences for synthetic pathway enzymes for the production of an Argyrin is given.

OBJECTS OF THE INVENTION

In view of the limited influence on the production of Argyrin in production methods using cultivation of a natural producer organism, it is an object of the present invention to provide for an alternative production method, and to provide the basis for manipulating the synthetic pathway for the production of Argyrins in micro-organisms, including producer strains and non-producer strains.

General Description of the Invention

The invention achieves the above-mentioned objects by providing the amino acid sequences comprised in or constituting the synthetic pathway enzymes participating in the production of Argyrins, as well as the nucleic acid sequences encoding the synthetic pathway enzymes participating in the production of Argyrins, as well as genetically manipulated micro-organisms containing nucleic acid sequences encoding the synthetic pathway enzymes for the production of Argyrins, the use of nucleic acid sequences hybridizing to the nucleic acid sequences encoding synthetic pathway enzymes participating in the production of Argyrins, e.g. for inserting one or more of these coding sequences, mutating in a targeted manner one or more of these coding nucleic acid sequences, in a wild type producer micro-organism or in a heterologous micro-organism, for production of at least one Argyrin. The invention also comprises nucleic acid sequences having a homology of at least 90%, preferably of at least 95%, more preferably of at least 99% to the coding nucleic acid sequences and encoding synthetic pathway enzymes with a catalytic activity essentially corresponding to the catalytic activity of the coding sequences given below, or which have a nucleotide sequence reverse complementary to the coding sequences given below.

The terminology of the invention includes proteins, peptides, and enzymes in respect of catalytically active proteins for amino acid sequences, as well as oligonucleotides, e.g. DNA and/or RNA, also referred to as coding sequences or genes, for nucleic acid sequences, respectively, as equivalent terms. Unless indicated otherwise, nucleic acid sequences are given from 5' to 3', and amino acid sequences are given from N-terminus to C-terminus. Accordingly, in one embodiment of the invention, a micro-organism is provided, which is genetically manipulated to contain nucleic acid sequences encoding synthetic pathway enzymes for the production of Argyrins, and a method for production of the Argyrins comprising the step of cultivating the genetically manipulated micro-organism. Preferably, the genetically manipulated heterologous micro-organism contains one or more expression cassettes containing the nucleic acid sequences encoding synthetic pathway enzymes for the production of Argyrins, which expression cassettes can be monocistronic or polycistronic.

In a second embodiment, the present invention provides the use of the nucleic acid sequences encoding synthetic pathway enzymes for the production of Argyrins for targeted mutation of these nucleic acid sequences encoding the synthetic pathway enzymes within natural producer strains of Argyrins, e.g. for site directed mutagenesis or for example for inserting one or more additional copies of the least one coding sequence within a monocistronic or polycistronic expression cassette, for altering the amino acid sequence encoded by the nucleic acid sequences of the invention, e.g. for changing the enzymatic activity of the synthetic pathway enzymes, or for inactivating one or more coding sequences encoding a synthetic pathway enzyme. The targeted inactivation of at least one coding sequence results in the change of the synthetic products, e.g. for directing Argyrin synthesis to the preferred production of one or more of Argyrins A to H. Generally, mutations, e.g. insertions, deletions and base exchanges of coding sequences encoding the Argyrins' synthetic pathway enzymes include the targeted mutation of the coding sequence, i.e. a mutation of the translated nucleic acid sections, as well as targeted mutation of the regulatory nucleic acid sections, e.g. of promoters and/or terminators. Mutations preferably cause for example the inactivation, alteration or increase of the catalytic activity of one or more enzymes, resulting in a change of the synthesis of Argyrins, e.g. in an increased Argyrin production or in the production of a different compound of Argyrins A to H when compared to the non-mutated strain.

In the alternative to or in addition to use of the synthetic pathway enzymes as expression products in genetically manipulated micro-organisms, the synthetic pathway enzymes can be expressed from the respective coding sequences and used for synthesis of Argyrins, e.g. in a production process for Argyrins using the synthetic pathway enzymes in a cell-free reaction composition, e.g. in solution or as immobilized enzymes, e.g. bound to the surface of a carrier. Accordingly, the invention provides the use of the amino acid sequences constituting at least one of the synthetic pathway enzymes for the cell-bound and/or cell-free conversion reaction of chemical compounds, e.g. of an Argyrin precursor compound, to an another precursor compound of Argyrin or at least one of the Argyrins.

Further, the invention also relates to the nucleic acid sequences encoding the synthetic pathway enzymes having activity to catalyse the synthesis of at least one Argyrin, the nucleic acid sequences being in substantially purified form, optionally contained in a synthetic nucleic acid construct suitable for genetic manipulation of at least one micro-organism.

DETAILED DESCRIPTION OF THE INVENTION

The invention is described in further detail by way of examples and with reference to the figures, wherein FIG. 1 schematically shows the arrangement of nucleic acid sequences encoding catalytically active amino acid sequences participating in the synthetic pathway of Argyrins, FIG. 2 schematically shows the synthetic steps catalysed by amino acid sequences, i.e. enzymes translated from nucleic acids of FIG. 1, FIG. 3 A shows a schematic representation of the targeted mutation of genes encoding synthetic pathway enzymes, FIG. 3 B shows a gel electrophoresis of PCR products confirming the mutation achieved according to FIG. 3 A, and FIG. 4 shows chromatogramms of HPLC of Argyrins synthesized, namely in A) by the non-mutated wild-type strain, and B) by a mutant obtained according to FIG. 3 A.

The invention provides coding sequences, the translation products of which are synthetic pathway enzymes participating in the production of Argyrins, which coding sequences are contained in SEQ ID NO: 1.

FIG. 1 gives a schematic overview of the arrangement of coding sequences which are contained in a wild-type Argyrin producer isolate that was identified as *Cystobacter* sp., termed strain SB-Cb004. Each nucleic acid sequence constituting an orf and encoding a catalytically active protein is indicated as an arrow, the arrow head designating the 3'-end.

From an analysis of catalytic domains encoded by the orfs identified, it is concluded that the genes designated arg2 and arg3 (black arrows) comprise catalytically active domains for synthesis of pre-Argyrin from amino acids, in co-operation with a radical SAM-domain protein encoded by arg1. Accordingly, genes arg2 and arg3, preferably in combination with arg3, encode the core enzymes for synthesis of pre-Argyrin. Adjacent the genes arg1, arg2, and arg3, there are located genes orf1, orf2, orf3, orf4, orf5, orf6, orf7, orf8, orf9, orf10, orf11, orf12, orf13, and orf14, (orfs1-14) which in FIG. 1 are designated with their numbers only. Orfs 1-14 encode enzymes having catalytic activities catalysing the synthesis of at least one of Argyrins A-H, e.g. from pre-Argyrin or another one of Argyrins A-H as a precursor.

The following table gives the genes identified, which participate in the production of the least one Argyrin.

TABLE

Genes encoding amino acid sequences participating in the synthetic pathway of Argyrins and proposed catalytic activity of the encoded amino acid sequences

| gene | | | encoded protein | | |
|---|---|---|---|---|---|
| name | localization in SEQ.-ID NO. 1 (nt number) | GC [%] | size [aa] | amino acid sequence | proposed function (domain arrangement) |
| orf1 | 1608-4 | 66.3 | 534 | | ABC transporter |
| orf2 | 3615-1687 | 69.4 | 642 | | ABC transporter |
| orf3 | 5139-3661 | 71.1 | 492 | | ATP-dependent RNA helicase |
| orf4 | 7388-5274 | 64.3 | 704 | | elongation factor G |
| orf5 | 7710-8048 | 72.6 | 112 | | |
| orf6 | 8870-8043 | 71.7 | 275 | | pseudouridine synthase |
| orf7 | 9293-10282 | 69.2 | 329 | | |
| orf8 | 11057-10320 | 72.1 | 245 | | RNA methyltransferase |
| arg1 | 11545-13593 (SEQ.-ID NO. 2) | 62.6 | 682 | SEQ.-ID NO. 7 | radical SAM domain protein |
| arg2 | 13706-24322 (SEQ.-ID NO. 3) | 64.8 | 3538 | SEQ.-ID NO. 8 | NRPS loading module and modules 1-2 (A-PCP-E-C-A-PCP-C-A'-MT-A''-PCP) |
| arg3 | 24361-42201 (SEQ.-ID NO. 4) | 66.0 | 5946 | SEQ.-ID NO. 9 | NRPS modules 3-7 (C-A-PCP-HC-A'-Ox-A''-PCP-C-A-PCP-C-A-PCP-C-A-PCP-TE) |
| arg4 | 42239-43249 (SEQ.-ID NO. 5) | 63.7 | 336 | SEQ.-ID NO. 10 | O-methyl transferase |
| arg5 | 43309-44460 (SEQ.-ID NO. 6) | 63.5 | 383 | SEQ.-ID NO. 11 | tryptophane 2,3-dioxygenase |
| orf9 | 45620-44706 | 62.7 | 304 | | |
| orf10 | 46507-45617 | 59.8 | 296 | | |
| orf11 | 47244-46504 | 85.9 | 246 | | N6-DNA methylase |
| orf12 | 47547-47975 | 67.8 | 142 | | |
| orf13 | 48288-49268 | 69.0 | 326 | | |
| orf14 | 49483-55209 | 69.7 | 1908 | | large extracellular alpha-helical protein |
| orf15 | 55212-55565 | 61.9 | 117 | | | nt = nucleotide; orf = open reading frame; aa = amino acid

From the above coding sequences, arg2 and arg3 are considered as essential for the production of Argyrins, e.g. for synthesis of pre-Argyrin, preferably in connection with one or both of arg4 and arg5, more preferably further in addition with a radical SAM domain protein, preferably encoded by arg1.

The nucleic acid sequences for all genes are contained in SEQ ID NO: 1, wherein the genes are located from 5' to 3' and from 3' to 5', as indicated in the sequence listing. Further, genes arg1 to arg5 are given in 5' to 3', as well as their translation products, i.e. the amino acid sequences of the enzymes Arg1 to Arg5.

Accordingly, the present invention in one aspect relates to isolated nucleic acid sequences encoding synthetic pathway enzymes for the production of the least one Argyrins, which nucleic acid sequences comprise at least coding sequences for Argyrin synthetic pathway enzymes, including or consisting of genes encoding enzymes Arg2 (SEQ ID NO: 8) and arg3 (SEQ ID NO: 9), preferably for enzyme Arg1 (SEQ ID NO: 7), and more preferably nucleic acids coding for at least one of enzymes encoded by at least one of orfs1-14,
a heterologous micro-organism containing nucleic acid sequences encoding at least one Argyrin synthetic pathway enzyme, e.g. introduced into a micro-organism by genetic manipulation, preferably integrated into the genome of a heterologous host micro-organism or integrated by genetic manipulation into the genome of an Argyrin producer micro-organism, nucleic acid molecules having a sequence complementary to at least one nucleic acid sequence encoding a synthetic pathway enzyme participating in the production of at least one Argyrin,
a nucleic acid molecule capable of hybridizing, especially under stringent conditions, to a nucleic acid molecule encoding at least one Argyrin synthetic pathway enzyme, especially to the sequence of arg2 and arg3, preferably in combination with arg1,
the translation products of which nucleic acid sequences are synthetic pathway enzymes for the production of Argyrins, and/or which translation products have the activity of at least one synthetic pathway enzyme in the production of Argyrins.

Further, the invention relates to micro-organisms containing nucleic acid sequences encoding at least one synthetic pathway enzyme for the production of at least one Argyrin, preferably nucleic acid sequences comprising arg1, arg2, arg3, arg4, more preferably additionally including arg5. Preferably, the micro-organisms are genetically manipulated to contain these nucleic acid sequences for use in the production of Argyrins, preferably for use in the production of pre-Argyrin.

Figure 2:
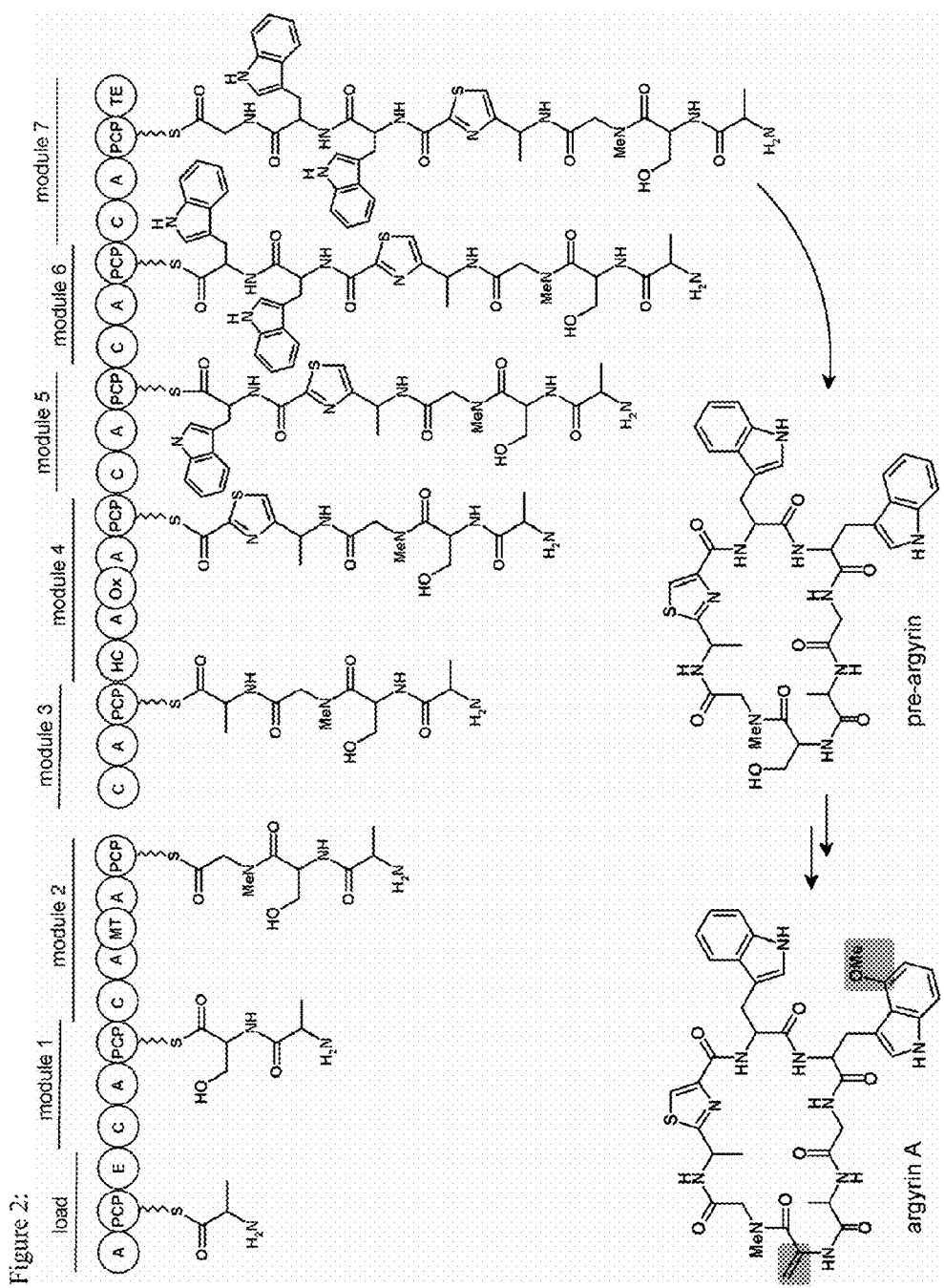

FIG. 2 depicts the synthesis of pre-Argyrin by synthetic pathway enzymes of the invention, wherein the following activities are identifiable in domains of enzymes: A=adenylation domain, PCP=peptidyl carrier protein domain, C=condensation domain, HC=heterocyclization domain, E=epimerization domain, MT=methyl transferase domain, Ox=oxidation domain, and TE=thioesterase domain.

However, the arrangement of domains shown in FIG. 2 is arbitrary and does not necessarily reflect their arrangement in the enzyme.

The core biosynthetic genes are encoded by arg2 and arg3, which are preferably arranged in one common transcriptional unit with arg1, which encodes a radical SAM protein, and more preferably in combination with arg4 and arg5 which encode a O-methyl transferase and a tryptophane 2,3-dioxygenase. In accordance with the natural arrangement of arg2 and arg3 in one transcriptional unit, preferably in combination with arg1, it is preferred that in the nucleic acids of the invention, the coding sequences for arg2 and arg3 are arranged in one transcriptional unit, preferably in combination with arg1 within the same one transcriptional unit. Genes arg4 and arg5 can be contained in the same or a different transcriptional unit.

In detail, FIG. 2 shows the assignment of catalytic domains as derived from the sequence of arg2, comprising the load-module, module 1 and module 2, as well as of arg3 comprising module 3, module 4, module 5, module 6, and module 7, which in co-operation catalyse step-wise synthesis of pre-Argyrin. Initially, the PCP-domain of the load-module, the coding sequence of which is contained in arg2, is charged with the initial alanine by the A domain.

The synthesis of the Argyrin core structure I is obtainable by the combination of translation products of coding sequences comprising, preferably consisting of arg2, arg3, arg4, preferably including arg5, more preferably further including arg1.

As shown on the example of derivatisation of pre-Argyrin to Argyrin A, the derivatisation, i.e. introduction of substituents R1, R2, R3 and/or R4 to the Argyrin of core structure I is catalysed e.g. by the translation products of one or more of orfs1-15.

Analyses of the enzymes show that the translation product of arg1 (Arg1) catalyses the methylation of Argyrin A to form Argyrin B, that the translation product of arg5 (Arg5) catalyses the hydroxylation of the tryptophane ring, and that the translation product of arg4 (Arg4) catalyses the methylation of the OH-group of the tryptophane ring that was introduced by Arg5.

The catalytic activities of translation products of each of orfs1-15 and of arg1, arg4 and arg5 can be identified according to standard methods, e.g. by comparison of their amino acid sequences to known proteins, or preferably by analysis of reaction products generated in the presence of the translation products using defined substrates as precursor compounds for enzymatic catalysis. In the alternative, the catalytic activities of the translation products can be determined by generating mutant micro-organisms containing the genes encoding the enzymes for Argyrine synthesis, which micro-organisms are genetically manipulated to contain a non-functional copy of one or more of these genes replacing the functional gene copies, and analysing the resultant Argyrins synthesized by the micro-organism. For generating one or more non-functional genes, the respective gene copies in a wild-type Argyrin producer strain can be destroyed, e.g. by insertional site-directed mutagenesis as shown below, or a homologous or heterologous non-producer strain can be provided with the genes encoding the synthetic pathway enzymes but lacking one or more of these genes.

Analysis of the resultant Argyrin production can be done by standard methods, e.g. by high-pressure liquid chromatography (HPLC), preferably coupled with a mass-spectrometer.

Example 1

Site-Directed Mutagenesis of an Argyrin Producer and Analysis of Changes in Synthesis of Argyrins On the basis of nucleic acid sequences of genes encoding synthetic pathway enzymes for Argyrin synthesis, a first oligonucleotide fw1 (5'-CTCGATATCCCAGCGCAAGAGCTATCG-3', SEQ ID NO: 12; the EcoRI restriction site is underlined), and a second oligonucleotide bw1 (5'-CTCGGATCCGGTCGGGAACCATGTACC-3', SEQ ID NO: 13, including a BamHI restriction site, underlined) were constructed and used for amplification of a 1.1 kbp DNA fragment of arg3 by PCR (3 min at 95° C., 30 cycles of 30 s at 95° C., 50 s at 56° C., 90 s at 72° C.). The fragment was isolated and ligated into the EcoRI and BamHI restriction sites of an E. coli-Cystobacter shuttle vector pSUP carrying transposon sections and a kanamycin resistance gene, giving vector pArg, schematically shown in FIG. 3A. For conjugational transfer of pArg1, methylation deficient E. coli SCSI 10 harbouring pArg1 and helper plasmid pRK600 for conjugation was grown in LB medium with kanamycin and chloramphenicol (pRK600) to 0.6 OD600. E. coli cells were washed and combined with cells of Cystobacter cultured in 1 mL M medium under shaking at 30° C. for 30 min, collected and resuspended in M medium and plated on M agar containing 100 g/mL kanamycin and 120 g/mL tobramycin. Incubation was at 30° C. until transconjugants appeared, usually after about 3 to 4 days.

Upon conjugational transfer of the vector pArg1 into wild-type isolate Argyrin producer Cystobacter sp., integration of the vector into chromosomal DNA was confirmed by PCR on total DNA isolated from different transformants. An electrophoresis gel of PCR amplificates is shown in FIG. 3B, namely for total DNA isolated from the wild-type (WT), transformant (Mut.), and negative control (E. coli) using primers fw1 and bw1 (indicated as fw1/bw1), primers fw1 and a reverse primer (pSup_B) specific for a section of the original shuttle vector, and primers bw1 and a reverse primer specific for a section of the original shuttle vector (pSup_E).

Figure 3:
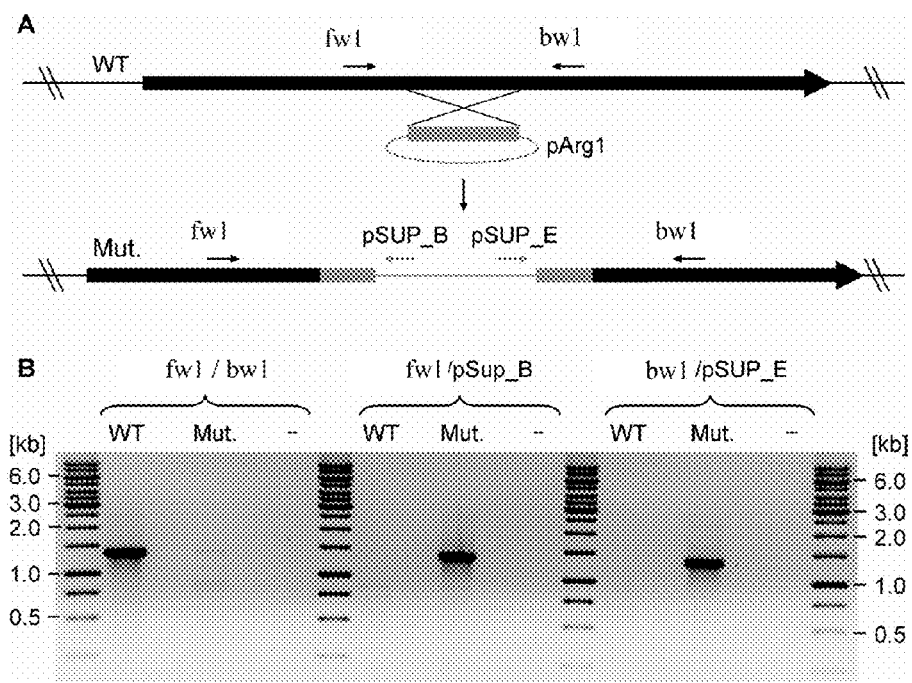

The analysis by gel electrophoresis shown in FIG. 3B demonstrates that the vector was integrated in a site-directed manner within the genomic arg3.

Figure 4:
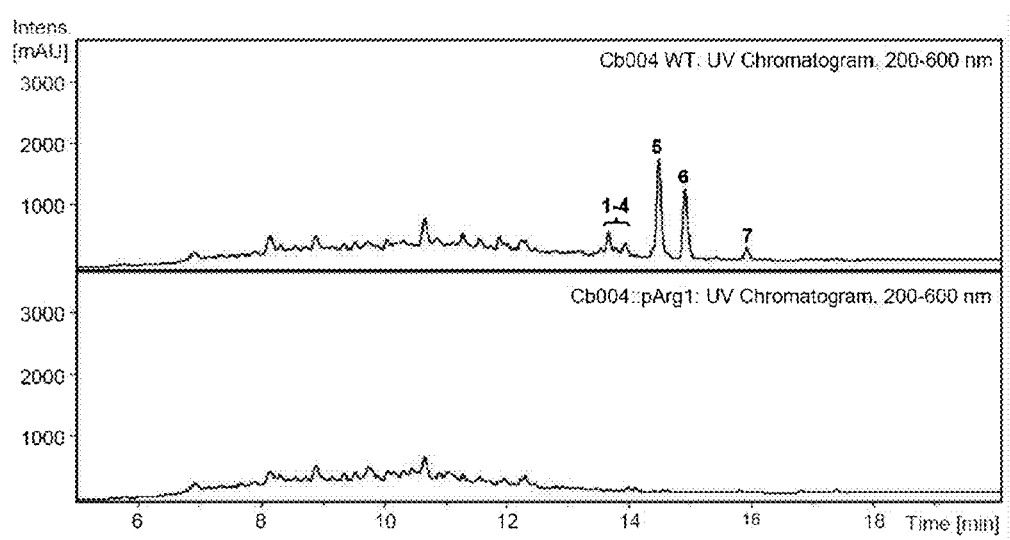

For analysis of the effect of the inactivation of arg3 by insertional site-directed mutagenesis using the nucleotide sequences of the invention, the production of Argyrins was analysed for the wild-type and for the mutated Cystobacter sp. by HPLC. Production of Argyrins was by incubation in M medium in shake flasks in the presence of 2% adsorber resin XAD for 4 days at 30° C. Cells and adsorber resin were collected and extracted with methanol, the extract was concentrated 1:50 and analysed by HPLC-MS (reverse phase 125×2 mm, 3 µm particle size C18 column Nucleodur, Macherey-Nagel, using a 8×3 mm, 5 µm pre-column C18 with diode array detection at 200-600 nm, followed by a HCTplus ion trap mass spectrometer, Bruker, positive and negative ionization detection at 100-1100 amu). HPLC was with a liner gradient 5% B (0.1% formic acid in water) at 2 min to 95% B in A (0.1% formic acid in acetonitrile) by 4 min at 0.4 mL/min. As shown in FIG. 4 A, the wild-type culture produced Argyrin A (peak 5), Argyrin B (peak 6), Argyrin D (peak 7), and Argyrins E to H (peaks 1-4, respectively). In contrast to the wild-type, the mutated strain did not produce any of the Argyrins A, B, D-H, demonstrating the effect of this site-directed mutagenesis by the example of disruption of one gene in a site-directed manner by insertional mutagenesis, and the central role of the enzyme encoded by arg3 for Argyrin synthesis.

Example 2

Production of Argyrin Using an Original Non-Producer Strain by Expression of Genes Encoding the Pathway Enzymes for Argyrin Synthesis For demonstrating the synthesis of Argyrins from the genes encoding the synthetic pathway enzymes, a non-producer micro-organism was provided with the gene cluster comprising the complete synthetic pathway enzymes for Argyrin synthesis including arg1 to arg5 and, optionally, orfs1-15. For transfer of the genes, SEQ ID NO: 1, which contains all of the genes, was transferred into the host organism of the genus myxobacteria, e.g. *Myxococcus xanthus* (described in Perlova et al., AEM 2006, 72, 7485-7494) by the method according to Pradella et al., *Arch. Microbiol.* 178, 484-492 (2002) using conjugational transfer from *E. coli*, preferably according to the genetic modification system using electroporation of myxobacteria in the presence of a carbohydrate as described in EP 1 619 241 A1.

Generally, production of Argyrins by heterologous expression of the nucleic acid sequences in a host micro-organism was monitored by analytical methods as described in Vollbrecht et al. (loc. cit.), preferably by chromatographic purification of an extract from the fermentation broth, with MS coupling and/or NMR of purified fractions. Using these analyses, the Argyrin derivates synthesized by the micro-organism were identified including changes in product spectra, e.g. indicating preferred or reduced synthesis of a specific Argyrin derivate in the heterologous expression host or in a natural producer micro-organism following genetic manipulation of the synthetic pathway genes.

Alternatively, using the method as e.g. described in Gross et al. (Chemistry and Biology 13, 1253-1264 (2006)), *Pseudomonas* spec. could be used for heterologous expression of the synthetic pathway enzymes of the invention, yielding synthesis of Argyrins. Further, the synthetic pathway enzymes could be expressed in *Pseudomonas putida* by adapting the method of Wenzel et al. (Chemistry and Biology 12, 349-356 (2005)), resulting in Argyrin synthesis.

Cultivation of micro-organisms and analysis of Argyrins was according to Example 1, optionally using SM medium containing 5 g/L asparagine, 0.5 g/L $MgSO_4.7H_2O$, 100 mM HEPES, 10 mg/L Fe-EDTA, 0.5 g/L $CaCl_2$, 0.06 g/L $K_2HPO_4$, 10 g/L maltose, pH 7.2, instead of M medium (1.0% soy tryptone, 1.0% maltose, 0.1% $CaCl_2$, 0.1% $MgSO_4.7H_2O$, 50 mM HEPES and 8 mg/L Na-Fe-EDTA, adjusted to pH 7.2).

The wild-type strain without genetic modification did not produce any detectable amount of Argyrins, whereas the transformant produced pre-Argyrin, Argyrin A and Argyrin B, with detectable levels of Argyrins D-H.

The product spectrum of Argyrins could be altered by transformation with a nucleic acid containing at least arg1, arg2 and arg3 with one or more of arg4, arg5, and of orf 1 to orf 15.

---

The invention claimed is:

1. A genetically manipulated microorganism that comprises a recombinant nucleic acid molecule encoding an amino acid sequence having enzymatic activity of synthetic pathway enzymes for the production of Argyrins, wherein the amino acid sequence comprises a combination of:
   (a) the amino acid sequences encoded
      by nucleotides 1608 to 4 of SEQ ID NO: 1 (orf1),
      by nucleotides 3615 to 1687 of SEQ ID NO: 1 (orf2),
      by nucleotides 5139 to 3661 of SEQ ID NO: 1 (orf3),
      by nucleotides 7388 to 5274 of SEQ ID NO: 1 (orf4),
      by nucleotides 7710 to 8048 of SEQ ID NO: 1 (orf5),
      by nucleotides 8870 to 8043 of SEQ ID NO: 1 (orf6),
      by nucleotides 9293 to 10282 of SEQ ID NO: 1 (orf7), and
      by nucleotides 11057 to 10320 of SEQ ID NO: 1 (orf8);
   (b) the amino acid sequences
      of SEQ ID NO: 7 (Arg1),
      of SEQ ID NO: 8 (Arg2),
      of SEQ ID NO: 9 (Arg3),
      of SEQ ID NO: 10 (Arg4), and
      of SEQ ID NO: 11 (Arg5); and
   (c) the amino acid sequences encoded
      by nucleotides 45620 to 44706 of SEQ ID NO: 1 (orf9),
      by nucleotides 46507 to 45617 of SEQ ID NO: 1 (orf10),
      by nucleotides 47244 to 46504 of SEQ ID NO: 1 (orf11),
      by nucleotides 47547 to 47975 of SEQ ID NO: 1 (orf12),
      by nucleotides 48288 to 49268 of SEQ ID NO: 1 (orf13),
      by nucleotides 49483 to 55209 of SEQ ID NO: 1 (orf14), and
      by nucleotides 55212 to 55565 of SEQ ID NO: 1 (orf15).

2. A process for producing Argyrins, comprising cultivating a genetically manipulated microorganism which is genetically manipulated to comprise a recombinant nucleic acid molecule encoding an amino acid sequence having enzymatic activity of synthetic pathway enzymes for the production of Argyrins, wherein the amino acid sequence comprises a combination of:

(a) the amino acid sequences encoded
by nucleotides 1608 to 4 of SEQ ID NO: 1 (orf1),
by nucleotides 3615 to 1687 of SEQ ID NO: 1 (orf2),
by nucleotides 5139 to 3661 of SEQ ID NO: 1 (orf3),
by nucleotides 7388 to 5274 of SEQ ID NO: 1 (orf4),
by nucleotides 7710 to 8048 of SEQ ID NO: 1 (orf5),
by nucleotides 8870 to 8043 of SEQ ID NO: 1 (orf6),
by nucleotides 9293 to 10282 of SEQ ID NO: 1 (orf7), and
by nucleotides 11057 to 10320 of SEQ ID NO: 1 (orf8);
(b) the amino acid sequences
of SEQ ID NO: 7 (Arg1),
of SEQ ID NO: 8 (Arg2)
of SEQ ID NO: 9 (Arg3),
of SEQ ID NO: 10 (Arg4), and
of SEQ ID NO: 11 (Arg5); and
(c) the amino acid sequences encoded
by nucleotides 45620 to 44706 of SEQ ID NO: 1 (orf9),
by nucleotides 46507 to 45617 of SEQ ID NO: 1 (orf10),
by nucleotides 47244 to 46504 of SEQ ID NO: 1 (orf11),
by nucleotides 47547 to 47975 of SEQ ID NO: 1 (orf12),
by nucleotides 48288 to 49268 of SEQ ID NO: 1 (orf13),
by nucleotides 49483 to 55209 of SEQ ID NO: 1 (orf14), and
by nucleotides 55212 to 55565 of SEQ ID NO: 1 (orf15).

3. The process of claim 2, wherein the recombinant nucleic acid molecule has at least 90% sequence identity to SEQ ID NO: 1.

4. The process of claim 2, wherein the recombinant nucleic acid molecule has at least 99% sequence identity to SEQ ID NO: 1.

* * * * *